(12) United States Patent
Walensky et al.

(10) Patent No.: US 10,464,975 B2
(45) Date of Patent: Nov. 5, 2019

(54) STABILIZED ANTI-MICROBIAL PEPTIDES

(71) Applicant: Dana-Farber Cancer Institute, Inc., Boston, MA (US)

(72) Inventors: Loren D. Walensky, Newton Centre, MA (US); Rida Mourtada, Brookline, MA (US); Gregory H. Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/201,235

(22) Filed: Jul. 1, 2016

(65) Prior Publication Data

US 2017/0015716 A1 Jan. 19, 2017

Related U.S. Application Data

(60) Provisional application No. 62/188,448, filed on Jul. 2, 2015, provisional application No. 62/301,518, filed on Feb. 29, 2016.

(51) Int. Cl.
*A61K 38/17* (2006.01)
*C07K 14/46* (2006.01)
*A01N 43/90* (2006.01)
*A61K 38/00* (2006.01)

(52) U.S. Cl.
CPC ............ *C07K 14/463* (2013.01); *A01N 43/90* (2013.01); *A61K 38/1729* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,446,090 A | 8/1995 | Harris | |
| 5,885,829 A | 3/1999 | Mooney et al. | |
| 5,912,231 A | 6/1999 | Houghten et al. | |
| 6,348,558 B1 | 2/2002 | Harris et al. | |
| 7,723,468 B2 | 5/2010 | Daffre et al. | |
| 8,198,405 B2 * | 6/2012 | Walensky ............ | C07K 14/001 530/317 |
| 8,889,632 B2 * | 11/2014 | Bernal ................ | C07K 14/4746 514/21.1 |
| 9,079,970 B2 * | 7/2015 | Walensky ............ | A61K 31/00 |
| 9,296,805 B2 * | 3/2016 | Walensky ............ | C07K 14/605 |
| 9,464,115 B2 | 10/2016 | Walensky et al. | |
| 9,527,896 B2 * | 12/2016 | Bernal ................ | C07K 14/4746 |
| 2001/0025048 A1 | 9/2001 | Crabb et al. | |
| 2003/0096949 A1 | 5/2003 | Hancock et al. | |
| 2005/0250680 A1 | 11/2005 | Walensky et al. | |
| 2006/0287232 A1 | 12/2006 | Clayberger et al. | |
| 2010/0069308 A1 | 5/2010 | Chorny et al. | |
| 2011/0159091 A1 | 6/2011 | Stone et al. | |
| 2011/0288007 A1 | 11/2011 | Fox et al. | |
| 2014/0113857 A1 * | 4/2014 | Walensky ............ | C07K 14/82 514/6.9 |
| 2014/0155319 A1 | 6/2014 | Bond et al. | |
| 2014/0296232 A1 | 10/2014 | Hung et al. | |
| 2014/0370042 A1 | 12/2014 | Walensky et al. | |
| 2015/0087512 A1 | 3/2015 | Wang et al. | |
| 2015/0087579 A1 | 3/2015 | Stange et al. | |
| 2016/0046671 A1 * | 2/2016 | Leshchiner ........... | C07K 7/08 514/19.3 |
| 2016/0068834 A1 * | 3/2016 | Walensky ............ | C07K 14/47 435/188 |
| 2016/0110706 A1 * | 4/2016 | Li ........................ | G06K 19/077 705/44 |
| 2016/0319436 A1 * | 11/2016 | Wagh .................... | B32B 15/04 |
| 2017/0081379 A1 * | 3/2017 | Bernal ................ | C07K 14/4746 |
| 2017/0247423 A1 * | 8/2017 | Walensky ............ | A61K 38/08 |
| 2017/0260248 A1 * | 9/2017 | Walensky ............ | C07K 14/575 |

FOREIGN PATENT DOCUMENTS

| | | |
|---|---|---|
| CA | 2367149 C | 9/2011 |
| DE | 19914817 A1 | 10/2000 |
| WO | WO 199914259 | 3/1999 |
| WO | WO 199934833 | 7/1999 |
| WO | WO 2000/04915 A1 | 2/2000 |
| WO | WO 2008/086042 A2 | 7/2008 |
| WO | WO 2008121767 | 10/2008 |
| WO | WO 2009108261 | 9/2009 |
| WO | WO 2010060112 | 5/2010 |
| WO | WO 2010068684 | 6/2010 |
| WO | WO 2010148335 | 12/2010 |
| WO | WO 2013/039857 A1 | 3/2013 |
| WO | WO 2014/100777 A2 | 6/2014 |

(Continued)

OTHER PUBLICATIONS

Imura, Yuichi et al, "Magainin 2 in action: distinct modes of membrane permeabilization in living bacterial and mammalian cells." Biophys. J. (2008) 95 p. 5757-5765.*
Messer, William S. "Posterior pituitary hormones." http://163.178.103.176/casosberne/8hendocrino/caso44-2/htmlc/casosb2/v2/vasopressin.htm, available 2000.*
Wimley, William C.; "Describing the mechanism of antimicroibal peptide action with teh interfacial activity model." ACS Chem. Biol. (2010) 5(10) p. 905-917.*
Park, Chan Bae et al, "Mechanism of action of the antimicrobial peptide buforin II: buforin ii kills microorganisms by penetrating the cell membrane and inhibiting cellular functions." Biochem. Biophys. Res. (1998) 244 p. 253-257.*
Hoskin, David W. and Ramamoorthy, Ayyalusamy, "STudies on anticancer activities of antimicrobial peptides." Biochim. Biophys. Acta (2008) 1778(2) p. 357-375.*

(Continued)

*Primary Examiner* — Fred H Reynolds
(74) *Attorney, Agent, or Firm* — Fish & Richardson P.C.

(57) ABSTRACT

The present invention provides methods of designing and making structurally stabilized anti-microbial peptides for the prophylaxis and treatment of infection. Methods are also disclosed for designing stabilized anti-microbial peptides that are selectively lytic/cytotoxic to bacteria, allowing for internal use of anti-microbial peptides without mammalian membrane disruption and cytotoxicity.

79 Claims, 18 Drawing Sheets

Specification includes a Sequence Listing.

(56) References Cited

FOREIGN PATENT DOCUMENTS

| WO | WO 2014/159969 | 10/2014 |
| --- | --- | --- |
| WO | WO 2015/070912 | 5/2015 |
| WO | WO 2015/138494 A1 | 9/2015 |
| WO | WO 2017/004591 A2 | 1/2017 |
| WO | WO 2017/151617 A1 | 9/2017 |

OTHER PUBLICATIONS

Walensky, Loren D. et al, "Activation of apoptosis in vivo by a hydrocarbon stapled bh3 helix." Science (2004) 305 p. 1466-1471.*
Liu, Jennifer L. et al, "Use of LC/MS peptide mapping for characterization of isoforms in 15N-labeled recombinant human leptin." in Techniques in protein chemistry VIII (1997), Daniel Marshak, Ed. ISBN 0-12-473557-6.*
Barker, D. G. and Bruton, C. J., "The fate of norleucine as a replacement for methionine in protein synthesis." J. Mol. Biol. (1979) 133 p. 217-231.*
Chapman, Ross N. et al, "A highly stable short alpha-helix constrained by a main-chain hydrogen bond surrogate." J. Am. Chem. Soc. (2004) 126 p. 12252-12253.*
Yin, Hang et al, "Alpha helix mimetics in drug delivery" from "Drug discovery research: new frontiers in the post genomic era", Huang ed., isbn 978-0-471-67200-5, p. 280-298.*
Yampolsky, Lev Y. and Stoltzfus, Arlin, "THe exchangeability of amino acids in proteins." Genetics (2005) 170 p. 1459-1472.*
Chapuis et al., Effect of hydrocarbon stapling on the properties of α-helical antimicrobial peptides isolated from the venom of hymenoptera, Amino Acids, 43(5):2047-58 (Nov. 2012) http://dx.doi:10.1007/s00726-012-1283 Epub Apr. 17, 2012.
Dinh, et al., Antimicrobial Activity of Doubly-Stapled Alanine/Lysine-Based Peptides, Bioorg & Med Chem Lett. 25(18):4016-9 (Sep. 15, 2015) http://dx.doi.org/10.1016/j.bmcl.2015.06.053.
Pham et al., Truncated and constrained helical analogs of antimicrobial esculentin-2EM, Bioorg & Med Chem Lett., 23(24):6717-20 (Dec. 2013) http://dx.doi.org/10.1016/j.bmcl.2013.10.031.
PCT International Search Report for Int. App. No. PCT/US2016/040849, dated Jan. 10, 2017 (7 pages).
PCT Written Opinion of the International Searching Authority for Int. App. No. PCT/US2016/040849, dated Jan. 10, 2017 (13 pages).
Altschul et al. (1997) Gapped BLAST and PSI-BLAST: a new generation of protein database search programs, Nucleic Acids Res. 25:3389-3402.
Amsel et al. (1983) Nonspecific vaginitis. Diagnostic criteria and microbial and epidemiologic associations, Am. J. Med. 74:14-22.
Bang, et al., (2004) Total chemical synthesis of crambin, J. Am. Chem. Soc. 126:1377-83.
Bird et. al., (2008) Synthesis and biophysical characterization of stabilized alpha-helices of BCL-2 domains, Meth Enzymol., 446:369-386.
Bird et al., (Aug. 2010) Hydrocarbon double-stapling remedies the proteolytic instability of a lengthy peptide therapeutic, Proc Natl Acad Sci USA 107(32):14093-8.
Bird et al, (Sep. 2011) Chemical synthesis of hydrocarbon-stapled peptides for protein interaction research and therapeutic targeting, Curr Protoc Chem Biol., 3(3):99-117.
Blackwell et al., (Aug. 2001) Ring-closing metathesis of olefinic peptides: design, synthesis, and structural characterization of macrocyclic helical peptides, J Org Chem., 66(16): 5291-5302.
Devi et al., (Aug. 1991) Antibodies to poly[(2-8)-alpha-N-acetylneuraminic acid] and poly[(2-9)-alpha-N-acetylneuraminic acid] are elicited by immunization of mice with Escherichia coli K92 conjugates: potential vaccines for groups B and C meningococci and E. coli K1, Proc. Natl. Acad. Sci. USA 88(16):7175-7179.
Fattom et al. (Jul. 1990) Serum antibody response in adult volunteers elicited by injection of Streptococcus pneumoniae type 12F polysaccharide alone or conjugated to diphtheria toxoid, Infect. Immun., 58(7):2309-2312.

Forsum et al. (Feb. 2005) Bacterial vaginosis—a microbiological and immunological enigma, APMIS 113(2):81-90.
Gupta et al., (Oct. 2004), Valacyclovir and Acyclovir for Suppression of Shedding of Herpes Simplex Virus in the Genital Tract, J. Infect. Dis., 190:1374-1381.
Hawes et al. (1996), Hydrogen Peroxide-Producing Lactobacilli and Acquisition of Vaginal Infections, J. Infect. Dis. 174:1058-1063.
Hillier et al. (Dec. 1995) Association between bacterial vaginosis and preterm delivery of a low-birth-weight infant. The Vaginal Infections and Prematurity Study Group, N. Engl. J. Med. 333(26):1737-1742.
Kawamoto et al. (Feb. 2012) Design of triazole-stapled BCL9 α-helical peptides to target the β-catenin/B-cell CLL/lymphoma 9 (BCL9) protein-protein interaction, J Med Chem. 55(3):1137-46.
Li et al., (Dec. 1989) Comparative immunogenicities of Vi polysaccharide-protein conjugates composed of cholera toxin or its B subunit as a carrier bound to high- or lower-molecular-weight Vi, Infect. Immun. 57(12):3823-3827.
Schafmeister et al. (2000) An All-Hydrocarbon Cross-Linking System for Enhancing the Helicity and Metabolic Stability of Peptides, J Am Chem Soc., 122:5891-5892.
Szu et al., (Nov. 1987) Vi capsular polysaccharide-protein conjugates for prevention of typhoid fever. Preparation, characterization, and immunogenicity in laboratory animals, J. Exp. Med. 166(5):1510-1524.
Szu et al., (Dec. 1991) Relation between structure and immunologic properties of the Vi capsular polysaccharide, Infect. Immun. 59(12):4555-4561.
Szu et al., (Oct. 1994) Laboratory and preliminary clinical characterization of Vi capsular polysaccharide-protein conjugate vaccines, Infect. Immun. 62(10):4440-4444.
Verstraelen et al. (Oct. 2004) Culture-independent analysis of vaginal microflora: the unrecognized association of Atopobium vaginae with bacterial vaginosis, Am J. Obstet. and Gynecol. 191(14):1130-1132.
Walensky et al., (Sep. 2004) Activation of apoptosis in vivo by a hydrocarbon-stapled BH3 helix, Science, 305(5689):1466-1470.
Wilen, S. H., et al., (1977) Strategies in Optical Resolutions, Tetrahedron 33:2725-2736,first page only.
Williams et al. (1991) Asymmetric Synthesis of Monosubstituted and a,a-Disubstituted a-Amino Acids via Diastereoselective Glycine Enolate Alkylation, J. Am. Chem. Soc., 113:9276-9286.
Williams et al., (2003) Efficient Asymmetric Synthesis of N-tert-Butoxycarbonyl □-Aminoacids Using 4-tert-Butoxycarbonyl-5,6-Diphenylmorpholin-2-One: (R)-(Ntert-butoxycarbonyl)allylglycine [(4-Pentenoic acid, 2-[[(1,1-dimethylethoxy)carbonyl]amino]-, (2R)-)], Org. Synth., 80:31-37.
Yang et al., (1986) Calculation of Protein Conformation from Circular Dichroism, Methods Enzymol. 130:208-269.
Acharya, T. Extracellular and Intracellular Bacteria and Their Preferred Growth Phase Within the Host, Bacteriology, May 30, 2013 (5 pages).
Atashili, et al., Bacterial Vaginosis and HIV Acquisition: A Meta-Analysis of Published Studies, AIDS, 22(12):1493-1501 (Jul. 2008).
Bernal, et al., A Stapled p53 Helix Overcomes HDMX-Mediated Suppression of p53, Cancer Cell. 18(5):411-422 (Nov. 2010).
Bird, et al., Mucosal delivery of a double-stapled RSV peptide prevents nasopulmonary infection, J Clin Invest. 124(5):2113-2124 (May 2014).
Brogden, KA, Antimicrobial peptides: pore formers or metabolic inhibitors in bacteria? Nat. Rev. Microbiol. 3(3):238-250 (Mar. 2005).
Bustillo, et al., Modular analysis of hipposin, a histone-derived antimicrobial peptide consisting of membrane translocating and membrane permeabilizing fragments, Biochimica Et Biophysica Acta (BBA)—Biomembranes. 1838(9):2228-2233 (2014).
Chang, et al., Stapled α-helical peptide drug development: A potent dual inhibitor of MDM2 and MDMX for p53-dependent cancer therapy, PNAS U.S.A., 110(36):E3445-3454 (Sep. 2013).
Fields et al., Chapter 3 in Synthetic Peptides: A User's Guide, ed. Grant, W. H. Freeman & Co., New York, N.Y., 1992, p. 77, p. 77-183.

(56) References Cited

OTHER PUBLICATIONS

Fjell, et al., Designing antimicrobial peptides: form follows function, Nat Rev Drug Discov. 11(1):37-51 (Dec. 2011).
Gordon, et al., A Review of Antimicrobial Peptides and Their Therapeutic Potential as Anti-Infective Drugs, Curr Eye Res. 30(7):505-515 (Jul. 2005).
International Search Report and Written Opinion for Int. App. No. PCT/US2017/019953, dated Aug. 4, 2017 (21 pages).
International Search Report and Written Opinion for Int. App. No. PCT/US2016/040849, dated Jan. 10, 2017 (21 pages).
Klevens, et al., Estimating Health Care-Associated Infections and Deaths in U.S. Hospitals, Public Health Reports. 122(2):160-166 (Mar. 2007).
Mansour, et al., Host defense peptides: front-line immunomodulators, Trends Immunol. 35(9):443-450 (Sep. 2014).
Nicolas, Pierre, Multifunctional host defense peptides: intracellular-targeting antimicrobial peptides, FEBS Journal. 276(22):6483-6496 (Nov. 2009).
Park, et al., Structure-activity analysis of buforin II, a histone H2A-derived antimicrobial peptide: The proline hinge is responsible for the cell-penetrating ability of buforin II, Proceedings of the National Academy of Sciences. 97(15):8245-8250 (Jul. 2000).
Patgiri, et al., Solid-phase synthesis of short α-helices stabilized by the hydrogen bond surrogate approach, Nat Protoc. 5(11):1857-1865 (Nov. 2010).
Pereira, et al., Maximizing the Therapeutic Window of an Antimicrobial Drug by Imparting Mitochondrial Sequestration in Human Cells, J. Am. Chem. Soc. 133(10):3260-3263 (Mar. 2011).
Rose, et al., Potential Role of Epithelial Cell-Derived Histone H1 Proteins in Innate Antimicrobial Defense in the Human Gastrointestinal Tract, Infect Immun. 66(7):3255-63 (Jul. 1998).
Shah, et al., The proteome targets of intracellular targeting antimicrobial peptides, Proteomics. 16(8):1225-37 (Apr. 2016).
Thaker, et al., Synthetic Mimics of Antimicrobial Peptides with Immunomodulatory Responses, J. Am. Chem. Soc. 134(27):11088-11091 (Jul. 2012).
Walensky, et al., Hydrocarbon-Stapled Peptides: Principles, Practice, and Progress, J. Med. Chem. 57(15):6275-6288 (2014).
Wiegand, et al., Agar and broth dilution methods to determine the minimal inhibitory concentration (MIC) of antimicrobial substances, Nat Protoc. 3(2):163-175 (2008).
Yi, et al., Solution structure of an antimicrobial peptide buforin II, FEBS Letters. 398(1):87-90 (Nov. 1996).
Zasloff, M., Antimicrobial peptides of multicellular organisms, Nature, 415(6870):389-395 (Jan. 2002).
U.S. Appl. No. 15/445,502, filed Feb. 28, 2017, Walensky et al.
Jenner et al., *Hydrocarbon-stapled lipopeptides exhibit selective antimicrobial activity*, Biopolymers. 108(3) (May 2017).
Liu et al., *Intramolecular cyclization of the antimicrobial peptide Polybia-MPI with triazole stapling: influence on stability and bioactivity*, J Pept Sci. 23(11):824-832 (Nov. 2017).
Luong et al., *Mono-substitution effects on antimicrobial activity of stapled heptapeptides*, Arch Pharm Res. 40(6):713-719 (Jun. 2017).
Migon et al., *Hydrocarbon Stapled Antimicrobial Peptides*, The Protein Journal, 37:2-12 (2018).
Stone et al., *Influence of hydrocarbon-stapling on membrane interactions of synthetic antimicrobial peptides*, Bioorg Med Chem. 26(6):1189-1196 (Mar. 2018).
International Preliminary Report on Patentability for Intl. App. No. PCT/US2016/040849, dated Jan. 2, 2018 (14 pages).
Alberts et al., "Bacterial shapes and cell-surface structures: Figure 25-4," Molecular Biology of the Cell—NCBI Bookshelf, 2002, 4th Edition, 1 page.
Alberts et al., "Visualizing Cells," Molecular Biology of the Cell, Chapter 9, 5th Edition, 2007, p. 579-615.
Bechinger, "Structure and functions of channel-forming peptides: magainins, cecropins, melittin and alamethicin," Journal of Membrane Biology, 1997, 156:197-211.

Bird, "Biophysical determinants for cellular uptake of hydrocarbon-stapled peptide helices," Nature Chemical Biology, 2016, 12:845-853.
Bray, "Large-scale manufacture of peptide therapeutics by chemical synthesis," Nature Reviews Drug Discovery, 2003, 2:587-593.
Cho et al., "Buforins: histone H2A-derived antimicrobial peptides from toad stomach," Biochimica et Biophysica Acta, 2009, 1788:1564-1569.
Epand et al., "Molecular mechanisms of membrane targeting antibiotics," Biochimica et Biophysica Acta, 2016, 1858:980-987.
Fuerst et al., "Protein uptake by bacteria: an endocytosis-like process in the planctomycete Gemmata obscuriglobus," Communicative & Integrative Biology, 2010, 3(6):572-575.
Hao et al., "The intracellular mechanism of action on *Escherichia coli* of BF2-A/C, two analogues of the antimicrobial peptide Buforin 2," Journal of microbiology, 2013, 51(2):200-206.
Hilinski et al., "Stitched α-helical peptides via bis ring-closing metathesis," Journal of the American Chemical Society, 2014, 136:12314-12322.
Hilpert et al., "Peptide arrays on cellulose support: SPOT synthesis, a time and cost efficient method for synthesis of large numbers of peptides in a parallel and addressable fashion," Nature Protocols, 2007, 2(6):1333-1349.
Ho et al., "The flexibility in the proline ring couples to the protein backbone," Protein Science, 2005, 14:1011-1018.
Huber et al., "Robust production of a peptide library using methodological synchronization," Protein expression and purification, 2009, 67:139-147.
International Preliminary Report on Patentability in International Application No. PCT/US2017/019953, dated Sep. 4, 2018, 10 pages.
Jermy, "Evolution: Bacterial endocytosis uncovered," Nature Reviews Microbiology, 2010, 8:534.
Kim et al., "Synthesis of all-hydrocarbon stapled α-helical peptides by ring-closing olefin metathesis," Nature Protocols, 2011, 6(6):761-771.
Lau et al., "Peptide stapling techniques based on different macrocyclisation chemistries," Chemical Society Reviews, 2015, 44(1):91-102.
Li et al., "A versatile platform to analyze low-affinity and transient protein-protein interactions in living cells in real time," Cell Reports, 2014, 9:1946-1958.
Liu et al., "Comparative antimicrobial activity and mechanism of action of bovine lactoferricin-derived synthetic peptides," Biometals, 2011, 24:1069-1078.
Lodish et al., "Schematic diagram of typical membrane proteins in a biological membrane," Molecular Cell Biology, 2000, 4th Edition, 1 page.
Lonhienne et al., "Endocytosis-like protein uptake in the bacterium Gemmata obscuriglobus," Proceedings of the National Academy of Sciences, 2010, 107(29):12883-12888.
Maraj et al., "Evaluation of Hemolysis in Patients with Prosthetic Heart Valves," Clin. Cardiol., 1998, 21:387-392.
Steinauer et al., "HOPS-dependent endosomal fusion required for efficient cytosolic delivery of therapeutic peptides and small proteins," Proceedings of the National Academy of Sciences, 2019, 116(2):512-521.
Strahl et al., "Bacterial membranes: structure, domains, and function," Annual Review of Microbiology, 2017, 71:519-538.
Xie et al., "Effect of proline position on the antimicrobial mechanism of buforin II," Peptides, 2011, 32:677-682.
Arnusch et al., "Enhanced membrane pore formation through high-affinity targeted antimicrobial peptides," PLoS One, 2012, 7(6):e39768.
European Extended Search Report in European Patent Application No. 16818936.3, dated Jun. 17, 2019, 17 pages.
Kang et al., "Antimicrobial peptides: therapeutic potentials," Expert review of anti-infective therapy, 2014, 12(12):1477-1486.
Patch et al., "Helical peptoid mimics of magainin-2 amide," Journal of the American Chemical Society, 2003, 125(40):12092-12093.
Sun et al., "Membrane permeability of hydrocarbon-cross-linked peptides," Biophysical journal, 2013, 104(9):1923-1932.

* cited by examiner

```
Magainin II   GIGKFLHSAKKFGKAFVGEIBNS
MagStap 1     GIGKFLXAAKKFAXAFVAEIBNS
MagStap 2     GIGKFLHXAKKFAKXFVAEIBNS
MagStap 3     GIGKFLHAXKKFAKAXVAEIBNS
MagStap 4     GIGKFLHAAXKFAKAFXAEIBNS
MagStap 5     GIGKFLHAAKXFAKAFVXEIBNS
MagStap 6     GIGKFLHAAKKXAKAFVAXIBNS
MagStap 7     GIGKFLHAAKKFXKAFVAEXBNS
```

```
Pexiganan    GIGKFLKKAKKFGKAFVKILKK
PexStap 2    GIGKFLKXAKKFGKXFVKILKK
PexStap 5    GIGKFLKKAKXFGKAFVXILKK
PexStap 6    GIGKFLKKAKKXGKAFVKXLKK
```

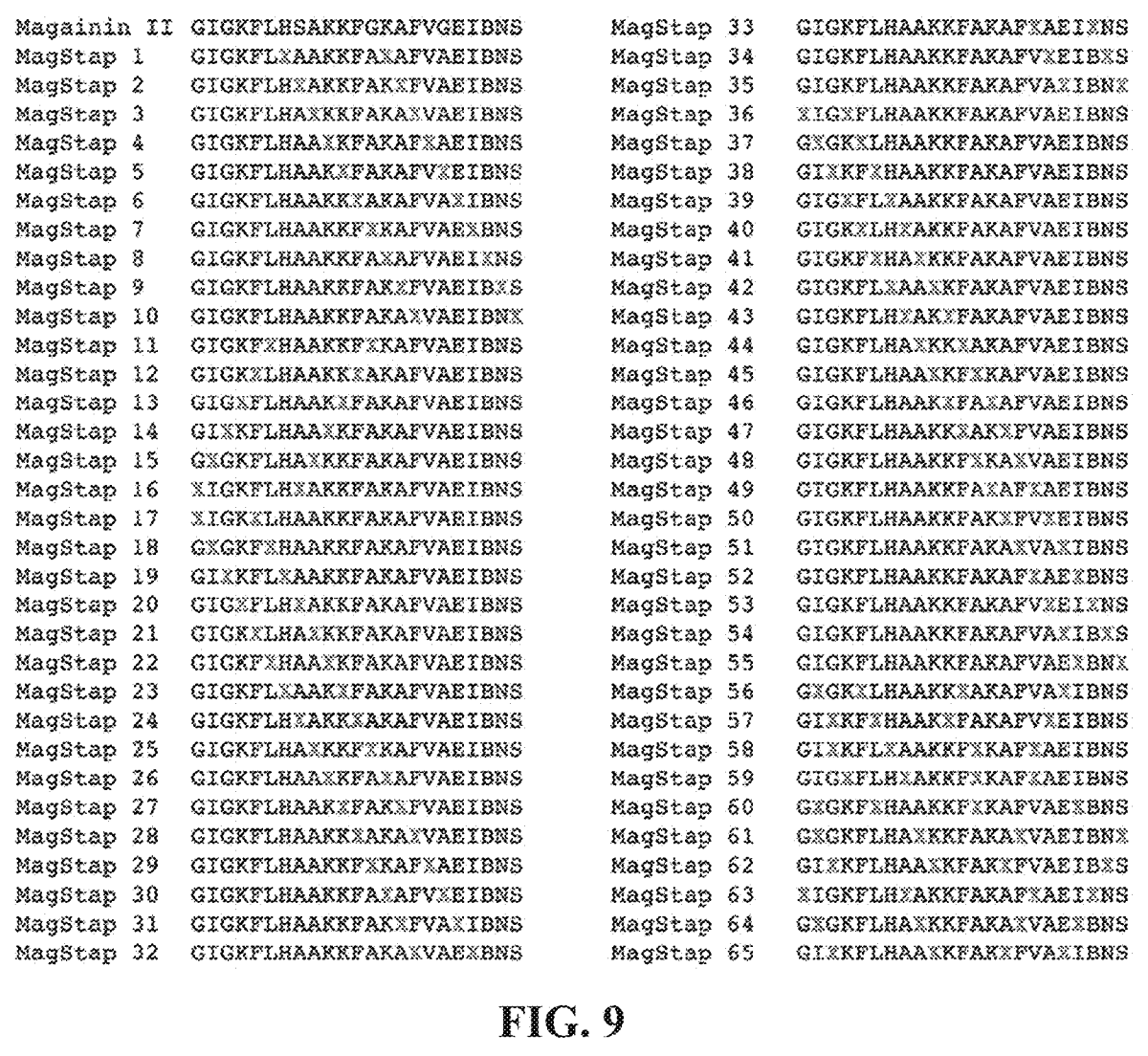

| | | | |
|---|---|---|---|
| Magainin II | GIGKFLHSAKKFGKAFVGEIBNS | | |
| MagStap 1 | GIGKFLXAAKKFAKAFVAEIBNS | MagStap 33 | GIGKFLHAAKKFAKAFXAEIXNS |
| MagStap 2 | GIGKFLHAAKKFAKXFVAEIBNS | MagStap 34 | GIGKFLHAAKKFAKAFXAEIBXS |
| MagStap 3 | GIGKFLHAXKKFAKAXVAEIBNS | MagStap 35 | GIGKFLHAAKKFAKAFXAEIB

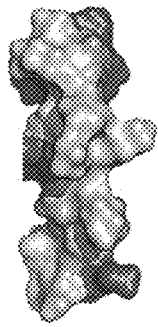
FIG. 15A       FIG. 15B       FIG. 15C
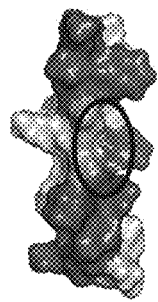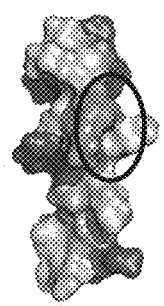
FIG. 15D       FIG. 15E       FIG. 15F

```
Mag(i+4)15(S23K)  GIGKFLHSAKKFGKAXVGEXBNK
Mag(i+4)15(N22K)  GIGKFLHSAKKFGKAXVGEXBKS
Mag(i+4)15(B21K)  GIGKFLHSAKKFGKAXVGEXKNS
Mag(i+4)15(E19K)  GIGKFLHSAKKFGKAXVGKXBNS
Mag(i+4)15(G18K)  GIGKFLHSAKKFGKAXVKEXBNS
Mag(i+4)15(V17K)  GIGKFLHSAKKFGKAXKGEXBNS
Mag(i+4)15(A15K)  GIGKFLHSAKKFGKKXVGEXBNS
Mag(i+4)15(G13K)  GIGKFLHSAKKFKKAXVGEXBNS
Mag(i+4)15(F12K)  GIGKFLHSAKKKGKAXVGEXBNS
Mag(i+4)15(A9K)   GIGKFLHSKKKFGKAXVGEXBNS
Mag(i+4)15(S8K)   GIGKFLHKAKKFGKAXVGEXBNS
Mag(i+4)15(H7K)   GIGKFLKSAKKFGKAXVGEXBNS
Mag(i+4)15(L6K)   GIGKFKHSAKKFGKAXVGEXBNS
Mag(i+4)15(F5K)   GIGKKLHSAKKFGKAXVGEXBNS
Mag(i+4)15(G3K)   GIKKFLHSAKKFGKAXVGEXBNS
Mag(i+4)15(I2K)   GKGKFLHSAKKFGKAXVGEXBNS
Mag(i+4)15(G1K)   KIGKFLHSAKKFGKAXVGEXBNS
```

FIG. 17

| | |
|---|---|
| Mag(i+4)15(G1E) | EIGKFLHSAKKFGKAXVGEXBNS |
| Mag(i+4)15(I2E) | GEGKFLHSAKKFGKAXVGEXBNS |
| Mag(i+4)15(G3E) | GIEKFLHSAKKFGKAXVGEXBNS |
| Mag(i+4)15(K4E) | GIGEFLHSAKKFGKAXVGEXBNS |
| Mag(i+4)15(F5E) | GIGKELHSAKKFGKAXVGEXBNS |
| Mag(i+4)15(L6E) | GIGKFEHSAKKFGKAXVGEXBNS |
| Mag(i+4)15(H7E) | GIGKFLESAKKFGKAXVGEXBNS |
| Mag(i+4)15(S8E) | GIGKFLHEAKKFGKAXVGEXBNS |
| Mag(i+4)15(A9E) | GIGKFLHSEKKFGKAXVGEXBNS |
| Mag(i+4)15(K10E) | GIGKFLHSAEKFGKAXVGEXBNS |
| Mag(i+4)15(K11E) | GIGKFLHSAKEFGKAXVGEXBNS |
| Mag(i+4)15(F12E) | GIGKFLHSAKKEGKAXVGEXBNS |
| Mag(i+4)15(G13E) | GIGKFLHSAKKFEKAXVGEXBNS |
| Mag(i+4)15(K14E) | GIGKFLHSAKKFGEAXVGEXBNS |
| Mag(i+4)15(A15E) | GIGKFLHSAKKFGKEXVGEXBNS |
| Mag(i+4)15(V17E) | GIGKFLHSAKKFGKAXEGEXBNS |
| Mag(i+4)15(G18E) | GIGKFLHSAKKFGKAXVEEXBNS |
| Mag(i+4)15(B21E) | GIGKFLHSAKKFGKAXVGEXENS |
| Mag(i+4)15(N22E) | GIGKFLHSAKKFGKAXVGEXBES |
| Mag(i+4)15(S23E) | GIGKFLHSAKKFGKAXVGEXBNE |

FIG. 18

| | |
|---|---|
| Mag(i+4)15(G3H) | GIHKFLHSAKKFGKAXVGEXBNS |
| Mag(i+4)15(S8H) | GIGKFLHHAKKFGKAXVGEXBNS |
| Mag(i+4)15(A15H) | GIGKFLHSAKKFGKHXVGEXBNS |
| Mag(i+4)15(G18H) | GIGKFLHSAKKFGKAXVHEXBNS |
| | |
| Mag(i+4)15(G13!) | GIGKFLHSAKKF!KAXVGEXBNS |
| Mag(i+4)15(G13P) | GIGKFLHSAKKFPKAXVGEXBNS |
| Mag(i+4)15(G13&) | GIGKFLHSAKKF&KAXVGEXBNS |
| Mag(i+4)15(G13A) | GIGKFLHSAKKFAKAXVGEXBNS |
| Mag(i+4)15(G13a) | GIGKFLHSAKKFaKAXVGEXBNS |
| Mag(i+4)15(G13k) | GIGKFLHSAKKFkKAXVGEXBNS |

FIG. 19

Mag(i+4)2,15(I2K,A9K,G18H)       GKXKFLXSKKKFGKAXVHEXBNS
Mag(i+4)2,15(I2K,A9H)            GKXKFLXSHKKFGKAXVGEXBNS
Mag(i+4)2,15(I2K,A9H,N21E)       GKXKFLXSHKKFGKAXVGEXBES
Mag(i+4)2,15(I2K,A9H,G18H,N21E)  GKXKFLXSHKKFGKAXVHEXBES
Mag(i+4)1,15(S8H,A9K,G18H,N21E)  GXGKFXHSKKKFGKAXVHEXBES

Pleurocidin-NH2     GWGSFFKKAAHVGKHVGKAALTHYL
Pleu(i+4)1,15       GXGSFXKKAAHVGKHXGKAXLTHYL
Pleu(i+4)1,15(A9K)  GXGSFXKKKAHVGKHXGKAXLTHYL

SEQUENCE LISTING

```
<160> NUMBER OF SEQ ID NOS: 262

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser or Ala
<220> FEATURE:
<221> NAME/KEY: MOD_RES
<222> LOCATION: (13)..(13)
<223> OTHER INFORMATION: Ala or Gly
<220> FEATURE:
<221> NAME/KEY: MOD_RES
<222> LOCATION: (18)..(18)
<223> OTHER INFORMATION: Ala or Gly

<400> SEQUENCE: 1

Gly Ile Gly Lys Phe Leu His Xaa Ala Lys Lys Phe Xaa Lys Ala Phe
1               5                   10                  15

Val Xaa Glu Ile Met Asn Ser
            20

<210> SEQ ID NO 2
<211> LENGTH: 22
<212> TYPE: PRT
<213> ORGANISM: Unknown
<220> FEATURE:
<223> OTHER INFORMATION: Description of Unknown:
      Pexiganan peptide

<400> SEQUENCE: 2

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 3
<211> LENGTH: 23
<212> TYPE: PRT
<213> ORGANISM: Unknown
<220> FEATURE:
<223> OTHER INFORMATION: Description of Unknown:
      Magainin peptide
```

```
<400> SEQUENCE: 3

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 4
<211> LENGTH: 25
<212> TYPE: PRT
<213> ORGANISM: Pseudopleuronectes americanus

<400> SEQUENCE: 4

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 5
<211> LENGTH: 33
<212> TYPE: PRT
<213> ORGANISM: Pardachirus marmoratus

<400> SEQUENCE: 5

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 6
<211> LENGTH: 32
<212> TYPE: PRT
<213> ORGANISM: Myxine glutinosa

<400> SEQUENCE: 6

Gly Phe Phe Lys Lys Ala Trp Arg Lys Val Lys His Ala Gly Arg Arg
1               5                   10                  15

Val Leu Lys Lys Gly Val Gly Arg His Tyr Val Asn Asn Trp Leu Lys
            20                  25                  30

<210> SEQ ID NO 7
<211> LENGTH: 24
<212> TYPE: PRT
<213> ORGANISM: Xenopus laevis

<400> SEQUENCE: 7

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 8
<211> LENGTH: 21
<212> TYPE: PRT
<213> ORGANISM: Bufo gargarizans

<400> SEQUENCE: 8

Thr Arg Ser Ser Arg Ala Gly Leu Gln Phe Pro Val Gly Arg Val His
1               5                   10                  15

Arg Leu Leu Arg Lys
```

```
                        20

<210> SEQ ID NO 9
<211> LENGTH: 34
<212> TYPE: PRT
<213> ORGANISM: Phyllomedusa sp.

<400> SEQUENCE: 9

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 10
<211> LENGTH: 25
<212> TYPE: PRT
<213> ORGANISM: Litoria chloris

<400> SEQUENCE: 10

Gly Leu Phe Lys Val Leu Gly Ser Val Ala Lys His Leu Leu Pro His
1               5                   10                  15

Val Val Pro Val Ile Ala Glu Lys Leu
            20                  25

<210> SEQ ID NO 11
<211> LENGTH: 26
<212> TYPE: PRT
<213> ORGANISM: Unknown
<220> FEATURE:
<223> OTHER INFORMATION: Description of Unknown:
      Melittin peptide

<400> SEQUENCE: 11

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 12
<211> LENGTH: 37
<212> TYPE: PRT
<213> ORGANISM: Unknown
<220> FEATURE:
<223> OTHER INFORMATION: Description of Unknown:
      Cecropin A polypeptide

<400> SEQUENCE: 12

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 13
<211> LENGTH: 27
<212> TYPE: PRT
<213> ORGANISM: Unknown
<220> FEATURE:
<223> OTHER INFORMATION: Description of Unknown:
      Lycotoxin I peptide

<400> SEQUENCE: 13
```

```
Lys Ile Lys Trp Phe Lys Thr Met Lys Ser Ile Ala Lys Phe Ile Ala
1               5                   10                  15

Lys Glu Gln Met Lys Lys His Leu Gly Gly Glu
                20                  25

<210> SEQ ID NO 14
<211> LENGTH: 19
<212> TYPE: PRT
<213> ORGANISM: Unknown
<220> FEATURE:
<223> OTHER INFORMATION: Description of Unknown:
      Styelins B peptide

<400> SEQUENCE: 14

Gly Phe Gly Pro Ala Phe His Ser Val Ser Asn Phe Ala Lys Lys His
1               5                   10                  15

Lys Thr Ala

<210> SEQ ID NO 15
<211> LENGTH: 23
<212> TYPE: PRT
<213> ORGANISM: Unknown
<220> FEATURE:
<223> OTHER INFORMATION: Description of Unknown:
      Clavanin B peptide

<400> SEQUENCE: 15

Val Phe Gln Phe Leu Gly Arg Ile Ile His His Val Gly Asn Phe Val
1               5                   10                  15

His Gly Phe Ser His Val Phe
                20

<210> SEQ ID NO 16
<211> LENGTH: 13
<212> TYPE: PRT
<213> ORGANISM: Unknown
<220> FEATURE:
<223> OTHER INFORMATION: Description of Unknown:
      Cathelicidin A peptide

<400> SEQUENCE: 16

Ile Leu Lys Lys Trp Pro Trp Trp Pro Trp Arg Arg Lys
1               5                   10

<210> SEQ ID NO 17
<211> LENGTH: 48
<212> TYPE: PRT
<213> ORGANISM: Unknown
<220> FEATURE:
<223> OTHER INFORMATION: Description of Unknown:
      Dermcidin polypeptide

<400> SEQUENCE: 17

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
                20                  25                  30

Gly Lys Gly Ala Val His Asp Val Lys Asp Val Leu Asp Ser Val Leu
            35                  40                  45

<210> SEQ ID NO 18
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple

<400> SEQUENCE: 18

Gly Trp Gly Ser Phe Phe Lys Lys Ala Ala His Xaa Gly Lys His Val
1               5                   10                  15

Gly Lys Xaa Ala Leu Thr His Tyr Leu
            20                  25

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple

<400> SEQUENCE: 19

Gly Phe Phe Ala Leu Ile Pro Lys Ile Ile Ser Xaa Pro Leu Phe Lys
1               5                   10                  15

Thr Leu Xaa Ser Ala Val Gly Ser Ala Leu Ser Ser Ser Gly Glu Gln
            20                  25                  30

Glu

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Brominated Trp
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple
<220> FEATURE:
<221> NAME/KEY: MOD_RES
<222> LOCATION: (30)..(30)
<223> OTHER INFORMATION: Brominated Trp

<400> SEQUENCE: 20
```

```
Gly Phe Phe Lys Lys Ala Trp Arg Lys Val Lys His Ala Xaa Arg Arg
1               5                   10                  15

Val Leu Lys Lys Xaa Val Gly Arg His Tyr Val Asn Asn Trp Leu Lys
            20                  25                  30
```

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 21

```
Gly Val Leu Ser Asn Val Ile Gly Tyr Leu Lys Lys Leu Xaa Thr Gly
1               5                   10                  15

Ala Leu Asn Ala Xaa Leu Lys Gln
            20
```

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple

<400> SEQUENCE: 22

```
Thr Arg Ser Ser Arg Ala Gly Leu Gln Phe Pro Xaa Gly Arg Val His
1               5                   10                  15

Arg Leu Xaa Arg Lys
            20
```

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 23

Ala Leu Trp Lys Thr Met Leu Lys Lys Leu Gly Thr Met Xaa Leu His
1               5                   10                  15

Ala Gly Lys Ala Xaa Leu Gly Ala Ala Ala Asp Thr Ile Ser Gln Gly
            20                  25                  30

Thr Gln

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 24

Gly Leu Phe Lys Val Leu Gly Ser Val Ala Lys His Leu Xaa Pro His
1               5                   10                  15

Val Val Pro Val Xaa Ala Glu Lys Leu
            20                  25

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple

<400> SEQUENCE: 25

Gly Ile Gly Ala Val Leu Lys Val Leu Thr Thr Gly Xaa Pro Ala Leu
1               5                   10                  15

Ile Ser Trp Xaa Lys Arg Lys Arg Gln Gln
            20                  25

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:

<221> NAME/KEY: MOD_RES
<222> LOCATION: (11)..(11)
<223> OTHER INFORMATION: Any amino acid whose side chain has been
      replaced by an internal staple

<400> SEQUENCE: 26

Lys Trp Lys Xaa Phe Lys Lys Ile Glu Lys Xaa Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple

<400> SEQUENCE: 27

Lys Ile Lys Trp Phe Lys Thr Xaa Lys Ser Ile Ala Lys Phe Xaa Ala
1               5                   10                  15

Lys Glu Gln Met Lys Lys His Leu Gly Gly Glu
            20                  25

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple

<400> SEQUENCE: 28

Gly Phe Gly Pro Xaa Phe His Ser Val Ser Asn Xaa Ala Lys Lys His
1               5                   10                  15

Lys Thr Ala

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES -continued

```
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple

<400> SEQUENCE: 29

Val Phe Gln Phe Xaa Gly Arg Ile Ile His His Xaa Gly Asn Phe Val
1               5                   10                  15

His Gly Phe Ser His Val Phe
            20

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple

<400> SEQUENCE: 30

Ile Xaa Lys Lys Trp Pro Trp Trp Xaa Trp Arg Arg Lys
1               5                   10

<210> SEQ ID NO 31
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple

<400> SEQUENCE: 31

Ser Ser Leu Leu Glu Lys Gly Leu Asp Gly Xaa Lys Lys Ala Val Gly
1               5                   10                  15

Gly Xaa Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 32

Gly Ile Gly Lys Phe Leu His Ser Ala Lys Lys Phe Gly Lys Ala Xaa
1               5                   10                  15

Val Gly Glu Xaa Xaa Asn Lys
            20

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 33

Gly Ile Gly Lys Phe Leu His Ser Ala Lys Lys Phe Gly Lys Ala Xaa
1               5                   10                  15

Val Gly Glu Xaa Xaa Lys Ser
            20

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple

<400> SEQUENCE: 34

Gly Ile Gly Lys Phe Leu His Ser Ala Lys Lys Phe Gly Lys Ala Xaa
1               5                   10                  15

Val Gly Glu Xaa Lys Asn Ser

```
<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 35

Gly Ile Gly Lys Phe Leu His Ser Ala Lys Lys Phe Gly Lys Ala Xaa
1               5                   10                  15

Val Gly Lys Xaa Xaa Asn Ser
            20

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 36

Gly Ile Gly Lys Phe Leu His Ser Ala Lys Lys Phe Gly Lys Ala Xaa
1               5                   10                  15

Val Lys Glu Xaa Xaa Asn Ser
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
```

```
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 37

Gly Ile Gly Lys Phe Leu His Ser Ala Lys Lys Phe Gly Lys Ala Xaa
1               5                   10                  15

Lys Gly Glu Xaa Xaa Asn Ser
            20

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 38

Gly Ile Gly Lys Phe Leu His Ser Ala Lys Lys Phe Gly Lys Lys Xaa
1               5                   10                  15

Val Gly Glu Xaa Xaa Asn Ser
            20

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 39

Gly Ile Gly Lys Phe Leu His Ser Ala Lys Lys Phe Lys Lys Ala Xaa
1               5                   10                  15

Val Gly Glu Xaa Xaa Asn Ser
            20
```

```
<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 40

Gly Ile Gly Lys Phe Leu His Ser Ala Lys Lys Gly Lys Ala Xaa
1               5                   10                  15

Val Gly Glu Xaa Xaa Asn Ser
            20

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 41

Gly Ile Gly Lys Phe Leu His Ser Lys Lys Lys Phe Gly Lys Ala Xaa
1               5                   10                  15

Val Gly Glu Xaa Xaa Asn Ser
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
```

```
<220> FEATURE:
<221> NAME/KEY: MOD_RES
<222> LOCATION: (21)..(21)
<223> OTHER INFORMATION: Norleucine

<400> SEQUENCE: 42

Gly Ile Gly Lys Phe Leu His Lys Ala Lys Lys Phe Gly Lys Ala Xaa
1               5                   10                  15

Val Gly Glu Xaa Xaa Asn Ser
            20

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 43

Gly Ile Gly Lys Phe Leu Lys Ser Ala Lys Lys Phe Gly Lys Ala Xaa
1               5                   10                  15

Val Gly Glu Xaa Xaa Asn Ser
            20

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 44

Gly Ile Gly Lys Phe Lys His Ser Ala Lys Lys Phe Gly Lys Ala Xaa
1               5                   10                  15

Val Gly Glu Xaa Xaa Asn Ser
            20

<210> SEQ ID NO 45
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 45

Gly Ile Gly Lys Lys Leu His Ser Ala Lys Lys Phe Gly Lys Ala Xaa
1               5                   10                  15

Val Gly Glu Xaa Xaa Asn Ser
            20

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 46

Gly Ile Lys Lys Phe Leu His Ser Ala Lys Lys Phe Gly Lys Ala Xaa
1               5                   10                  15

Val Gly Glu Xaa Xaa Asn Ser
            20

<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
```

<223> OTHER INFORMATION: Norleucine

<400> SEQUENCE: 47

Gly Lys Gly Lys Phe Leu His Ser Ala Lys Lys Phe Gly Lys Ala Xaa
1               5                   10                  15

Val Gly Glu Xaa Xaa Asn Ser
            20

<210> SEQ ID NO 48
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 48

Lys Ile Gly Lys Phe Leu His Ser Ala Lys Lys Phe Gly Lys Ala Xaa
1               5                   10                  15

Val Gly Glu Xaa Xaa Asn Ser
            20

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 49

Glu Ile Gly Lys Phe Leu His Ser Ala Lys Lys Phe Gly Lys Ala Xaa
1               5                   10                  15

Val Gly Glu Xaa Xaa Asn Ser
            20

<210> SEQ ID NO 50
<211> LENGTH: 23
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 50

Gly Glu Gly Lys Phe Leu His Ser Ala Lys Lys Phe Gly Lys Ala Xaa
1               5                   10                  15

Val Gly Glu Xaa Xaa Asn Ser
            20

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 51

Gly Ile Glu Lys Phe Leu His Ser Ala Lys Lys Phe Gly Lys Ala Xaa
1               5                   10                  15

Val Gly Glu Xaa Xaa Asn Ser
            20

<210> SEQ ID NO 52
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 52
```

Gly Ile Gly Glu Phe Leu His Ser Ala Lys Lys Phe Gly Lys Ala Xaa
1               5                   10                  15

Val Gly Glu Xaa Xaa Asn Ser
            20

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 53

Gly Ile Gly Lys Glu Leu His Ser Ala Lys Lys Phe Gly Lys Ala Xaa
1               5                   10                  15

Val Gly Glu Xaa Xaa Asn Ser
            20

<210> SEQ ID NO 54
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 54

Gly Ile Gly Lys Phe Glu His Ser Ala Lys Lys Phe Gly Lys Ala Xaa
1               5                   10                  15

Val Gly Glu Xaa Xaa Asn Ser
            20

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 55

Gly Ile Gly Lys Phe Leu Glu Ser Ala Lys Lys Phe Gly Lys Ala Xaa
1               5                   10                  15

Val Gly Glu Xaa Xaa Asn Ser
            20

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 56

Gly Ile Gly Lys Phe Leu His Glu Ala Lys Lys Phe Gly Lys Ala Xaa
1               5                   10                  15

Val Gly Glu Xaa Xaa Asn Ser
            20

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 57

Gly Ile Gly Lys Phe Leu His Ser Glu Lys Lys Phe Gly Lys Ala Xaa
1               5                   10                  15
```

Val Gly Glu Xaa Xaa Asn Ser
            20

<210> SEQ ID NO 58
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 58

Gly Ile Gly Lys Phe Leu His Ser Ala Glu Lys Phe Gly Lys Ala Xaa
1               5                   10                  15

Val Gly Glu Xaa Xaa Asn Ser
            20

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 59

Gly Ile Gly Lys Phe Leu His Ser Ala Lys Glu Phe Gly Lys Ala Xaa
1               5                   10                  15

Val Gly Glu Xaa Xaa Asn Ser
            20

<210> SEQ ID NO 60
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple -continued

```
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 60

Gly Ile Gly Lys Phe Leu His Ser Ala Lys Lys Glu Gly Lys Ala Xaa
1               5                   10                  15

Val Gly Glu Xaa Xaa Asn Ser
            20

<210> SEQ ID NO 61
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 61

Gly Ile Gly Lys Phe Leu His Ser Ala Lys Lys Phe Glu Lys Ala Xaa
1               5                   10                  15

Val Gly Glu Xaa Xaa Asn Ser
            20

<210> SEQ ID NO 62
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 62

Gly Ile Gly Lys Phe Leu His Ser Ala Lys Lys Phe Gly Glu Ala Xaa
1               5                   10                  15

Val Gly Glu Xaa Xaa Asn Ser
            20
```

-continued

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 63

Gly Ile Gly Lys Phe Leu His Ser Ala Lys Lys Phe Gly Lys Glu Xaa
1               5                   10                  15

Val Gly Glu Xaa Xaa Asn Ser
            20

<210> SEQ ID NO 64
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 64

Gly Ile Gly Lys Phe Leu His Ser Ala Lys Lys Phe Gly Lys Ala Xaa
1               5                   10                  15

Glu Gly Glu Xaa Xaa Asn Ser
            20

<210> SEQ ID NO 65
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)

```
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 65

Gly Ile Gly Lys Phe Leu His Ser Ala Lys Lys Phe Gly Lys Ala Xaa
1               5                   10                  15

Val Glu Glu Xaa Xaa Asn Ser
            20

<210> SEQ ID NO 66
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple

<400> SEQUENCE: 66

Gly Ile Gly Lys Phe Leu His Ser Ala Lys Lys Phe Gly Lys Ala Xaa
1               5                   10                  15

Val Gly Glu Xaa Glu Asn Ser
            20

<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 67

Gly Ile Gly Lys Phe Leu His Ser Ala Lys Lys Phe Gly Lys Ala Xaa
1               5                   10                  15

Val Gly Glu Xaa Xaa Glu Ser
            20

<210> SEQ ID NO 68
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 68

Gly Ile Gly Lys Phe Leu His Ser Ala Lys Lys Phe Gly Lys Ala Xaa
1               5                   10                  15

Val Gly Glu Xaa Xaa Asn Glu
            20

<210> SEQ ID NO 69
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 69

Xaa Ile Gly Lys Xaa Leu His Ser Ala Lys Lys Phe Gly Lys Ala Phe
1               5                   10                  15

Val Gly Glu Ile Xaa Asn Ser
            20

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple
```

<400> SEQUENCE: 70

Gly Ile Gly Lys Phe Leu His Ser Ala Lys Lys Phe Gly Lys Ala Phe
1               5                   10                  15

Val Gly Xaa Ile Xaa Asn Xaa
            20

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 71

Gly Xaa Gly Lys Phe Xaa His Ser Lys Lys Lys Phe Gly Lys Ala Xaa
1               5                   10                  15

Val Gly Glu Xaa Xaa Asn Ser
            20

<210> SEQ ID NO 72
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 72

Gly Ile Xaa Lys Phe Leu Xaa Ser Lys Lys Phe Gly Lys Ala Xaa
1               5                   10                  15

Val Gly Glu Xaa Xaa Asn Ser
            20

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 73

Gly Ile His Lys Phe Leu His Ser Ala Lys Lys Phe Gly Lys Ala Xaa
1               5                   10                  15

Val Gly Glu Xaa Xaa Asn Ser
            20

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 74

Gly Ile Gly Lys Phe Leu His His Ala Lys Lys Phe Gly Lys Ala Xaa
1               5                   10                  15

Val Gly Glu Xaa Xaa Asn Ser
            20

<210> SEQ ID NO 75
<211> LENGTH: 23
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 75

Gly Ile Gly Lys Phe Leu His Ser Ala Lys Lys Phe Gly Lys His Xaa
1               5                   10                  15

Val Gly Glu Xaa Xaa Asn Ser
            20

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 76

Gly Ile Gly Lys Phe Leu His Ser Ala Lys Lys Phe Gly Lys Ala Xaa
1               5                   10                  15

Val His Glu Xaa Xaa Asn Ser
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 2-aminoisobutyric acid
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
```

```
<221> NAME/KEY: MOD_RES
<222> LOCATION: (21)..(21)
<223> OTHER INFORMATION: Norleucine

<400> SEQUENCE: 77

Gly Ile Gly Lys Phe Leu His Ser Ala Lys Lys Phe Xaa Lys Ala Xaa
1               5                   10                  15

Val Gly Glu Xaa Xaa Asn Ser
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 78

Gly Ile Gly Lys Phe Leu His Ser Ala Lys Lys Phe Pro Lys Ala Xaa
1               5                   10                  15

Val Gly Glu Xaa Xaa Asn Ser
            20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 79

Gly Ile Gly Lys Phe Leu His Ser Ala Lys Lys Phe Xaa Lys Ala Xaa
1               5                   10                  15

Val Gly Glu Xaa Xaa Asn Ser
            20
```

```
<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 80

Gly Ile Gly Lys Phe Leu His Ser Ala Lys Lys Phe Ala Lys Ala Xaa
1               5                   10                  15

Val Gly Glu Xaa Xaa Asn Ser
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: D-Alanine
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 81

Gly Ile Gly Lys Phe Leu His Ser Ala Lys Lys Phe Xaa Lys Ala Xaa
1               5                   10                  15

Val Gly Glu Xaa Xaa Asn Ser
            20

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: D-Lysine
<220> FEATURE:
<221> NAME/KEY: MOD_RES
```

```
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 82

Gly Ile Gly Lys Phe Leu His Ser Ala Lys Lys Phe Xaa Lys Ala Xaa
1               5                   10                  15

Val Gly Glu Xaa Xaa Asn Ser
            20

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 83

Gly Ile Gly Lys Phe Leu His Ser Ala Lys Xaa Phe Gly Lys Ala Phe
1               5                   10                  15

Val Xaa Glu Ile Xaa Asn Lys
            20

<210> SEQ ID NO 84
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 84

Gly Ile Gly Lys Phe Leu His Ser Ala Lys Xaa Phe Gly Lys Ala Phe
1               5                   10                  15
```

```
Val Xaa Glu Ile Xaa Lys Ser
            20

<210> SEQ ID NO 85
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple

<400> SEQUENCE: 85

Gly Ile Gly Lys Phe Leu His Ser Ala Lys Xaa Phe Gly Lys Ala Phe
1               5                   10                  15

Val Xaa Glu Ile Lys Asn Ser
            20

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 86

Gly Ile Gly Lys Phe Leu His Ser Ala Lys Xaa Phe Gly Lys Ala Phe
1               5                   10                  15

Val Xaa Glu Lys Xaa Asn Ser
            20

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
``` replaced by an internal staple
<220> FEATURE:
<221> NAME/KEY: MOD_RES
<222> LOCATION: (21)..(21)
<223> OTHER INFORMATION: Norleucine

<400> SEQUENCE: 87

Gly Ile Gly Lys Phe Leu His Ser Ala Lys Xaa Phe Gly Lys Ala Phe
1               5                   10                  15

Val Xaa Lys Ile Xaa Asn Ser
            20

<210> SEQ ID NO 88
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 88

Gly Ile Gly Lys Phe Leu His Ser Ala Lys Xaa Phe Gly Lys Ala Phe
1               5                   10                  15

Lys Xaa Glu Ile Xaa Asn Ser
            20

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 89

Gly Ile Gly Lys Phe Leu His Ser Ala Lys Xaa Phe Gly Lys Ala Lys
1               5                   10                  15

Val Xaa Glu Ile Xaa Asn Ser
            20

<210> SEQ ID NO 90
<211> LENGTH: 23

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 90

Gly Ile Gly Lys Phe Leu His Ser Ala Lys Xaa Phe Gly Lys Lys Phe
1               5                   10                  15

Val Xaa Glu Ile Xaa Asn Ser
            20

<210> SEQ ID NO 91
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 91

Gly Ile Gly Lys Phe Leu His Ser Ala Lys Xaa Phe Lys Lys Ala Phe
1               5                   10                  15

Val Xaa Glu Ile Xaa Asn Ser
            20

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
```

```
<222> LOCATION: (21)..(21)
<223> OTHER INFORMATION: Norleucine

<400> SEQUENCE: 92

Gly Ile Gly Lys Phe Leu His Ser Ala Lys Xaa Lys Gly Lys Ala Phe
1               5                   10                  15

Val Xaa Glu Ile Xaa Asn Ser
            20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 93

Gly Ile Gly Lys Phe Leu His Ser Lys Lys Xaa Phe Gly Lys Ala Phe
1               5                   10                  15

Val Xaa Glu Ile Xaa Asn Ser
            20

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 94

Gly Ile Gly Lys Phe Leu His Lys Ala Lys Xaa Phe Gly Lys Ala Phe
1               5                   10                  15

Val Xaa Glu Ile Xaa Asn Ser
            20

<210> SEQ ID NO 95
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 95

Gly Ile Gly Lys Phe Leu Lys Ser Ala Lys Xaa Phe Gly Lys Ala Phe
1               5                   10                  15

Val Xaa Glu Ile Xaa Asn Ser
            20

<210> SEQ ID NO 96
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 96

Gly Ile Gly Lys Phe Lys His Ser Ala Lys Xaa Phe Gly Lys Ala Phe
1               5                   10                  15

Val Xaa Glu Ile Xaa Asn Ser
            20

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
```

-continued

<400> SEQUENCE: 97

Gly Ile Gly Lys Lys Leu His Ser Ala Lys Xaa Phe Gly Lys Ala Phe
1               5                   10                  15

Val Xaa Glu Ile Xaa Asn Ser
            20

<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 98

Gly Ile Lys Lys Phe Leu His Ser Ala Lys Xaa Phe Gly Lys Ala Phe
1               5                   10                  15

Val Xaa Glu Ile Xaa Asn Ser
            20

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 99

Gly Lys Gly Lys Phe Leu His Ser Ala Lys Xaa Phe Gly Lys Ala Phe
1               5                   10                  15

Val Xaa Glu Ile Xaa Asn Ser
            20

<210> SEQ ID NO 100
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 100

Lys Ile Gly Lys Phe Leu His Ser Ala Lys Xaa Phe Gly Lys Ala Phe
1               5                   10                  15

Val Xaa Glu Ile Xaa Asn Ser
            20

<210> SEQ ID NO 101
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 101

Glu Ile Gly Lys Phe Leu His Ser Ala Lys Xaa Phe Gly Lys Ala Phe
1               5                   10                  15

Val Xaa Glu Ile Xaa Asn Ser
            20

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 102

Gly Glu Gly Lys Phe Leu His Ser Ala Lys Xaa Phe Gly Lys Ala Phe
```

```
1               5                   10                  15

Val Xaa Glu Ile Xaa Asn Ser
            20

<210> SEQ ID NO 103
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 103

Gly Ile Glu Lys Phe Leu His Ser Ala Lys Xaa Phe Gly Lys Ala Phe
1               5                   10                  15

Val Xaa Glu Ile Xaa Asn Ser
            20

<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 104

Gly Ile Gly Glu Phe Leu His Ser Ala Lys Xaa Phe Gly Lys Ala Phe
1               5                   10                  15

Val Xaa Glu Ile Xaa Asn Ser
            20

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
```

-continued replaced by an internal staple
<220> FEATURE:
<221> NAME/KEY: MOD_RES
<222> LOCATION: (18)..(18)
<223> OTHER INFORMATION: Any amino acid whose side chain has been
       replaced by an internal staple
<220> FEATURE:
<221> NAME/KEY: MOD_RES
<222> LOCATION: (21)..(21)
<223> OTHER INFORMATION: Norleucine

<400> SEQUENCE: 105

Gly Ile Gly Lys Glu Leu His Ser Ala Lys Xaa Phe Gly Lys Ala Phe
1               5                   10                  15

Val Xaa Glu Ile Xaa Asn Ser
            20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (11)..(11)
<223> OTHER INFORMATION: Any amino acid whose side chain has been
       replaced by an internal staple
<220> FEATURE:
<221> NAME/KEY: MOD_RES
<222> LOCATION: (18)..(18)
<223> OTHER INFORMATION: Any amino acid whose side chain has been
       replaced by an internal staple
<220> FEATURE:
<221> NAME/KEY: MOD_RES
<222> LOCATION: (21)..(21)
<223> OTHER INFORMATION: Norleucine

<400> SEQUENCE: 106

Gly Ile Gly Lys Phe Glu His Ser Ala Lys Xaa Phe Gly Lys Ala Phe
1               5                   10                  15

Val Xaa Glu Ile Xaa Asn Ser
            20

<210> SEQ ID NO 107
<211> LENGTH: 23
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (11)..(11)
<223> OTHER INFORMATION: Any amino acid whose side chain has been
       replaced by an internal staple
<220> FEATURE:
<221> NAME/KEY: MOD_RES
<222> LOCATION: (18)..(18)
<223> OTHER INFORMATION: Any amino acid whose side chain has been
       replaced by an internal staple
<220> FEATURE:
<221> NAME/KEY: MOD_RES
<222> LOCATION: (21)..(21)
<223> OTHER INFORMATION: Norleucine

<400> SEQUENCE: 107

Gly Ile Gly Lys Phe Leu Glu Ser Ala Lys Xaa Phe Gly Lys Ala Phe
1               5                   10                  15

Val Xaa Glu Ile Xaa Asn Ser

-continued

```
              20

<210> SEQ ID NO 108
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 108

Gly Ile Gly Lys Phe Leu His Glu Ala Lys Xaa Phe Gly Lys Ala Phe
1               5                  10                  15

Val Xaa Glu Ile Xaa Asn Ser
            20

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 109

Gly Ile Gly Lys Phe Leu His Ser Glu Lys Xaa Phe Gly Lys Ala Phe
1               5                  10                  15

Val Xaa Glu Ile Xaa Asn Ser
            20

<210> SEQ ID NO 110
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
```

```
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 110

Gly Ile Gly Lys Phe Leu His Ser Ala Glu Xaa Phe Gly Lys Ala Phe
1               5                   10                  15

Val Xaa Glu Ile Xaa Asn Ser
            20

<210> SEQ ID NO 111
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 111

Gly Ile Gly Lys Phe Leu His Ser Ala Lys Xaa Glu Gly Lys Ala Phe
1               5                   10                  15

Val Xaa Glu Ile Xaa Asn Ser
            20

<210> SEQ ID NO 112
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 112

Gly Ile Gly Lys Phe Leu His Ser Ala Lys Xaa Phe Glu Lys Ala Phe
1               5                   10                  15

Val Xaa Glu Ile Xaa Asn Ser
            20
```

```
<210> SEQ ID NO 113
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 113

Gly Ile Gly Lys Phe Leu His Ser Ala Lys Xaa Phe Gly Glu Ala Phe
1               5                   10                  15

Val Xaa Glu Ile Xaa Asn Ser
            20

<210> SEQ ID NO 114
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 114

Gly Ile Gly Lys Phe Leu His Ser Ala Lys Xaa Phe Gly Lys Glu Phe
1               5                   10                  15

Val Xaa Glu Ile Xaa Asn Ser
            20

<210> SEQ ID NO 115
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
```

```
<220> FEATURE:
<221> NAME/KEY: MOD_RES
<222> LOCATION: (21)..(21)
<223> OTHER INFORMATION: Norleucine

<400> SEQUENCE: 115

Gly Ile Gly Lys Phe Leu His Ser Ala Lys Xaa Phe Gly Lys Ala Glu
1               5                   10                  15

Val Xaa Glu Ile Xaa Asn Ser
            20

<210> SEQ ID NO 116
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 116

Gly Ile Gly Lys Phe Leu His Ser Ala Lys Xaa Phe Gly Lys Ala Phe
1               5                   10                  15

Glu Xaa Glu Ile Xaa Asn Ser
            20

<210> SEQ ID NO 117
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 117

Gly Ile Gly Lys Phe Leu His Ser Ala Lys Xaa Phe Gly Lys Ala Phe
1               5                   10                  15

Val Xaa Glu Glu Xaa Asn Ser
            20

<210> SEQ ID NO 118
<211> LENGTH: 23
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple

<400> SEQUENCE: 118

Gly Ile Gly Lys Phe Leu His Ser Ala Lys Xaa Phe Gly Lys Ala Phe
1               5                   10                  15

Val Xaa Glu Ile Glu Asn Ser
            20

<210> SEQ ID NO 119
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 119

Gly Ile Gly Lys Phe Leu His Ser Ala Lys Xaa Phe Gly Lys Ala Phe
1               5                   10                  15

Val Xaa Glu Ile Xaa Glu Ser
            20

<210> SEQ ID NO 120
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 120

```
Gly Ile Gly Lys Phe Leu His Ser Ala Lys Xaa Phe Gly Lys Ala Phe
1               5                   10                  15

Val Xaa Glu Ile Xaa Asn Glu
            20
```

<210> SEQ ID NO 121
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 121

```
Gly Ile Gly Lys Phe Leu His Ser Ala Lys Lys Phe Gly Lys Ala Xaa
1               5                   10                  15

Val Gly Glu Ile Xaa Asn Xaa
            20
```

<210> SEQ ID NO 122
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 122

```
Xaa Ile Gly Lys Phe Leu His Xaa Ala Lys Lys Phe Gly Lys Ala Phe
1               5                   10                  15

Val Gly Glu Ile Xaa Asn Ser
            20
```

<210> SEQ ID NO 123
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 123

Gly Xaa Gly Lys Phe Xaa His Ser Lys Lys Xaa Phe Gly Lys Ala Phe
1               5                   10                  15

Val Xaa Glu Ile Xaa Asn Ser
            20

<210> SEQ ID NO 124
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 124

Gly Ile Xaa Lys Phe Leu Xaa Ser Lys Lys Xaa Phe Gly Lys Ala Phe
1               5                   10                  15

Val Xaa Glu Ile Xaa Asn Ser
            20

<210> SEQ ID NO 125
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 125

Gly Ile His Lys Phe Leu His Ser Ala Lys Xaa Phe Gly Lys Ala Phe
1               5                   10                  15

Val Xaa Glu Ile Xaa Asn Ser
            20

<210> SEQ ID NO 126
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 126

Gly Ile Gly Lys Phe Leu His His Ala Lys Xaa Phe Gly Lys Ala Phe
1               5                   10                  15

Val Xaa Glu Ile Xaa Asn Ser
            20

<210> SEQ ID NO 127
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 127
```

Gly Ile Gly Lys Phe Leu His Ser Ala Lys Xaa Phe Gly Lys His Phe
1               5                   10                  15

Val Xaa Glu Ile Xaa Asn Ser
            20

<210> SEQ ID NO 128
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: 2-aminoisobutyric acid
<220> FEATURE:
<221> NAME/KEY: MOD_RES
<222> LOCATION: (18)..(18)
<223> OTHER INFORMATION: Any amino acid whose side chain has been
      replaced by an
      internal staple
<220> FEATURE:
<221> NAME/KEY: MOD_RES
<222> LOCATION: (21)..(21)
<223> OTHER INFORMATION: Norleucine

<400> SEQUENCE: 128

Gly Ile Gly Lys Phe Leu His Ser Ala Lys Xaa Phe Xaa Lys Ala Phe
1               5                   10                  15

Val Xaa Glu Ile Xaa Asn Ser
            20

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 129

Gly Ile Gly Lys Phe Leu His Ser Ala Lys Xaa Phe Pro Lys Ala Phe
1               5                   10                  15

Val Xaa Glu Ile Xaa Asn Ser
            20

<210> SEQ ID NO 130
<211> LENGTH: 23
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 130

Gly Ile Gly Lys Phe Leu His Ser Ala Lys Xaa Phe Xaa Lys Ala Phe
1               5                   10                  15

Val Xaa Glu Ile Xaa Asn Ser
            20

<210> SEQ ID NO 131
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 131

Gly Ile Gly Lys Phe Leu His Ser Ala Lys Xaa Phe Ala Lys Ala Phe
1               5                   10                  15

Val Xaa Glu Ile Xaa Asn Ser
            20

<210> SEQ ID NO 132
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: D-Alanine
<220> FEATURE:
<221> NAME/KEY: MOD_RES
```

```
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 132

Gly Ile Gly Lys Phe Leu His Ser Ala Lys Xaa Phe Xaa Lys Ala Phe
1               5                   10                  15

Val Xaa Glu Ile Xaa Asn Ser
            20

<210> SEQ ID NO 133
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: D-Lysine
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 133

Gly Ile Gly Lys Phe Leu His Ser Ala Lys Xaa Phe Xaa Lys Ala Phe
1               5                   10                  15

Val Xaa Glu Ile Xaa Asn Ser
            20

<210> SEQ ID NO 134
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Norleucine

<400> SEQUENCE: 134

Gly Ile Gly Lys Phe Leu His Ser Ala Lys Lys Phe Gly Lys Ala Phe
1               5                   10                  15

Val Gly Glu Ile Xaa Asn Ser
            20

<210> SEQ ID NO 135
<211> LENGTH: 23
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 135

Gly Xaa Gly Lys Phe Xaa His Ser Ala Lys Lys Phe Gly Lys Ala Phe
1               5                   10                  15

Val Gly Glu Ile Xaa Asn Ser
            20

<210> SEQ ID NO 136
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 136

Gly Ile Xaa Lys Phe Leu Xaa Ser Ala Lys Lys Phe Gly Lys Ala Phe
1               5                   10                  15

Val Gly Glu Ile Xaa Asn Ser
            20

<210> SEQ ID NO 137
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 137
```

```
Gly Ile Gly Xaa Phe Leu His Xaa Ala Lys Lys Phe Gly Lys Ala Phe
1               5                   10                  15

Val Gly Glu Ile Xaa Asn Ser
            20
```

<210> SEQ ID NO 138
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 138

```
Gly Ile Gly Lys Xaa Leu His Ser Xaa Lys Lys Phe Gly Lys Ala Phe
1               5                   10                  15

Val Gly Glu Ile Xaa Asn Ser
            20
```

<210> SEQ ID NO 139
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 139

```
Gly Ile Gly Lys Phe Xaa His Ser Ala Xaa Lys Phe Gly Lys Ala Phe
1               5                   10                  15

Val Gly Glu Ile Xaa Asn Ser
            20
```

<210> SEQ ID NO 140
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 140

Gly Ile Gly Lys Phe Leu Xaa Ser Ala Lys Xaa Phe Gly Lys Ala Phe
1               5                   10                  15

Val Gly Glu Ile Xaa Asn Ser
            20

<210> SEQ ID NO 141
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 141

Gly Ile Gly Lys Phe Leu His Xaa Ala Lys Lys Xaa Gly Lys Ala Phe
1               5                   10                  15

Val Gly Glu Ile Xaa Asn Ser
            20

<210> SEQ ID NO 142
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 142

Gly Ile Gly Lys Phe Leu His Ser Xaa Lys Lys Phe Xaa Lys Ala Phe
1               5                   10                  15
```

Val Gly Glu Ile Xaa Asn Ser
            20

<210> SEQ ID NO 143
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 143

Gly Ile Gly Lys Phe Leu His Ser Ala Xaa Lys Phe Gly Xaa Ala Phe
1               5                   10                  15

Val Gly Glu Ile Xaa Asn Ser
            20

<210> SEQ ID NO 144
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 144

Gly Ile Gly Lys Phe Leu His Ser Ala Lys Xaa Phe Gly Lys Xaa Phe
1               5                   10                  15

Val Gly Glu Ile Xaa Asn Ser
            20

<210> SEQ ID NO 145
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple

```
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 145

Gly Ile Gly Lys Phe Leu His Ser Ala Lys Lys Xaa Gly Lys Ala Xaa
1               5                   10                  15

Val Gly Glu Ile Xaa Asn Ser
            20

<210> SEQ ID NO 146
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 146

Gly Ile Gly Lys Phe Leu His Ser Ala Lys Lys Phe Xaa Lys Ala Phe
1               5                   10                  15

Xaa Gly Glu Ile Xaa Asn Ser
            20

<210> SEQ ID NO 147
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 147

Gly Ile Gly Lys Phe Leu His Ser Ala Lys Lys Phe Gly Xaa Ala Phe
1               5                   10                  15

Val Xaa Glu Ile Xaa Asn Ser
            20
```

<210> SEQ ID NO 148
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 148

Gly Ile Gly Lys Phe Leu His Ser Ala Lys Lys Phe Gly Lys Xaa Phe
1               5                   10                  15

Val Gly Xaa Ile Xaa Asn Ser
            20

<210> SEQ ID NO 149
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 149

Gly Ile Gly Lys Phe Leu His Ser Ala Lys Lys Phe Gly Lys Ala Xaa
1               5                   10                  15

Val Gly Glu Xaa Xaa Asn Ser
            20

<210> SEQ ID NO 150
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)

```
<223> OTHER INFORMATION: Any amino acid whose side chain has been
      replaced by an internal staple

<400> SEQUENCE: 150

Gly Ile Gly Lys Phe Leu His Ser Ala Lys Lys Phe Gly Lys Ala Phe
1               5                   10                  15

Xaa Gly Glu Ile Xaa Asn Ser
            20

<210> SEQ ID NO 151
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 151

Gly Ile Gly Lys Phe Leu His Ser Ala Lys Lys Phe Gly Lys Ala Phe
1               5                   10                  15

Val Xaa Glu Ile Xaa Xaa Ser
            20

<210> SEQ ID NO 152
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 152

Gly Ile Gly Lys Phe Leu His Ser Ala Lys Lys Phe Gly Lys Ala Phe
1               5                   10                  15

Val Gly Xaa Ile Xaa Asn Xaa
            20

<210> SEQ ID NO 153
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 153

Gly Xaa Gly Lys Phe Xaa His Ser Lys Lys Lys Phe Gly Lys Ala Xaa
1               5                   10                  15

Val Gly Glu Xaa Xaa Asn Ser
            20

<210> SEQ ID NO 154
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 154

Gly Ile Xaa Lys Phe Leu Xaa Ser Lys Lys Lys Phe Gly Lys Ala Xaa
1               5                   10                  15

Val Gly Glu Xaa Xaa Asn Ser
            20

<210> SEQ ID NO 155
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 155

Gly Xaa Gly Lys Phe Leu His Ser Xaa Lys Lys Phe Gly Lys Ala Phe
1               5                   10                  15

Val Gly Glu Ile Xaa Asn Ser
            20

<210> SEQ ID NO 156
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 156

Gly Ile Xaa Lys Phe Leu His Ser Ala Xaa Lys Phe Gly Lys Ala Phe
1               5                   10                  15

Val Gly Glu Ile Xaa Asn Ser
            20

<210> SEQ ID NO 157
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
```

<222> LOCATION: (21)..(21)
<223> OTHER INFORMATION: Norleucine

<400> SEQUENCE: 157

Gly Ile Gly Xaa Phe Leu His Ser Ala Lys Xaa Phe Gly Lys Ala Phe
1               5                   10                  15

Val Gly Glu Ile Xaa Asn Ser
            20

<210> SEQ ID NO 158
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 158

Gly Ile Gly Lys Xaa Leu His Ser Ala Lys Lys Xaa Gly Lys Ala Phe
1               5                   10                  15

Val Gly Glu Ile Xaa Asn Ser
            20

<210> SEQ ID NO 159
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 159

Gly Ile Gly Lys Phe Xaa His Ser Ala Lys Lys Phe Xaa Lys Ala Phe
1               5                   10                  15

Val Gly Glu Ile Xaa Asn Ser
            20

<210> SEQ ID NO 160
<211> LENGTH: 23
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 160

Gly Ile Gly Lys Phe Leu Xaa Ser Ala Lys Lys Phe Gly Xaa Ala Phe
1               5                   10                  15

Val Gly Glu Ile Xaa Asn Ser
            20

<210> SEQ ID NO 161
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 161

Gly Ile Gly Lys Phe Leu His Xaa Ala Lys Lys Phe Gly Lys Xaa Phe
1               5                   10                  15

Val Gly Glu Ile Xaa Asn Ser
            20

<210> SEQ ID NO 162
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
```

<400> SEQUENCE: 162

Gly Ile Gly Lys Phe Leu His Ser Xaa Lys Lys Phe Gly Lys Ala Xaa
1               5                   10                  15

Val Gly Glu Ile Xaa Asn Ser
            20

<210> SEQ ID NO 163
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 163

Gly Ile Gly Lys Phe Leu His Ser Ala Xaa Lys Phe Gly Lys Ala Phe
1               5                   10                  15

Xaa Gly Glu Ile Xaa Asn Ser
            20

<210> SEQ ID NO 164
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 164

Gly Ile Gly Lys Phe Leu His Ser Ala Lys Xaa Phe Gly Lys Ala Phe
1               5                   10                  15

Val Xaa Glu Ile Xaa Asn Ser
            20

<210> SEQ ID NO 165
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 165

Gly Ile Gly Lys Phe Leu His Ser Ala Lys Lys Xaa Gly Lys Ala Phe
1               5                   10                  15

Val Gly Xaa Ile Xaa Asn Ser
            20

<210> SEQ ID NO 166
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 166

Gly Ile Gly Lys Phe Leu His Ser Ala Lys Lys Phe Xaa Lys Ala Phe
1               5                   10                  15

Val Gly Glu Xaa Xaa Asn Ser
            20

<210> SEQ ID NO 167
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 167

Gly Ile Gly Lys Phe Leu His Ser Ala Lys Lys Phe Ala Xaa Ala Phe
1               5                   10                  15

Val Gly Glu Ile Xaa Asn Ser
            20

<210> SEQ ID NO 168
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 168

Gly Ile Gly Lys Phe Leu His Ser Ala Lys Lys Phe Ala Lys Xaa Phe
1               5                   10                  15

Val Gly Glu Ile Xaa Xaa Ser
            20

<210> SEQ ID NO 169
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Ile Gly Lys Phe Leu His Ala Ala Lys Lys Phe Ala Lys Ala Phe
1               5                   10                  15

Val Ala Glu Ile Met Asn Ser
            20

<210> SEQ ID NO 170
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 170

Gly Lys Xaa Lys Phe Leu Xaa Ser Lys Lys Phe Gly Lys Ala Xaa
1               5                   10                  15

Val His Glu Xaa Xaa Asn Ser
            20

<210> SEQ ID NO 171
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 171

Gly Lys Xaa Lys Phe Leu Xaa Ser His Lys Lys Phe Gly Lys Ala Xaa
1               5                   10                  15

Val Gly Glu Xaa Xaa Asn Ser
            20

<210> SEQ ID NO 172
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been replaced by an internal staple
<220> FEATURE:
<221> NAME/KEY: MOD_RES
<222> LOCATION: (21)..(21)
<223> OTHER INFORMATION: Norleucine

<400> SEQUENCE: 172

Gly Lys Xaa Lys Phe Leu Xaa Ser His Lys Lys Phe Gly Lys Ala Xaa
1               5                   10                  15

Val Gly Glu Xaa Xaa Glu Ser
            20

<210> SEQ ID NO 173
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 173

Gly Lys Xaa Lys Phe Leu Xaa Ser His Lys Lys Phe Gly Lys Ala Xaa
1               5                   10                  15

Val His Glu Xaa Xaa Glu Ser
            20

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:

```
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 174

Gly Xaa Gly Lys Phe Xaa His Ser Lys Lys Lys Phe Gly Lys Ala Xaa
1               5                   10                  15

Val His Glu Xaa Xaa Glu Ser
            20

<210> SEQ ID NO 175
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 176
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple

<400> SEQUENCE: 176

Gly Xaa Gly Ser Phe Xaa Lys Lys Ala Ala His Val Gly Lys His Xaa
1               5                   10                  15

Gly Lys Ala Xaa Leu Thr His Tyr Leu
            20                  25

<210> SEQ ID NO 177
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple

<400> SEQUENCE: 177

Gly Xaa Gly Ser Phe Xaa Lys Lys Lys Ala His Val Gly Lys His Xaa
1               5                   10                  15

Gly Lys Ala Xaa Leu Thr His Tyr Leu
            20                  25

<210> SEQ ID NO 178
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 178

Gly Ile Gly Lys Phe Leu Xaa Ala Ala Lys Lys Phe Ala Xaa Ala Phe
1               5                   10                  15

Val Ala Glu Ile Xaa Asn Ser
            20

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
```

```
<221> NAME/KEY: MOD_RES
<222> LOCATION: (21)..(21)
<223> OTHER INFORMATION: Norleucine

<400> SEQUENCE: 179

Gly Ile Gly Lys Phe Leu His Xaa Ala Lys Lys Phe Ala Lys Xaa Phe
1               5                   10                  15

Val Ala Glu Ile Xaa Asn Ser
            20

<210> SEQ ID NO 180
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 180

Gly Ile Gly Lys Phe Leu His Ala Xaa Lys Lys Phe Ala Lys Ala Xaa
1               5                   10                  15

Val Ala Glu Ile Xaa Asn Ser
            20

<210> SEQ ID NO 181
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 181

Gly Ile Gly Lys Phe Leu His Ala Ala Xaa Lys Phe Ala Lys Ala Phe
1               5                   10                  15

Xaa Ala Glu Ile Xaa Asn Ser
            20

<210> SEQ ID NO 182
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 182

Gly Ile Gly Lys Phe Leu His Ala Ala Lys Xaa Phe Ala Lys Ala Phe
1               5                   10                  15

Val Xaa Glu Ile Xaa Asn Ser
            20

<210> SEQ ID NO 183
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 183

Gly Ile Gly Lys Phe Leu His Ala Ala Lys Lys Xaa Ala Lys Ala Phe
1               5                   10                  15

Val Ala Xaa Ile Xaa Asn Ser
            20

<210> SEQ ID NO 184
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
```

<400> SEQUENCE: 184

Gly Ile Gly Lys Phe Leu His Ala Ala Lys Lys Phe Xaa Lys Ala Phe
1               5                   10                  15

Val Ala Glu Xaa Xaa Asn Ser
            20

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple

<400> SEQUENCE: 185

Gly Ile Gly Lys Phe Leu Lys Xaa Ala Lys Lys Phe Gly Lys Xaa Phe
1               5                   10                  15

Val Lys Ile Leu Lys Lys
            20

<210> SEQ ID NO 186
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple

<400> SEQUENCE: 186

Gly Ile Gly Lys Phe Leu Lys Lys Ala Lys Xaa Phe Gly Lys Ala Phe
1               5                   10                  15

Val Xaa Ile Leu Lys Lys
            20

<210> SEQ ID NO 187
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)

<223> OTHER INFORMATION: Any amino acid whose side chain has been
      replaced by an internal staple

<400> SEQUENCE: 187

Gly Ile Gly Lys Phe Leu Lys Lys Ala Lys Lys Xaa Gly Lys Ala Phe
1               5                   10                  15

Val Lys Xaa Leu Lys Lys
            20

<210> SEQ ID NO 188
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 188

Gly Ile Gly Lys Phe Leu Xaa Ala Ala Lys Lys Phe Ala Xaa Ala Phe
1               5                   10                  15

Val Ala Glu Ile Xaa Asn Ser
            20

<210> SEQ ID NO 189
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 189

Gly Ile Gly Lys Phe Leu His Xaa Ala Lys Lys Phe Ala Lys Xaa Phe
1               5                   10                  15

Val Ala Glu Ile Xaa Asn Ser
            20

<210> SEQ ID NO 190
<211> LENGTH: 23
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 190

Gly Ile Gly Lys Phe Leu His Ala Xaa Lys Lys Phe Ala Lys Ala Xaa
1               5                   10                  15

Val Ala Glu Ile Xaa Asn Ser
            20

<210> SEQ ID NO 191
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 191

Gly Ile Gly Lys Phe Leu His Ala Ala Xaa Lys Phe Ala Lys Ala Phe
1               5                   10                  15

Xaa Ala Glu Ile Xaa Asn Ser
            20

<210> SEQ ID NO 192
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
```

<400> SEQUENCE: 192

Gly Ile Gly Lys Phe Leu His Ala Ala Lys Xaa Phe Ala Lys Ala Phe
1               5                   10                  15

Val Xaa Glu Ile Xaa Asn Ser
            20

<210> SEQ ID NO 193
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 193

Gly Ile Gly Lys Phe Leu His Ala Ala Lys Lys Xaa Ala Lys Ala Phe
1               5                   10                  15

Val Ala Xaa Ile Xaa Asn Ser
            20

<210> SEQ ID NO 194
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 194

Gly Ile Gly Lys Phe Leu His Ala Ala Lys Lys Phe Xaa Lys Ala Phe
1               5                   10                  15

Val Ala Glu Xaa Xaa Asn Ser
            20

<210> SEQ ID NO 195
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 195

Gly Ile Gly Lys Phe Leu His Ala Ala Lys Lys Phe Ala Xaa Ala Phe
1               5                   10                  15

Val Ala Glu Ile Xaa Asn Ser
            20

<210> SEQ ID NO 196
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 196

Gly Ile Gly Lys Phe Leu His Ala Ala Lys Lys Phe Ala Lys Xaa Phe
1               5                   10                  15

Val Ala Glu Ile Xaa Xaa Ser
            20

<210> SEQ ID NO 197
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an
internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 197

Gly Ile Gly Lys Phe Leu His Ala Ala Lys Lys Phe Ala Lys Ala Xaa
1               5                   10                  15

Val Ala Glu Ile Xaa Asn Xaa
```

```
<210> SEQ ID NO 198
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 198

Gly Ile Gly Lys Phe Xaa His Ala Ala Lys Lys Phe Xaa Lys Ala Phe
1               5                   10                  15

Val Ala Glu Ile Xaa Asn Ser
            20

<210> SEQ ID NO 199
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 199

Gly Ile Gly Lys Xaa Leu His Ala Ala Lys Lys Xaa Ala Lys Ala Phe
1               5                   10                  15

Val Ala Glu Ile Xaa Asn Ser
            20

<210> SEQ ID NO 200
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
```

```
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 200

Gly Ile Gly Xaa Phe Leu His Ala Ala Lys Xaa Phe Ala Lys Ala Phe
1               5                   10                  15

Val Ala Glu Ile Xaa Asn Ser
            20

<210> SEQ ID NO 201
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 201

Gly Ile Xaa Lys Phe Leu His Ala Ala Xaa Lys Phe Ala Lys Ala Phe
1               5                   10                  15

Val Ala Glu Ile Xaa Asn Ser
            20

<210> SEQ ID NO 202
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 202

Gly Xaa Gly Lys Phe Leu His Ala Xaa Lys Phe Ala Lys Ala Phe
1               5                   10                  15

Val Ala Glu Ile Xaa Asn Ser
            20
```

```
<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 203

Xaa Ile Gly Lys Phe Leu His Xaa Ala Lys Lys Phe Ala Lys Ala Phe
1               5                   10                  15

Val Ala Glu Ile Xaa Asn Ser
            20

<210> SEQ ID NO 204
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 204

Xaa Ile Gly Lys Xaa Leu His Ala Ala Lys Lys Phe Ala Lys Ala Phe
1               5                   10                  15

Val Ala Glu Ile Xaa Asn Ser
            20

<210> SEQ ID NO 205
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
```

```
<220> FEATURE:
<221> NAME/KEY: MOD_RES
<222> LOCATION: (21)..(21)
<223> OTHER INFORMATION: Norleucine

<400> SEQUENCE: 205

Gly Xaa Gly Lys Phe Xaa His Ala Ala Lys Lys Phe Ala Lys Ala Phe
1               5                   10                  15

Val Ala Glu Ile Xaa Asn Ser
            20

<210> SEQ ID NO 206
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 206

Gly Ile Xaa Lys Phe Leu Xaa Ala Ala Lys Lys Phe Ala Lys Ala Phe
1               5                   10                  15

Val Ala Glu Ile Xaa Asn Ser
            20

<210> SEQ ID NO 207
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 207

Gly Ile Gly Xaa Phe Leu His Xaa Ala Lys Lys Phe Ala Lys Ala Phe
1               5                   10                  15

Val Ala Glu Ile Xaa Asn Ser
            20

<210> SEQ ID NO 208
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 208

Gly Ile Gly Lys Xaa Leu His Ala Xaa Lys Lys Phe Ala Lys Ala Phe
1               5                   10                  15

Val Ala Glu Ile Xaa Asn Ser
            20

<210> SEQ ID NO 209
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 209

Gly Ile Gly Lys Phe Xaa His Ala Ala Xaa Lys Phe Ala Lys Ala Phe
1               5                   10                  15

Val Ala Glu Ile Xaa Asn Ser
            20

<210> SEQ ID NO 210
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (21)..(21)
```

<223> OTHER INFORMATION: Norleucine

<400> SEQUENCE: 210

Gly Ile Gly Lys Phe Leu Xaa Ala Ala Lys Xaa Phe Ala Lys Ala Phe
1               5                   10                  15

Val Ala Glu Ile Xaa Asn Ser
            20

<210> SEQ ID NO 211
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 211

Gly Ile Gly Lys Phe Leu His Xaa Ala Lys Lys Xaa Ala Lys Ala Phe
1               5                   10                  15

Val Ala Glu Ile Xaa Asn Ser
            20

<210> SEQ ID NO 212
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 212

Gly Ile Gly Lys Phe Leu His Ala Xaa Lys Lys Phe Xaa Lys Ala Phe
1               5                   10                  15

Val Ala Glu Ile Xaa Asn Ser
            20

<210> SEQ ID NO 213
<211> LENGTH: 23
<212> TYPE: PRT
<213> ORGANISM: Artificial Sequence
<220> FEATURE:
<223> OTHER INFORMATION: Description of Artificial Sequence: Synthetic -continued

```
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 213

Gly Ile Gly Lys Phe Leu His Ala Ala Xaa Lys Phe Ala Xaa Ala Phe
1               5                   10                  15

Val Ala Glu Ile Xaa Asn Ser
            20

<210> SEQ ID NO 214
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 214

Gly Ile Gly Lys Phe Leu His Ala Ala Lys Xaa Phe Ala Lys Xaa Phe
1               5                   10                  15

Val Ala Glu Ile Xaa Asn Ser
            20

<210> SEQ ID NO 215
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 215
```

```
Gly Ile Gly Lys Phe Leu His Ala Ala Lys Lys Xaa Ala Lys Ala Xaa
1               5                   10                  15

Val Ala Glu Ile Xaa Asn Ser
            20

<210> SEQ ID NO 216
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 216

Gly Ile Gly Lys Phe Leu His Ala Ala Lys Lys Phe Xaa Lys Ala Phe
1               5                   10                  15

Xaa Ala Glu Ile Xaa Asn Ser
            20

<210> SEQ ID NO 217
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 217

Gly Ile Gly Lys Phe Leu His Ala Ala Lys Lys Phe Ala Xaa Ala Phe
1               5                   10                  15

Val Xaa Glu Ile Xaa Asn Ser
            20

<210> SEQ ID NO 218
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 218

Gly Ile Gly Lys Phe Leu His Ala Ala Lys Lys Phe Ala Lys Xaa Phe
1               5                   10                  15

Val Ala Xaa Ile Xaa Asn Ser
            20

<210> SEQ ID NO 219
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 219

Gly Ile Gly Lys Phe Leu His Ala Ala Lys Lys Phe Ala Lys Ala Xaa
1               5                   10                  15

Val Ala Glu Xaa Xaa Asn Ser
            20

<210> SEQ ID NO 220
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 220

Gly Ile Gly Lys Phe Leu His Ala Ala Lys Lys Phe Ala Lys Ala Phe
1               5                   10                  15

Xaa Ala Glu Ile Xaa Asn Ser
            20
```

```
<210> SEQ ID NO 221
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 221

Gly Ile Gly Lys Phe Leu His Ala Ala Lys Lys Phe Ala Lys Ala Phe
1               5                   10                  15

Val Xaa Glu Ile Xaa Xaa Ser
            20

<210> SEQ ID NO 222
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 222

Gly Ile Gly Lys Phe Leu His Ala Ala Lys Lys Phe Ala Lys Ala Phe
1               5                   10                  15

Val Ala Xaa Ile Xaa Asn Xaa
            20

<210> SEQ ID NO 223
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (4)..(4)
<223> OTHER INFORMATION: Any amino acid whose side chain has been
```

```
      replaced by an internal staple
<220> FEATURE:
<221> NAME/KEY: MOD_RES
<222> LOCATION: (21)..(21)
<223> OTHER INFORMATION: Norleucine

<400> SEQUENCE: 223

Xaa Ile Gly Xaa Phe Leu His Ala Ala Lys Lys Phe Ala Lys Ala Phe
1               5                   10                  15

Val Ala Glu Ile Xaa Asn Ser
            20

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 224

Gly Xaa Gly Lys Xaa Leu His Ala Ala Lys Lys Phe Ala Lys Ala Phe
1               5                   10                  15

Val Ala Glu Ile Xaa Asn Ser
            20

<210> SEQ ID NO 225
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 225

Gly Ile Xaa Lys Phe Xaa His Ala Ala Lys Lys Phe Ala Lys Ala Phe
1               5                   10                  15

Val Ala Glu Ile Xaa Asn Ser
            20

<210> SEQ ID NO 226
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 226

Gly Ile Gly Xaa Phe Leu Xaa Ala Ala Lys Lys Phe Ala Lys Ala Phe
1               5                   10                  15

Val Ala Glu Ile Xaa Asn Ser
            20

<210> SEQ ID NO 227
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 227

Gly Ile Gly Lys Xaa Leu His Xaa Ala Lys Lys Phe Ala Lys Ala Phe
1               5                   10                  15

Val Ala Glu Ile Xaa Asn Ser
            20

<210> SEQ ID NO 228
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
```

<222> LOCATION: (21)..(21)
<223> OTHER INFORMATION: Norleucine

<400> SEQUENCE: 228

Gly Ile Gly Lys Phe Xaa His Ala Xaa Lys Lys Phe Ala Lys Ala Phe
1               5                  10                  15

Val Ala Glu Ile Xaa Asn Ser
            20

<210> SEQ ID NO 229
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 229

Gly Ile Gly Lys Phe Leu Xaa Ala Ala Xaa Lys Phe Ala Lys Ala Phe
1               5                  10                  15

Val Ala Glu Ile Xaa Asn Ser
            20

<210> SEQ ID NO 230
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 230

Gly Ile Gly Lys Phe Leu His Xaa Ala Lys Xaa Phe Ala Lys Ala Phe
1               5                  10                  15

Val Ala Glu Ile Xaa Asn Ser
            20

<210> SEQ ID NO 231
<211> LENGTH: 23
<212> TYPE: PRT
<213> ORGANISM: Artificial Sequence
<220> FEATURE:

-continued

<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 231

Gly Ile Gly Lys Phe Leu His Ala Xaa Lys Lys Xaa Ala Lys Ala Phe
1               5                  10                  15

Val Ala Glu Ile Xaa Asn Ser
            20

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 232

Gly Ile Gly Lys Phe Leu His Ala Ala Xaa Lys Phe Xaa Lys Ala Phe
1               5                  10                  15

Val Ala Glu Ile Xaa Asn Ser
            20

<210> SEQ ID NO 233
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

```
<400> SEQUENCE: 233

Gly Ile Gly Lys Phe Leu His Ala Ala Lys Xaa Phe Ala Xaa Ala Phe
1               5                   10                  15

Val Ala Glu Ile Xaa Asn Ser
            20

<210> SEQ ID NO 234
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 234

Gly Ile Gly Lys Phe Leu His Ala Ala Lys Lys Xaa Ala Lys Xaa Phe
1               5                   10                  15

Val Ala Glu Ile Xaa Asn Ser
            20

<210> SEQ ID NO 235
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 235

Gly Ile Gly Lys Phe Leu His Ala Ala Lys Lys Phe Xaa Lys Ala Xaa
1               5                   10                  15

Val Ala Glu Ile Xaa Asn Ser
            20

<210> SEQ ID NO 236
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 236

Gly Ile Gly Lys Phe Leu His Ala Ala Lys Lys Phe Ala Xaa Ala Phe
1               5                   10                  15

Xaa Ala Glu Ile Xaa Asn Ser
            20

<210> SEQ ID NO 237
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 237

Gly Ile Gly Lys Phe Leu His Ala Ala Lys Lys Phe Ala Lys Xaa Phe
1               5                   10                  15

Val Xaa Glu Ile Xaa Asn Ser
            20

<210> SEQ ID NO 238
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 238

Gly Ile Gly Lys Phe Leu His Ala Ala Lys Lys Phe Ala Lys Ala Xaa
```

Val Ala Xaa Ile Xaa Asn Ser
            20

<210> SEQ ID NO 239
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 239

Gly Ile Gly Lys Phe Leu His Ala Ala Lys Lys Phe Ala Lys Ala Phe
1               5                   10                  15

Xaa Ala Glu Xaa Xaa Asn Ser
            20

<210> SEQ ID NO 240
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 240

Gly Ile Gly Lys Phe Leu His Ala Ala Lys Lys Phe Ala Lys Ala Phe
1               5                   10                  15

Val Xaa Glu Ile Xaa Asn Ser
            20

<210> SEQ ID NO 241
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)

```
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 241

Gly Ile Gly Lys Phe Leu His Ala Ala Lys Lys Phe Ala Lys Ala Phe
1               5                   10                  15

Val Ala Xaa Ile Xaa Xaa Ser
            20

<210> SEQ ID NO 242
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 242

Gly Ile Gly Lys Phe Leu His Ala Ala Lys Lys Phe Ala Lys Ala Phe
1               5                   10                  15

Val Ala Glu Xaa Xaa Asn Xaa
            20

<210> SEQ ID NO 243
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
```

<400> SEQUENCE: 243

Gly Xaa Gly Lys Xaa Leu His Ala Ala Lys Lys Xaa Ala Lys Ala Phe
1               5                   10                  15

Val Ala Xaa Ile Xaa Asn Ser
            20

<210> SEQ ID NO 244
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple
<220> FEATURE:
<221> NAME/KEY: MOD_RES
<222> LOCATION: (18)..(18)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 244

Gly Ile Xaa Lys Phe Xaa His Ala Ala Lys Xaa Phe Ala Lys Ala Phe
1               5                   10                  15

Val Xaa Glu Ile Xaa Asn Ser
            20

<210> SEQ ID NO 245
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES

```
<222> LOCATION: (21)..(21)
<223> OTHER INFORMATION: Norleucine

<400> SEQUENCE: 245

Gly Ile Xaa Lys Phe Leu Xaa Ala Ala Lys Lys Phe Xaa Lys Ala Phe
1               5                   10                  15

Xaa Ala Glu Ile Xaa Asn Ser
            20

<210> SEQ ID NO 246
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 246

Gly Ile Gly Xaa Phe Leu His Xaa Ala Lys Lys Phe Xaa Lys Ala Phe
1               5                   10                  15

Xaa Ala Glu Ile Xaa Asn Ser
            20

<210> SEQ ID NO 247
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
```

```
           replaced by an internal staple
<220> FEATURE:
<221> NAME/KEY: MOD_RES
<222> LOCATION: (21)..(21)
<223> OTHER INFORMATION: Norleucine

<400> SEQUENCE: 247

Gly Xaa Gly Lys Phe Xaa His Ala Ala Lys Lys Phe Xaa Lys Ala Phe
1               5                   10                  15

Val Ala Glu Xaa Xaa Asn Ser
            20

<210> SEQ ID NO 248
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 248

Gly Xaa Gly Lys Phe Leu His Ala Xaa Lys Lys Phe Ala Lys Ala Xaa
1               5                   10                  15

Val Ala Glu Ile Xaa Asn Xaa
            20

<210> SEQ ID NO 249
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
```

```
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (22)..(22)
<223> OTHER INFORMATION: Any amino acid whose side chain has been
      replaced by an internal staple

<400> SEQUENCE: 249

Gly Ile Xaa Lys Phe Leu His Ala Ala Xaa Lys Phe Ala Lys Xaa Phe
1               5                   10                  15

Val Ala Glu Ile Xaa Xaa Ser
            20

<210> SEQ ID NO 250
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 250

Xaa Ile Gly Lys Phe Leu His Xaa Ala Lys Lys Phe Ala Lys Ala Phe
1               5                   10                  15

Xaa Ala Glu Ile Xaa Asn Ser
            20

<210> SEQ ID NO 251
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
```

```
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 251

Gly Xaa Gly Lys Phe Leu His Ala Xaa Lys Lys Phe Ala Lys Ala Xaa
1               5                   10                  15

Val Ala Glu Xaa Xaa Asn Ser
            20

<210> SEQ ID NO 252
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 252

Gly Ile Xaa Lys Phe Leu His Ala Ala Xaa Lys Phe Ala Lys Xaa Phe
1               5                   10                  15

Val Ala Xaa Ile Xaa Asn Ser
            20

<210> SEQ ID NO 253
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-alpha-(4-Pentenyl)alanine
<220> FEATURE:
<221> NAME/KEY: MOD_RES
<222> LOCATION: (8)..(8)
<223> OTHER INFORMATION: (S)-alpha-(4-Pentenyl)alanine

<400> SEQUENCE: 253

Xaa Ile Gly Lys Phe Leu Lys Xaa Ala Lys Lys Phe Gly Lys Ala Phe
1               5                   10                  15
```

```
Val Lys Ile Leu Lys Lys
            20

<210> SEQ ID NO 254
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-alpha-(7-Octenyl)alanine
<220> FEATURE:
<221> NAME/KEY: MOD_RES
<222> LOCATION: (6)..(6)
<223> OTHER INFORMATION: (S)-alpha-(4-Pentenyl)alanine

<400> SEQUENCE: 254

Xaa Ile Gly Lys Phe Xaa Lys Lys Ala Lys Lys Phe Gly Lys Ala Phe
1               5                   10                  15

Val Lys Ile Leu Lys Lys
            20

<210> SEQ ID NO 255
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-alpha-(7-Octenyl)alanine
<220> FEATURE:
<221> NAME/KEY: MOD_RES
<222> LOCATION: (5)..(5)
<223> OTHER INFORMATION: (R)-alpha-Allylalanine

<400> SEQUENCE: 255

Xaa Ile Gly Lys Xaa Leu Lys Lys Ala Lys Lys Phe Gly Lys Ala Phe
1               5                   10                  15

Val Lys Ile Leu Lys Lys
            20

<210> SEQ ID NO 256
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-alpha-(4-Pentenyl)alanine
<220> FEATURE:
<221> NAME/KEY: MOD_RES
<222> LOCATION: (8)..(8)
<223> OTHER INFORMATION: (S)-alpha-(4-Pentenyl)alanine
<220> FEATURE:
<221> NAME/KEY: MOD_RES
<222> LOCATION: (15)..(15)
<223> OTHER INFORMATION: (S)-alpha-(4-Pentenyl)alanine
<220> FEATURE:
<221> NAME/KEY: MOD_RES
<222> LOCATION: (22)..(22)
<223> OTHER INFORMATION: (S)-alpha-(4-Pentenyl)alanine

<400> SEQUENCE: 256
```

```
Xaa Ile Gly Lys Phe Leu Lys Xaa Ala Lys Lys Phe Gly Lys Xaa Phe
1               5                   10                  15

Val Lys Ile Leu Lys Xaa
            20
```

<210> SEQ ID NO 257
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-alpha-(7-Octenyl)alanine
<220> FEATURE:
<221> NAME/KEY: MOD_RES
<222> LOCATION: (6)..(6)
<223> OTHER INFORMATION: (S)-alpha-(4-Pentenyl)alanine
<220> FEATURE:
<221> NAME/KEY: MOD_RES
<222> LOCATION: (17)..(17)
<223> OTHER INFORMATION: (R)-alpha-(7-Octenyl)alanine
<220> FEATURE:
<221> NAME/KEY: MOD_RES
<222> LOCATION: (22)..(22)
<223> OTHER INFORMATION: (S)-alpha-(4-Pentenyl)alanine

<400> SEQUENCE: 257

```
Xaa Ile Gly Lys Phe Xaa Lys Lys Ala Lys Lys Phe Gly Lys Ala Phe
1               5                   10                  15

Xaa Lys Ile Leu Lys Xaa
            20
```

<210> SEQ ID NO 258
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-alpha-(7-Octenyl)alanine
<220> FEATURE:
<221> NAME/KEY: MOD_RES
<222> LOCATION: (5)..(5)
<223> OTHER INFORMATION: (R)-alpha-Allylalanine
<220> FEATURE:
<221> NAME/KEY: MOD_RES
<222> LOCATION: (18)..(18)
<223> OTHER INFORMATION: (R)-alpha-(7-Octenyl)alanine
<220> FEATURE:
<221> NAME/KEY: MOD_RES
<222> LOCATION: (22)..(22)
<223> OTHER INFORMATION: (R)-alpha-Allylalanine

<400> SEQUENCE: 258

```
Xaa Ile Gly Lys Xaa Leu Lys Lys Ala Lys Lys Phe Gly Lys Ala Phe
1               5                   10                  15

Val Xaa Ile Leu Lys Xaa
            20
```

<210> SEQ ID NO 259
<211> LENGTH: 22
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (12)..(13)
<223> OTHER INFORMATION: Any naturally occurring amino acid
<220> FEATURE:
<221> NAME/KEY: MOD_RES
<222> LOCATION: (15)..(17)
<223> OTHER INFORMATION: Any naturally occurring amino acid
<220> FEATURE:
<221> NAME/KEY: MOD_RES
<222> LOCATION: (19)..(20)
<223> OTHER INFORMATION: Any naturally occurring amino acid

<400> SEQUENCE: 259

Xaa Xaa Xaa Lys Xaa Xaa Lys Lys Xaa Lys Lys Xaa Xaa Lys Xaa Xaa
1               5                   10                  15

Xaa Lys Xaa Xaa Lys Lys
            20

<210> SEQ ID NO 260
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Phe or Ser
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 260

Gly Ile Gly Lys Phe Leu His Ser Ala Lys Lys Xaa Gly Lys Xaa Phe
1               5                   10                  15

Val Gly Xaa Ile Xaa Asn
            20

<210> SEQ ID NO 261
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (12)..(12)
<223> OTHER INFORMATION: Phe or Ser
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Norleucine

<400> SEQUENCE: 261

Gly Ile Gly Lys Phe Leu His Ser Ala Lys Lys Xaa Gly Lys Ala Xaa
1               5                   10                  15

Val Gly Glu Xaa Xaa Asn
            20

<210> SEQ ID NO 262
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Phe or Ser

<400> SEQUENCE: 262

Gly Ile Gly Lys Phe Leu His Ser Ala Lys Lys Xaa Gly Lys Ala Phe
1               5                   10                  15

Val Gly Glu Ile Met Asn
            20
```

STABILIZED ANTI-MICROBIAL PEPTIDES

CROSS-REFERENCE

This application claims the benefit of U.S. Provisional Application No. 62/188,448 filed Jul. 2, 2015, and U.S. Provisional Application No. 62/301,518 filed Feb. 29, 2016, each of which are incorporated herein by reference in its entirety.

SEQUENCE LISTING

The instant application contains a Sequence listing which has been submitted electronically in ASCII format and is hereby incorporated by reference in its entirety. Said ASCII copy, created on Sep. 29, 2016, is named 00530-0323001_SL.txt and is 173,654 bytes in size.

BACKGROUND

Anti-microbial peptides (AMPs) are an evolutionarily conserved class of proteins that form an essential line of defense against microbial invasion. These peptides are produced by many disparate organisms and have been found to exhibit a wide spectrum of activity against bacteria, fungi (including yeasts), protozoa (including parasites), and viruses.

AMPs can be divided into four main structural groups: stabilized β-sheet peptides with two to four disulfide bridges; loop peptides with a single disulfide bridge; α-helical peptides; and extended structures rich in arginine, glycine, proline, tryptophan, and histidine. Typically 12 to 50 amino acids in length, these peptides are usually cationic with an amphipathic character. These biophysical properties allow them to interact with bacterial membranes resulting in either disruption of membrane integrity or translocation into bacterial cells and disruption of intracellular processes.

The alpha-helical structural motif of AMPs can be important to the ability of AMPs to interact with bacterial membranes. Upon binding to the membrane, AMPs can either translocate or insert themselves and permeabilize the membrane through a barrel-stove mechanism, a carpet-like mechanism or a toroidal pore mechanism. This process of permeabilization and disruption of membrane integrity can account for the antimicrobial properties of alpha-helical AMPs.

SUMMARY

The present disclosure provides structurally-stabilized peptides related to (e.g., sharing sequence homology with) anti-microbial peptides (AMPs), and methods for using such stabilized peptides as therapeutic and/or prophylactic agents. Methods are also provided for designing stabilized anti-microbial peptides that are selectively lytic/cytotoxic to bacteria, allowing for internal use of anti-microbial peptides without mammalian membrane disruption and cytotoxicity.

More specifically, the document provides a compound having the Formula (I):

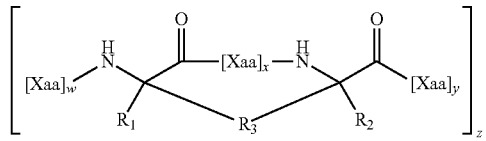

Formula (I)

or a pharmaceutically acceptable salt thereof, wherein;

each $R_1$ and $R_2$ is independently H, alkyl, alkenyl, alkynyl, arylalkyl, cycloalkylalkyl, heteroarylalkyl, or heterocyclylalkyl, any of which is substituted or unsubstituted;

each $R_3$ is independently alkylene, alkenylene, or alkynylene, any of which is substituted or unsubstituted;

each x is independently 1, 2, 3, 4, 5, 6, 7, 8, 9, or 10;

each w and y is independently 1, 2, 3, 4, 5, 6, 7, 8, 9, 10, 11, 12, 13, 14, 15, 16, 17, 18, 19, or 20;

z is 1, 2, 3, 4, 5, 6, 7, 8, 9, or 10; and each Xaa is independently an amino acid;

wherein the compound exhibits an antimicrobial effect against at least one microbe.

In some aspects, x is independently 2, 3, or 6.

Moreover, the document additionally provides an internally cross-linked (ICL) anti-microbial peptide (AMP) containing amino acids, the side chains of at least one pair (e.g., one or two pairs) of amino acids separated by 2, 3, or 6 amino acids being replaced, relative to the corresponding parent non-internally cross-linked AMP, by the linking group, $R_3$, which connects the alpha carbons of the pair of amino acids such that:

each $R_3$ is independently alkylene, alkenylene, or alkynylene (e.g., a $C_6$, $C_7$, or $C_{11}$ alkenylene) optionally substituted, e.g., with 1-6 $R_4$; and each $R_4$ is independently —$NH_3$ or —OH, wherein each —$NH_3$ is optionally substituted; and each $R_1$ and $R_2$ is independently $C_1$ to $C_{10}$ alkyl, alkenyl, alkynyl, arylalkyl, cycloalkylalkyl, heteroarylalkyl, or heterocyclylalkyl, any of which is substituted or unsubstituted.

In some aspects, the ICL AMP contains at least 18 contiguous amino acids of any of SEQ ID NOs: 1-17 or a variant thereof having 1, 2, 3, 4, or 5 amino acid substitutions, or another polypeptide sequence described herein except that: (a) within the 18 contiguous amino acids the side chains of at least one pair (e.g., one or two pairs) of amino acids separated by 2, 3, or 6 amino acids are replaced, relative to the corresponding parent non-internally cross-linked AMP, by the linking group, $R_3$, which connects the alpha carbons of the pair of amino acids as depicted in Formula (I) and the alpha carbon of the second of the pair of amino acids is substituted with $R_2$ as depicted in Formula (I). In certain aspects, the AMP variant comprises at least 18 contiguous amino acids of any of SEQ ID NOs: 1-17 except that it includes (i) at least one (e.g., 1, 2, 3) substitution of an amino acid to histidine; and/or (ii) at least one (e.g., 1, 2, 3) substitution of an amino acid to lysine; and/or (iii) at least one (e.g., 1, 2, 3) substitution of an amino acid to D-alanine.

Moreover, the document additionally provides an internally cross-linked (ICL) anti-microbial peptide (AMP) containing at least 20 amino acids, the side chains of at least one pair (e.g., one or two pairs) of amino acids separated by 2, 3, or 6 amino acids being replaced, relative to the corresponding parent non-internally cross-linked AMP, by the linking group, $R_3$, which connects the alpha carbons of the pair of amino acids such that:

each $R_3$ is independently alkylene, alkenylene, or alkynylene (e.g., a $C_6$, $C_7$, or $C_{11}$ alkenylene), optionally substituted with 1-6 $R_4$;

each $R_4$ is independently —$NH_3$ or —OH, wherein each —$NH_3$ is optionally substituted; and each $R_1$ and $R_2$ is independently $C_1$ to $C_{10}$ alkyl, alkenyl, alkynyl, arylalkyl, cycloalkylalkyl, heteroarylalkyl, or heterocyclylalkyl, any of which is substituted or unsubstituted.

Any of the above-described ICL AMPs can have $R_3$ substituted with 0, 1, 2, 3, 4, 5, 6, 7, 8, 9, or 10 $R_4$. Each $R_4$ can be —OH. In some aspects, one $R_3$ is —$NH_3$ and another is —OH.

Any of the above-described ICL AMPs can contain at least 18 contiguous amino acids of any of SEQ ID NOs: 1-17 (e.g., SEQ ID NO: 1) or a variant thereof having 1, 2, 3, 4, or 5 amino acid substitutions, or another polypeptide sequence described herein except that: (a) within the 18 contiguous amino acids the side chains of at least one pair (e.g., one or two pairs) of amino acids separated by 2, 3, or 6 amino acids are replaced, relative to the corresponding parent non-internally cross-linked AMP, by the linking group, $R_3$, which connects the alpha carbons of the pair of amino acids and the H of the alpha carbon of each pair of amino acids having their side chains replaced by linking group $R_3$ is optionally, independently replaced by a $C_1$ to $C_{10}$ alkyl, alkenyl, or alkynyl.

Any of the above-described ICL AMPs can contain an α-helical region including a first surface hydrophobic patch, such that the replacement with the linking group maintains or results in, relative to the parent AMP without the replacement, discontinuity between the first surface hydrophobic patch and an additional surface hydrophobic patch or patches on the α-helical region of the peptide. Moreover, the linking group can contain a hydrophilizing modification, e.g., dihydroxylation. The replacement with the linking group can be located in the first surface hydrophobic patch, an additional surface hydrophobic patch, or the first surface hydrophobic patch and an additional surface hydrophobic patch on the AMP.

Any of the above-described ICL AMPs can contain the sequence of any of SEQ ID NOs: 18-168 and 170-174. They can, e.g., contain the sequence of Mag(i+4)1 (SEQ ID NO: 135), Mag(i+4)2 (SEQ ID NO: 136), Mag(i+4)4 (SEQ ID NO: 138), Mag(i+4)5 (SEQ ID NO: 139), Mag(i+4)6 (SEQ ID NO: 140), Mag(i+4)11 (SEQ ID NO: 145), Mag(i+4)15 (SEQ ID NO: 149), Mag(i+4)16 (SEQ ID NO: 150), Mag (i+4)2,15(I2K, A9K, G18H) (SEQ ID NO: 170), Mag(i+4) 2,15(I2K, A9H) (SEQ ID NO: 171), Mag(i+4)2,15(I2K, A9H, N21E) (SEQ ID NO: 172), Mag(i+4)2,15(I2K, A9H, G18H, N21E) (SEQ ID NO: 173), or Mag(i+4)1,15(S8H, A9K, G18H, N21E) (SEQ ID NO: 174).

The document also features a method of treating or preventing a microbial infection, the method including administering an effective amount of any of the ICL AMPs described above to a subject having, or at risk of having, an infection with a microbial organism. The subject can be an animal or plant. The animal can be a mammal, e.g., a human. The microbial organism can be a bacterial organism, e.g., a Gram-positive bacterial organism or a Gram-negative bacterial organism. The subject can have, or be at risk of having, a bacterial vaginal infection. The bacterial vaginal infection can include bacterial vaginosis. The bacterial vaginal infection can include an infection with one or more bacterial organisms that increase the likelihood of transmission of a viral infection to the subject. The viral infection can be a human immunodeficiency virus-1 (HIV-1) or human immunodeficiency virus-2 (HIV-2) infection. Any of the above-described ICL AMPs can be administered topically, e.g., to the vagina. Any of the above-described ICL AMPs can be administered, e.g., to the lung. The subject can include a bacterial biofilm. The subject can have, or be at risk of having, cystic fibrosis.

The method can further include administering an effective amount of at least one antibiotic. The established antibiotic can act synergistically with the ICL AMP to inhibit or prevent infection with the microbial organism. The ICL AMP and the antibiotic can synergistically to overcome or prevent resistance to the antibiotic.

Another aspect of the document is a composition containing one or more of the any of the ICL AMPs described above. The composition can further contain a food product or beverage. Any of the above-described ICL AMPs can be added to the food product or beverage prior to or during a fermentation or sterilization process.

The composition can further contain a medical or hygienic device. The one or more ICL AMPs can be coated onto or impregnated into the medical or hygienic device. The composition can also contain one or more antibiotics.

Also provided by the document is a method of inhibiting the growth of, or killing, a microbial organism that involves contacting the microbial organism with one or more of any of the above-described ICL AMPs. The microbial organism can be an extracellular microbial organism or an intracellular microbial organism. The contacting can occur in a subject comprising the microbial organism. Alternatively, the method can be an in vitro method. It is understood that the method can be implemented using any of the features described in the document (e.g., those described above for a method of treating or preventing a microbial infection). The microbial organism can be, e.g., *Mycobacterium tuberculosis*.

Another feature of the document is a method of making any of the above-described ICL AMPs, the method involving, with reference to Formula (I): synthesizing an ICL AMP, determining the location of an established surface hydrophobic patch in an α-helical region of the peptide, and selecting integers w and y such that all amino acids $[Xaa]_x$ are located within the established surface hydrophobic patch on the peptide. Alternatively, integers w and y can be selected such that amino acids $[Xaa]_x$ do not connect two or more established hydrophobic patches in the α-helical region of the peptide. Moreover, the method can include adding to the linking group a hydrophilizing modification, including, e.g., dihydroxylation.

Another aspect of the document is a method of making any of the above-described ICL AMPs can involve: synthesizing an ICL AMP such that the ICL AMP comprises an α-helical region comprising a first surface hydrophobic patch, the replacement with the linking groups maintaining or resulting in, relative to the corresponding parent non-internally crosslinked AMP, discontinuity between the first hydrophobic patch and one or more additional surface hydrophobic patches on internally cross-linked peptide. Moreover, the method can include adding to the linking group a hydrophilizing modification, including, e.g., dihydroxylation.

Yet another feature of the document is a method of designing the any of the above-described ICL AMPs, involving:

creating one or more panels of ICL AMPs, each panel containing a plurality of panel member ICL AMPs in each of which: (a) the side chains of at least one pair of amino acids separated by 2, 3, or 6 amino acids are replaced by the linking group, $R_3$, which connects the alpha carbons of the pair of amino acids; and (b) in each member of each panel, the pair of amino acids is at different positions as compared to the other members of the relevant panel; and testing each member of all panels for (i) the presence of discontinuity between a first surface hydrophobic patch in an α-helical region of the relevant member and one or more additional surface hydrophobic patches on the α-helical region of the member; and (ii) the ability of each member of each panel for its ability to translocate into a microbial cell and lyse or inhibit the growth of a mammalian cell. The method can further involve manufacturing one or members of all the panels that have a relatively high ability to translocate into a microbial cell and no or a relatively low ability to lyse or inhibit the growth of a mammalian cell.

Yet another feature of the document is a method of identifying a microbial infection, involving:

contacting a microbial organism of the microbial infection in a test medium with any of the above-described ICL AMPs; and identifying the microbial organism by analyzing the nucleic acids released from the microbial organism into the test medium. The test medium can include a tissue sample, an organ sample, or a bodily fluid sample from a subject with the microbial infection. The medium can include culture medium to which a tissue sample, an organ sample, or a bodily fluid sample from a subject with the microbial infection had previously been added. The bodily fluid can include, e.g., blood, urine, sputum, and/or feces. The contacting can occur in vitro, or in a subject with the microbial infection. The method can further include administering to the subject containing the test medium or from which the test medium was obtained, a treatment (e.g., including any of the above-described ICL AMPs) appropriate for the identified microbial organism.

Yet another feature of the document is a method of determining whether a test medium includes a microbial organism, involving:

delivering to a medium suspected of containing a microbial organism any of the above-described ICL AMPs; and testing for the presence in the test medium of nucleic acids that the microbial organism is known to include or express. The test medium can include a tissue sample, an organ sample, or a bodily fluid sample from a subject suspected of being infected with the microbial organism. The test medium can include culture medium to which a tissue sample, an organ sample, or a bodily fluid sample from a subject suspected of being infected with the microbial organism had previously been added. The bodily fluid can include, e.g., blood, urine, sputum, and/or feces. The delivery can occur in vitro, or in a subject suspected of being infected with the microbial organism. The method can further include, if the test medium is found to contain the microbial organism, administering to the subject containing the test medium or from which the test medium was obtained, a treatment (e.g., including any of the above-described ICL AMPs) appropriate for the microbial organism.

A non-limiting example of an agent that has a "relatively high ability to inhibit the growth of a microbe" and a "relatively low ability to lyse or inhibit the growth of a mammalian cell" can have a minimum inhibitory concentration (MIC) between about 0.1 µM and about 50 or between about 0.5 µM and about 20 µM. The MIC of a compound of the invention can be about 0.1 about 0.2 about 0.3 about 0.4 µM, about 0.5 about 0.6 about 0.7 about 0.8 about 0.9 about 1 µM, about 1.1 about 1.2 about 1.3 about 1.4 about 1.5 about 1.6 µM, about 1.7 about 1.8 about 1.9 about 2 about 2.1 about 2.2 µM, about 2.3 about 2.4 about 2.5 about 2.6 about 2.7 about 2.8 µM, about 2.9 about 3 about 3.1 about 3.2 about 3.3 about 3.4 µM, about 3.5 about 3.6 about 3.7 about 3.8 about 3.9 about 4 µM, about 4.1 about 4.2 about 4.3 about 4.4 about 4.5 about 4.6 µM, about 4.7 about 4.8 about 4.9 about 5 about 5.1 about 5.2 µM, about 5.3 about 5.4 about 5.5 about 5.6 about 5.7 about 5.8 µM, about 5.9 about 6 about 6.1 about 6.2 about 6.3 about 6.4 µM, about 6.5 µM, about 6.6 µM, about 6.7 µM, about 6.8 µM, about 6.9 µM, about 7 µM, about 7.1 µM, about 7.2 µM, about 7.3 µM, about 7.4 µM, about 7.5 µM, about 7.6 µM, about 7.7 µM, about 7.8 µM, about 7.9 µM, about 8 µM, about 8.1 µM, about 8.2 µM, about 8.3 µM, about 8.4 µM, about 8.5 µM, about 8.6 µM, about 8.7 µM, about 8.8 µM, about 8.9 µM, about 9 µM, about 9.1 µM, about 9.2 µM, about 9.3 µM, about 9.4 µM, about 9.5 µM, about 9.6 µM, about 9.7 µM, about 9.8 µM, about 9.9 µM, about 10 µM, about 10.5 µM, about 11 µM, about 11.5 µM, about 12 µM, about 12.5 µM, about 13 µM, about 13.5 µM, about 14 µM, about 14.5 µM, about 15 µM, about 15.5 µM, about 16 µM, about 16.5 µM, about 17 µM, about 17.5 µM, about 18 µM, about 18.5 µM, about 19 µM, about 19.5 µM, or about 20 µM. At the MIC, the compound has hemolytic activity against human red cells, as measured in the in vitro hemolytic assay described in the Methods herein, which can be 0-10%, 5-10%, 0-5%, about 0%, about 1%, about 2%, about 3%, about 4%, about 5%, about 6%, about 7%, about 8%, about 9%, about 10%, less than 10%, less than 9%, less than 8%, less than 7%, less than 6%, less than 5%, less than 4%, less than 3%, less than 2%, or less than 1%.

This document also features a method of designing an antimicrobial peptide or stapled antimicrobial peptide (STAMP) that has improved microbial activity and/or reduced hemolytic activity relative to the unmodified antimicrobial peptide or stapled antimicrobial peptide. The method involves one or more of: (i) increasing the net positive charge of the antimicrobial peptide or stapled antimicrobial peptide (e.g., by increasing the number of basic residues, such as lysine, in the peptide, e.g., by amino acid substitution); (ii) increasing the number of histidine residues, e.g., by amino acid substitution; and/or (iii) reducing the rigid helicity of an AMP or STAMP (e.g., substituting an amino acid with D-alanine). In certain instances the AMP or STAMP has at least one (e.g., 1, 2, 3, 4, 5) histidines and/or lysines relative to the unmodified antimicrobial peptide.

As used herein, the terms "about" and "approximately" are defined as being within plus or minus 10% of a given value or state, preferably within plus or minus 5% of said value or state.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

Staples are represented by the symbol "X" in the figures and throughout the disclosure.

FIG. 1 is a chart depicting the maganin II amino acid sequence (SEQ ID NO: 1) with the positions of various staples and stitches indicated.

FIG. 2 is a depiction of the pexiganan sequence (SEQ ID NO: 2) with the positions of various staples and stitches indicated.

FIG. 9 is a depiction of the amino acid sequence of magainin II and of various magainin stapled analogues using i+3, i+4, and i+7 staples as single and/or double staples. The indicated staples are comprised of, for example, two S5 stapling amino acids to yield i, i+4 staples, one S5 and one $R_8$ couple or one $R_5$ and one S8 couple to yield i, i+7 staples, and $R_5$/S5 or $R_3$/S5 or S3/$R_5$ pairs to yield i, i+3 staples. The amino acids set forth in this figure correspond to SEQ ID NOs: 134 and 188-252, numbered consecutively.

FIG. 15A is a model depicting the hydrophobic face of magainin II. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S).

FIG. 15B is a model depicting the hydrophilic face of magainin II. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S).

FIG. 15C is a model depicting the hydrophobic face of Mag(i+4)1. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S); regions that are circled depict the hydrophobic i+4 staple position.

FIG. 15D is a model depicting the hydrophobic face of Mag(i+4)9. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S); regions that are circled depict the hydrophobic i+4 staple position.

FIG. 15E is a model depicting the hydrophobic face of Mag(i+4)16. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S); regions that are circled depict the hydrophobic i+4 staple position.

FIG. 15F is a model depicting the hydrophilic face of Mag(i+4)6. Regions colored in dark gray represent highly hydrophobic residues (I, L, F, M, B); regions colored in medium gray contain residues with relatively low hydrophobicity (G A); regions colored in light gray are charged/hydrophilic (H, K, E, N, S); regions that are circled depict the hydrophobic i+4 staple position.

FIG. 16B is a plot depicting the specificity of the interaction of magainin II stapled derivative Peptide 15 with liposomes simulating bacterial (e.g., *E. coli*) or mammalian cell membranes using hydrogen-deuterium exchange mass spectrometry.

FIG. 16C is a plot depicting the specificity of the interaction of magainin II with liposomes simulating bacterial (e.g., *E. coli*) or mammalian cell membranes using hydrogen-deuterium exchange mass spectrometry.

FIG. 17 is a depiction of the amino acid sequences of the members of a magainin II (i+4)15 lysine scan library (SEQ ID NOs: 32-48, respectively, in order of appearance). Amino acid B stands for the non-natural amino acid norleucine.

FIG. 18 is a depiction of the amino acid sequences of the members of a magainin II (i+4)15 glutamic acid scan library (SEQ ID NOs: 49-68, respectively, in order of appearance). Amino acid B stands for the non-natural amino acid norleucine.

FIG. 19 is a depiction of the amino acid sequences of the members of a magainin II (i+4)15 histidine point mutations sequences and G13 mutant analogues (SEQ ID NOs: 73-82, respectively, in order of appearance). The following symbols are defined as follows: B=Norleucine; !=2-aminoisobutyric acid; &=Hydroxyproline; a=d-Alanine; k=d-Lysine.

DETAILED DESCRIPTION

Stabilized Peptides

Figures 3A, 3B:
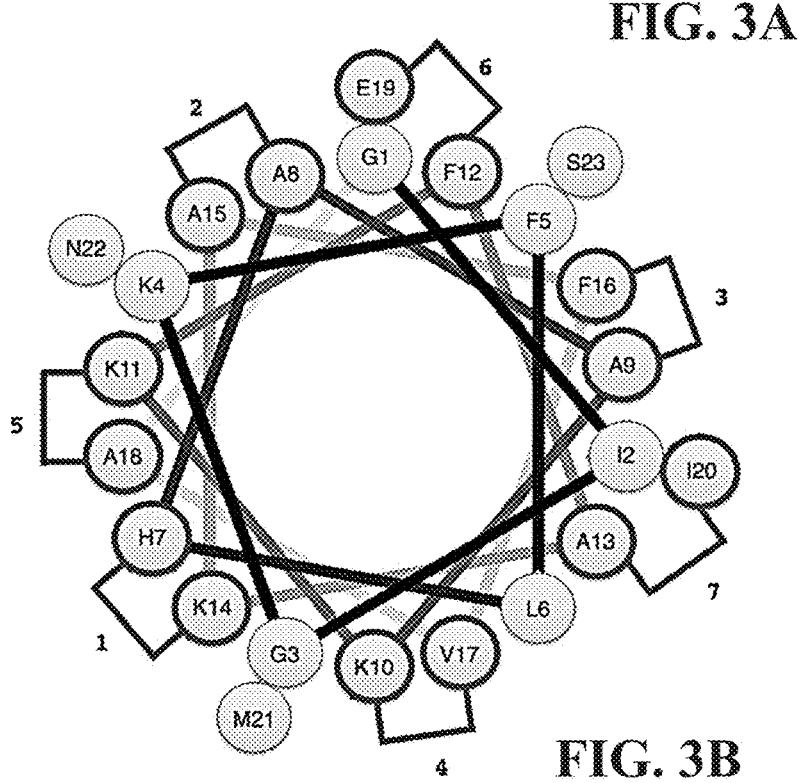
FIG. 3A is a depiction of the magainin II amino acid sequence aligned with the sequences of seven stapled derivatives to show the position of the i, i+7 staple. The amino acids set forth in this figure correspond to SEQ ID NOs: 134 and 178-184, numbered consecutively.
FIG. 3B is a helical wheel projection of the magainin II amino acid sequence (SEQ ID NO: 169) with staple positions denoted by sequence numbers. Residues A15, N22, K4, K11, A18, H7, K14, G3, M21, and K10 are the hydrophilic amino acids and residues A8, G1, E19, F12, F5, S23, F16, A9, I2, I20, A13, L6, and V17 are the hydrophobic amino acids.

The present disclosure provides structurally-stabilized and microbial-selective peptides related to anti-bacterial peptides (AMP) (referred to at times as stabilized α-helices of AMP or stabilized AMP or STAMP) comprising at least two modified amino acids joined by an internal (intramolecular) cross-link (or staple), wherein the at least two amino acids are separated by, e.g., 2, 3, or 6 amino acids. Stabilized peptides herein include stapled peptides, including peptides having, e.g., 1, 2, 3, 4, 5, or more staples and/or stitched peptides.

A compound herein can exhibit helical stability by the maintenance of α-helical structure by a compound of the invention as measured by circular dichroism or NMR. For example, in some aspects, the compound exhibits at least a 1.25, 1.5, 1.75 or 2-fold increase in α-helicity as determined by circular dichroism compared to a corresponding un-cross-linked peptide. In some aspects, the compound can exhibit about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% helicity.

Amino acids are the building blocks of the peptides herein. The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

A "peptide" or "polypeptide" comprises a polymer of amino acid residues linked together by peptide (amide) bonds. The terms, as used herein, refer to proteins, polypeptides, and peptides of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. "Dipeptide" refers to two covalently linked amino acids.

In some aspects, the present disclosure provides internally cross-linked (ICL) peptides comprising the amino acid sequence: GIGKFLHZ$_1$AKKFZ$_2$KAFVZ$_3$EIMNS (SEQ ID NO:1) wherein:

Z$_1$ is S or A and Z$_2$ and Z$_3$ are independently A or G;

the side chains of two amino acids separated by two, three, or six amino acids are replaced by an internal staple; the side chains of three amino acids are replaced by an internal stitch; the side chains of four amino acids are replaced by two internal staples, or the side chains of five amino acids are replaced by the combination of an internal staple and an internal stitch.

In some aspects, the present disclosure provides internally cross-linked polypeptides comprising the amino acid sequence:

```
                                        (SEQ ID NO: 2)
GIGKFLKKAKKFGKAFVKILKK
``` wherein:

the side chains of two amino acids separated by two, three, or six amino acids are replaced by an internal staple; the side chains of three amino acids are replaced by an internal stitch; the side chains of four amino acids are replaced by two internal staples, or the side chains of five amino acids are replaced by the combination of an internal staple and an internal stitch.

Figure 1:
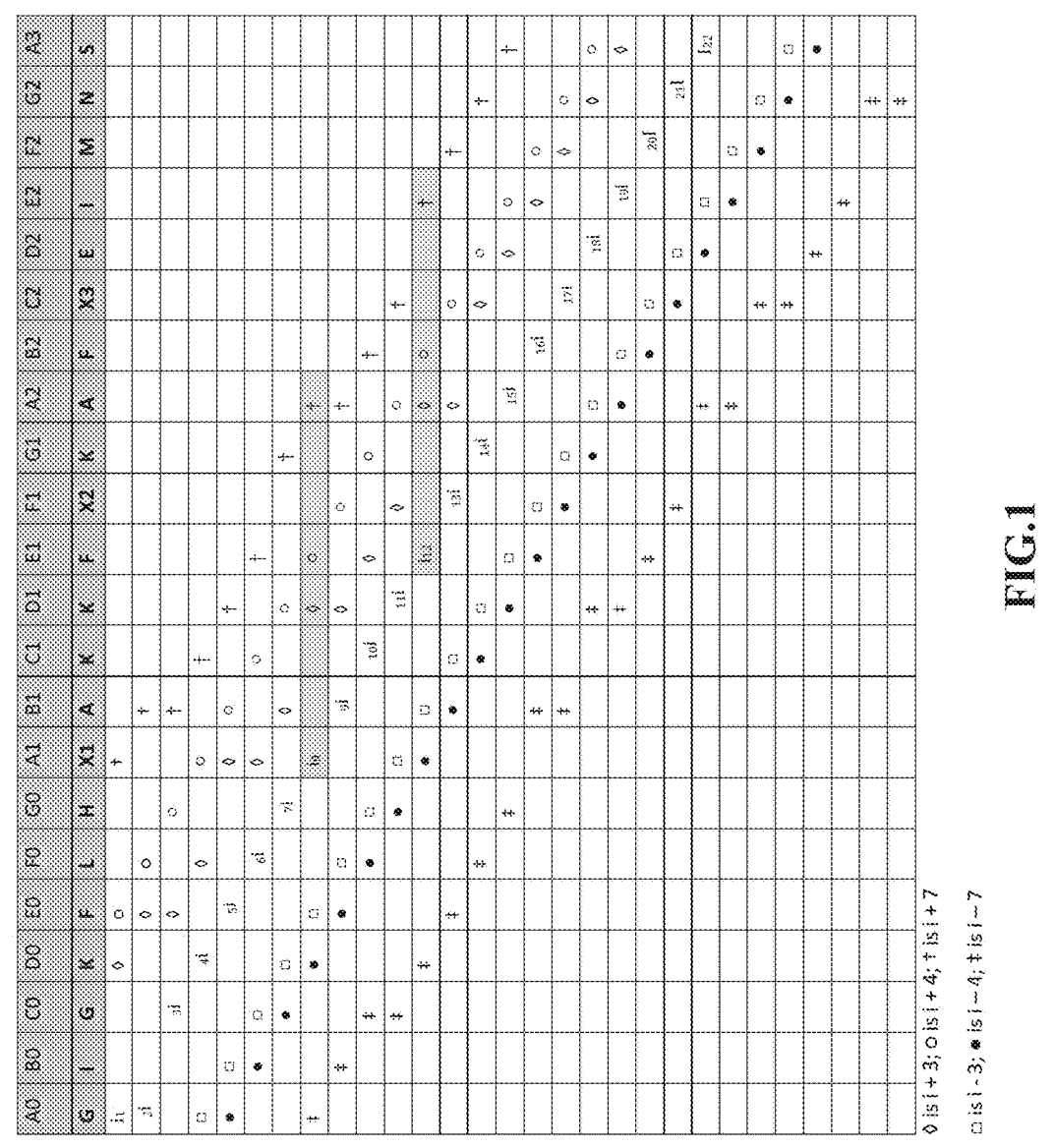

In some instances, one or more (e.g., 1, 2, 3, 4, or 5) V, F, I, or L is replaced by a non-hydrophobic amino acid. In some instances, internally cross-linked polypeptides of the disclosure include an internal staple replacing the side chains of two amino acids separated by two, three, or six amino acids comprises an internal staple selected from those depicted in FIG. 1 or FIG. 2. In some instances, the internal staples and/or the internal stitch replacing the side chains of the three amino acids includes an internal stitch selected from FIG. 1 and FIG. 2. In some instances, the internal staples and/or the internal stitch comprises at least two internal staples (replacing the side chains of 4 amino acids, i.e., each staple is between two amino acids separated by 3 amino acids). In some instances, the internal staples and/or the internal stitch comprises a combination of at least one internal staple and an internal stitch. In some instances, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some aspects, the internal stitch replacing the side chains of the three amino acids cross-links a pair of amino acids separated by two, three, or six amino acids. In some aspects, the side chains of the four amino acids of the internally cross-linked polypeptides of the disclosure are replaced by two distinct internal staples. In some aspects, a first of the two distinct internal staples cross-links a first pair of amino acids separated by two, three, or six amino acids, and a second of the at least two distinct internal staples cross-links a second pair of amino acids separated by two, three, or six amino acids.

In some instances, peptides can include (e.g., comprise, consist essentially of, or consist of) at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or more contiguous amino acids of a sequence selected from:

```
Magainin
                                        (SEQ ID NO: 3)
GIGKFLHSAKKFGKAFVGEIMNS Pexiganan
                                        (SEQ ID NO: 2)
GIGKFLKKAKKFGKAFVKILKK
```

The following additional peptides can be modified by an internal cross-link. In each case, an example of a cross-linked variant is included (X indicates an amino acid whose side chain has been replaced by an internal staple). An "—NH$_2$" at the C-terminus of a sequence indicates that the C-terminal amino acid is amidated. A "—COOH" at the C-terminus of a sequence indicates that the C-terminal amino acid is not modified.

```
Pleurocidin (Mucus Membrane of Winter Flounder)
                                        (SEQ ID NO: 4)
GWGSFFKKAAHVGKHVGKAALTHYL (SEQ ID NO: 18)
GWGSFFKKAAHXGKHVGKXALTHYL Pardaxin (Secretion from Red Sea flatfish)
                                        (SEQ ID NO: 5)
GFFALIPKIISSPLFKTLLSAVGSALSSSGEQE (SEQ ID NO: 19)
GFFALIPKIISXPLFKTLXSAVGSALSSSGEQE Hagfish Intestinal Antimicrobial Peptide (HFIAP)
                                        (SEQ ID NO: 6)
GFFKKAWRKVKHAGRRVLKKGVGRHYVNNWLK W = brominated Trp residue
```

```
(SEQ ID NO: 20)
GFFKKAWRKVKHAXRRVLKKXVGRHYVNNWLK

PGQ (Secretions from Xenopus laevis)
                                     (SEQ ID NO: 7)
GVLSNVIGYLKKLGTGALNAVLKQ (SEQ ID NO: 21)
GVLSNVIGYLKKLXTGALNAXLKQ Buforin II (Stomach Secretion from Asian Toad
Bufo bufo garagrizans)
                                     (SEQ ID NO: 8)
TRSSRAGLQFPVGRVHRLLRK (SEQ ID NO: 22)
TRSSRAGLQFPXGRVHRLXRK Dermaseptin (Skin secretion Phyllomedusa frogs)
                                     (SEQ ID NO: 9)
ALWKTMLKKLGTMALHAGKAALGAAADTISQGTQ-NH2

(SEQ ID NO: 23)
ALWKTMLKKLGTMXLHAGKAXLGAAADTISQGTQ-NH2

Caerin (Skin glands of Tree Frog Litoria chloris)
                                     (SEQ ID NO: 10)
GLFKVLGSVAKHLLPHVVPVIAEKL-NH2

(SEQ ID NO: 24)
GLFKVLGSVAKHLXPHVVPVXAEKL-NH2

Melittin
                                     (SEQ ID NO: 11)
GIGAVLKVLTTGLPALISWIKRKRQQ-NH2

(SEQ ID NO: 25)
GIGAVLKVLTTGXPALISWXKRKRQQ-NH2

Cecropin A
                                     (SEQ ID NO: 12)
KWKLFKKIEKVGQNIRDGIIKAGPAVAVVGQATQIAK-NH2

(SEQ ID NO: 26)
KWKXFKKIEKXGQNIRDGIIKAGPAVAVVGQATQIAK-NH2

Lycotoxin I
                                     (SEQ ID NO: 13)
KIKWFKTMKSIAKFIAKEQMKKHLGGE-COOH (SEQ ID NO: 27)
KIKWFKTXKSIAKFXAKEQMKKHLGGE-COOH Styelins B
                                     (SEQ ID NO: 14)
GFGPAFHSVSNFAKKHKTA-NH2

(SEQ ID NO: 28)
GFGPXFHSVSNXAKKHKTA-NH2

Clavanin B
                                     (SEQ ID NO: 15)
VFQFLGRIIHHVGNFVHGFSHVF-NH2

(SEQ ID NO: 29)
VFQFXGRIIHHXGNFVHGFSHVF-NH2

Cathelicidin A (Example below is CP-11, an
indolicidin derivative from cow stomach)
                                     (SEQ ID NO: 16)
ILKKWPWWPWRRK-NH2

(SEQ ID NO: 30)
IXKKWPWWWRRK-NH2

Dermcidin
                                     (SEQ ID NO: 17)
SSLLEKGLDGAKKAVGGLGKLGKDAVEDLESVGKGAVHDVKDVLDSVL-
COOH (SEQ ID NO: 31)
SSLLEKGLDGXKKAVGGXGKLGKDAVEDLESVGKGAVHDVKDVLDSVL-
COOH
``` wherein the peptide has a reinforced or stabilized alpha helical secondary structure (e.g., wherein the peptide includes at least one internal crosslink).

The following additional peptides in Table 1 (SEQ ID NOs:32-82, numbered consecutively from top to bottom, left column, then from top to bottom, right column) are specific magainin stapled analogues Mag(i+4)15, Mag(i+4)0, and Mag(i+4)18, and magainin double stapled analogues Mag(i+4)1,15(A9K) and Mag(i+4)2,15(A9K). The symbol "!" represents 2-aminoisobutyric acid; the symbol "&" represents hydroxyproline; the symbol "B" represents norleucine; the symbol "a" represents D-alanine; the symbol "k" represents D-lysine.

TABLE 1

| Sequences of specific magainin i + 4 stapled or double stapled analogues | | | |
|---|---|---|---|
| Mag(i + 4)15(S23K) | GIGKFLHSAKKFGKAXVGEXBNK | Mag(i + 4)15(K10E) | GIGKFLHSAEKFGKAXVGEXBNS |
| Mag(i + 4)15(N22K) | GIGKFLHSAKKFGKAXVGEXBKS | Mag(i + 4)15(K11E) | GIGKFLHSAKEFGKAXVGEXBNS |
| Mag(i + 4)15(B21K) | GIGKFLHSAKKFGKAXVGEXKNS | Mag(i + 4)15(F12E) | GIGKFLHSAKKEGKAXVGEXBNS |
| Mag(i + 4)15(E19K) | GIGKFLHSAKKFGKAXVGKXBNS | Mag(i + 4)15(G13E) | GIGKFLHSAKKFEKAXVGEXBNS |
| Mag(i + 4)15(G18K) | GIGKFLHSAKKFGKAXVKEXBNS | Mag(i + 4)15(K14E) | GIGKFLHSAKKFGEAXVGEXBNS |
| Mag(i + 4)15(V17K) | GIGKFLESAKKFGKAXKGEXBNS | Mag(i + 4)15(A15E) | GIGKFLHSAKKFGKEXVGEXBNS |
| Mag(i + 4)15(A15K) | GIGKFLHSAKKFGKKXVGEXBNS | Mag(i + 4)15(V17E) | GIGKFLHSAKKFGKAXEGEXBNS |
| Mag(i + 4)15(G13K) | GIGKFLHSAKKFKKAXVGEXBNS | Mag(i + 4)15(G18E) | GIGKFLHSAKKFGKAVEEXBNS |
| Mag(i + 4)15(F12K) | GIGKFLHSAKKKGKAXVGEXBNS | Mag(i + 4)15(B21E) | GIGKFLHSAKKFGKAXVGEXENS |
| Mag(i + 4)15(A9K) | GIGKFLHSKKFGKAXVGEXBNS | Mag(i + 4)15(N22E) | GIGKFLHSAKKFGKAXVGEXBES |
| Mag(i + 4)15(S8K) | GIGKFLHKAKKFGKAXVGEXBNS | Mag(i + 4)15(S23E) | GIGKFLHSAKKFGKAXVGEXBNE |
| Mag(i + 4)15(H7K) | GIGKFLKSAKKFGKAXVGEXBNS | Mag(i + 4)0 | XIGKXLHSAKKFGKAFVGEIBNS |
| Mag(i + 4)15(L6K) | GIGKFKHSAKKFGKAXVGEXBNS | Mag(i + 4)18 | GIGKFLHSAKKFGKAFVGXIBNX |

TABLE 1-continued

Sequences of specific magainin i + 4 stapled or double stapled analogues

| Name | Sequence | Name | Sequence |
|---|---|---|---|
| Mag(i + 4)15(F5K) | GIGKKLHSAKKFGKAXVGEXBNS | Mag(i + 4)1,15(A9K) | GXGKFXHSKKKFGKAXVGEXBNS |
| Mag(i + 4)15(G3K) | GIKKFLHSAKKFGKAXVGEXBNS | Mag(i + 4)2,15(A9K) | GIXKFLXSKKKFGKAXVGEXBNS |
| Mag(i + 4)15(I2K) | GKGKFLHSAKKFGKAXVGEXBNS | Mag(i + 4)15(G3H) | GIHKFLHSAKKFGKAXVGEXBNS |
| Mag(i + 4)15(G1K) | KIGKFLESAKKFGKAXVGEXBNS | Mag(i + 4)15(S8H) | GIGKFLHHAKKFGKAXVGEXBNS |
| Mag(i + 4)15(G1E) | EIGKFLHSAKKFGKAXVGEXBNS | Mag(i + 4)15(A15H) | GIGKFLHSAKKFGKHXVGEXBNS |
| Mag(i + 4)15(I2E) | GEGKFLHSAKKFGKAXVGEXBNS | Mag(i + 4)15(G18H) | GIGKFLHSAKKFGKAXVHEXBNS |
| Mag(i + 4)15(G3E) | GIEKFLHSAKKFGKAXVGEXBNS | Mag(i + 4)15(G13!) | GIGKFLHSAKKF**!KAXVGEX**BNS |
| Mag(i + 4)15(K4E) | GIGEFLHSAKKFGKAXVGEXBNS | Mag(i + 4)15(G13P) | GIGKFLHSAKKFPKAXVGEXBNS |
| Mag(i + 4)15(F5E) | GIGKELHSAKKFGKAXVGEXBNS | Mag(i + 4)15(G13&) | GIGKFLHSAKKF**&KAXVGEX**BNS |
| Mag(i + 4)15(L6E) | GIGKFEHSAKKFGKAXVGEXBNS | Mag(i + 4)15(G13A) | GIGKFLHSAKKFAKAXVGEXBNS |
| Mag(i + 4)15(H7E) | GIGKFLESAKKFGKAXVGEXBNS | Mag(i + 4)15(G13a) | GIGKFLHSAKKFaKAXVGEXBNS |
| Mag(i + 4)15(S8E) | GIGKFLHEAKKFGKAXVGEXBNS | Mag(i + 4)15(G13k) | GIGKFLHsAKKFkKAXVGEXBNS |
| Mag(i + 4)15(A9E) | GIGKFLHSEKKFGKAXVGEXBNS | | |

The following additional peptides in Table 2 (SEQ ID NOs:83-133, numbered consecutively from top to bottom, left column, then from top to bottom, right column) are specific magainin i+7 stapled analogues. The symbol "!" represents 2-aminoisobutyric acid; the symbol "&" represents hydroxyproline; the symbol "B" represents norleucine; the symbol "a" represents D-alanine; the symbol "k" represents D-lysine.

TABLE 2

Sequences of specific magainin i + 7 stapled or double stapled analogues

| Name | Sequence | Name | Sequence |
|---|---|---|---|
| Mag(i + 7)10(S23K) | GIGKFLHSAKXFGKAFVXEIBNK | Mag(i + 7)10(K10E) | GIGKFLHSAEXFGKAFVXEIBNS |
| Mag(i + 7)10(N22K) | GIGKFLHSAKXFGKAFVXEIBKS | Mag(i + 7)10(F12E) | GIGKFLHSAKXEGKAFVXEIBNS |
| Mag(i + 7)10(B21K) | GIGKFLHSAKXFGKAFVXEIKNS | Mag(i + 7)10(G13E) | GIGKFLHSAKXFEKAFVXEIBNS |
| Mag(i + 7)10(I20K) | GIGKFLHSAKXFGKAFVXEKBNS | Mag(i + 7)10(K14E) | GIGKFLHSAKXFGEAFVXEIBNS |
| Mag(i + 7)10(E19K) | GIGKFLHSAKXFGKAFVXKIBNS | Mag(i + 7)10(A15E) | GIGKFLHSAKXFGKEFVXEIBNS |
| Mag(i + 7)10(V17K) | GIGKFLHSAKXFGKAFKXEIBNS | Mag(i + 7)10(F16E) | GIGKFLHSAKXFGKAEVXEIBNS |
| Mag(i + 7)10(F15K) | GIGKFLHSAKXFGKAKVXEIBNS | Mag(i + 7)10(V17E) | GIGKFLHSAKXFGKAFEXEIBNS |
| Mag(i + 7)10(A14K) | GIGKFLHSAKXFGKKFVXEIBNS | Mag(i + 7)10(I20E) | GIGKFLHSAKXFGKAFVXEEBNS |
| Mag(i + 7)10(G13K) | GIGKFLHSAKXFKKAFVXEIBNS | Mag(i + 7)10(B21E) | GIGKFLHSAKXFGKAFVXEIENS |
| Mag(i + 7)10(F12K) | GIGKFLHSAKXKGKAFVXEIBNS | Mag(i + 7)10(N22E) | GIGKFLHSAKXFGKAFVXEIBES |
| Mag(i + 7)10(A9K) | GIGKFLHSKXFGKAFVXFIENS | Mag(i + 7)10(S23E) | GIGKFLHSAKXFGKAFVXEIBNE |
| Mag(i + 7)10(S8K) | GIGKFLHKAKXKATVFFXEIBNS | Mag(i + 7)15 | GIGKFLHSAKKFGKAXVGEIBNX |
| Mag(i + 7)10(H7K) | GIGKFLKSAKXGKAFFnXEIBNS | Mag(i + 7)0 | XIGKFLHXAKKFGKAFVGEIBNS |
| Mag(i + 7)10(L6K) | GIGKFKHSAKXGKAFFEXEIBNS | Mag(i + 4)1,(i + 7)10(A9K) | GXGKFXHSKKXFGKAFVXEIBNS |
| Mag(i + 7)10(F5K) | GIGKKLHSAKXFGEAFVXEIBNS | Mag(i + 4)2,(i + 7)10(A9K) | GIXKFLHSKKXFGKAFVXEIBNS |
| Mag(i + 7)10(G3K) | GIKKFLHSAKXFGKuFIXEIBNS | Mag(i + 7)10(G3H) | GIHKFLHSAKXFGKAFVXEIBNS |
| Mag(i + 7)10(I2K) | GKGKFLHSAKXFGKAFVXEIBNS | Mag(i + 7)10(S8H) | GIGKFLHHAKXFGKAFVXEIBNS |
| Mag(i + 7)10(G1K) | KIGKFLHSAKXFGKAFVXEIBNS | Mag(i + 7)10(A15H) | GIGKFLHSAKXFGKHFVXEIBNS |
| Mag(i + 7)10(G1E) | EIGKFLHSAKXFGKAFVXEIBNS | Mag(i + 7)10(G13!) | GIGKFLHSAKXF**!KAFVX**EIBNS |
| Mag(i + 7)10(I2E) | GEGKFLHSAKXFGKAFVXEIBNS | Mag(i + 7)10(G13P) | GIGKFLHSAKXFPKAFVXEIBNS |

TABLE 2-continued

Sequences of specific magainin i + 7 stapled or double stapled analogues

| | | | |
|---|---|---|---|
| Mag(i + 7)10(G3E) | GIEKFLHSAKXFGKAFVXEIBNS | Mag(i + 7)10(G13&) | GIGKFLHSAKXF&KAFVXEIBNS |
| Mag(i + 7)10(K4E) | GIGEFLHSAKXFGKAFVXEIBNS | Mag(i + 7)10(G13A) | GIGKFLHSAKXFAKAFVXEIBNS |
| Mag(i + 7)10(F5E) | GIGKELHSAKXFGKAFVXEIBNS | Mag(i + 7)10(G13a) | GIGKFLHSAKXFaKAFVXEIBNS |
| Mag(i + 7)10(L6E) | GIGKFEHSAKXFGKAFVXEIBNS | Mag(i + 7)10(G13k) | GIGKFLHSAKXFkKAFVXEIBNS |
| Mag(i + 7)10(H7E) | GIGKFLESAKXFGKAFVXEIBES | | |
| Mag(i + 7)10(S8E) | GIGKFLHEAKKFGKAFVXEIBNS | | |
| Mag(i + 7)10(A9E) | GIGKFLHSEKXFGKAFVXEIBNS | | |

As an example, the double stapled magainin analogue Mag(i+4)1,15(A9K) shown in Table 1, above, displays especially potent activity against Gram-negative bacteria (including, e.g., E. coli, P aeruginosa), yet possesses little hemolytic activity even at concentrations 8-fold higher than its MIC.

In some instances, the peptide has or can be induced to have alpha helical secondary structure.

In some cases the peptide is a modified peptide that includes 1, 2, or 3 conservative substitutions and/or 1 or 2 non-conservative substitutions and/or 1 or 2 insertions or deletions compared to the sequence:

$$\text{GIGKFLHZ}_1\text{AKKFZ}_2\text{KAFVZ}_3\text{EEVINS} \quad \text{(SEQ ID NO: 1)}$$

wherein $Z_1$ is S or A; $Z_2$ is G or A; and $Z_3$ is G or A;
wherein the peptide has a reinforced or stabilized alpha helical secondary structure (e.g., wherein the peptide includes at least one internal crosslink); and wherein the percent identity calculation includes the cross-linked amino acids and the cross-linked amino acids are considered non-conservative substitutions. In some cases, the internal cross-link replaces the side chains of two amino acids separated by 2 or 3 amino acids. In some cases, the internal cross-link replaces the side chains of two amino acids separated by 6 amino acids. In some cases, there are two internal cross-links, each replacing the side chains of a pair of amino acids separated by 3 amino acids and each cross-link being on essentially the same face of the resulting essentially alpha-helical peptide.

In some instances, the peptide is a modified peptide that includes 1, 2, 3, 4, or 5 amino acid substitutions (e.g., 1, 2, 3, 4, or 5 amino acids are replaced with A or 1, 2, 3, 4, or 5 amino acids are conservatively substituted).

In some instances, stabilized peptides can have at least 80% (e.g., 80%, 85%, 90%, 95%, 98%, 99%, 99.5%, or 100%) identity one of SEQ ID NOs:1-17 or can include one of SEQ ID NOs:1-17 with one or more (e.g., 1, 2, 3, 4, 5, 6, 7, 8, 9, 10, 11, 12, 13, 14, 15, 16, 17, 18, e.g., 1-2, 1-3, 1-4, or 1-5) conservative amino acid substitutions. In some cases the side chain of an amino acid is substituted by Formula I. In some cases, the stabilized peptide has the sequence of one SEQ ID NOs: 1-17 with one or two staples (e.g., one staple between two amino acids separated by 2 or 3 (or 6) amino acids or two staples each between two amino acids that are separated by 2 or 3 (or 6) amino acids). In addition, 1, 2, 3, 4, or 5 of the amino acids (whose side chains are not replaced with a staple) in this stabilized peptide can be replaced by a conservative substitution or can be replaced by A.

In some cases, the peptide is substituted to provide the sequence:

ZZZKZZKKZKKZZKZZZKZZKK, where Z=the native amino acid of the naturally occurring peptide (SEQ ID NO: 259).

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes can be at least 30%, at least 40%, at least 50%, at least 60%, and at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences can be accomplished using, e.g., the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described, e.g., in Altschul et al. (Nucleic Acids Res. 25:3389-3402, 1997).

As disclosed above, peptides herein include at least two modified amino acids that together form an internal (intramolecular) cross-link (or staple), wherein the at least two modified amino acids are separated by: (A) two amino acids (i.e., i, i+3, shown in FIG. 1 and FIG. 2 as ◊), (B) three amino acid (i.e., i, i+4, shown in FIG. 1 and FIG. 2 as ○), or (C) six amino acids (i.e., i, i+7, shown in FIG. 1 and FIG. 2 as †).

In the case of a cross-link between i and i+3, the cross-link can be, e.g., a $C_7$ alkylene or alkenylene. In the case of a cross-link between i and i+4, the cross-link can be, e.g., a $C_8$ alkylene or alkenylene. In the case of a cross-link between i and i+7, the cross-link can be, e.g., a $C_{11}$, $C_{12}$, or $C_{13}$ alkylene or alkenylene. When the cross-link is an alkenylene, there can one or more double bonds.

In the case of a cross-link between i and i+3, the cross-link can be, e.g., a $C_6$, $C_7$, or $C_8$ alkylene or alkenylene (e.g., a $C_6$ alkenylene having one double bond). In the case of a cross-link between i and i+4, the cross-link can be, for example, a $C_8$ alkylene or alkenylene. In the case of a cross-link between i and i+7, the cross-link can be, e.g., a $C_{11}$, $C_{12}$, or $C_{13}$ alkylene or alkenylene (e.g., a $C_{11}$ alkenylene having one double bond). When the cross-link is alkenlyene, there can be one or more double bonds. The cross-link can be optionally substituted with 1-5 substituents selected from —OH and —$NH_3$.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J Org Chem.*, 66: 5291-5302, 2001; Angew et al., *Chem Int Ed.* 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008121767 and WO 2010/068684, which are both hereby incorporated by reference in their entirety. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1, 4 triazole or 1, 5 triazole) crosslinks can be used (see, e.g., Kawamoto et al. 2012 *J Med Chem.* 55:1137; WO 2010/060112).

Stapling of a peptide using an all-hydrocarbon cross-link has been shown to help maintain its native conformation and/or secondary structure, particularly under physiologically relevant conditions (see, e.g., Schafmiester et al., *J Am Chem Soc.*, 122:5891-5892, 2000; Walensky et al., *Science*, 305:1466-1470, 2004).

Stapling the polypeptide herein by an all-hydrocarbon crosslink predisposed to have an alpha-helical secondary structure can improve stability and various pharmacokinetic properties.

Stabilized peptides herein include at least two internally cross-linked or stapled amino acids, wherein the at least two amino acids are separated, e.g., by two (i.e., i, i+3, shown in FIG. 1 and FIG. 2), three (i.e., i, i+4, shown FIG. 1 and FIG. 2), or six (i.e., i, i+7, shown in FIG. 1 and FIG. 2) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples. Examples of peptide staples are illustrated in the figures. Cross-linked peptides (e.g., stapled and/or stitched peptides) are generally referred to herein as STAMP peptides.

Alternatively or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown in FIG. 1 and FIG. 2 as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i–3, i, i–4, i, i–7 (shown in FIG. 1 and FIG. 2, i, i+3, i, i+4, i, i+7 (shown in FIG. 1 and FIG. 2, where "i" is the core amino acid). The number of amino acids on either side of the core (e.g., between the core amino acid and an amino acid cross-linked to the core) can be the same or different.

In some aspects, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as STAMP peptides. Peptides can include cross-linked amino acids at one or more of the positions illustrated in FIG. 1 and FIG. 2.

Figure 2:
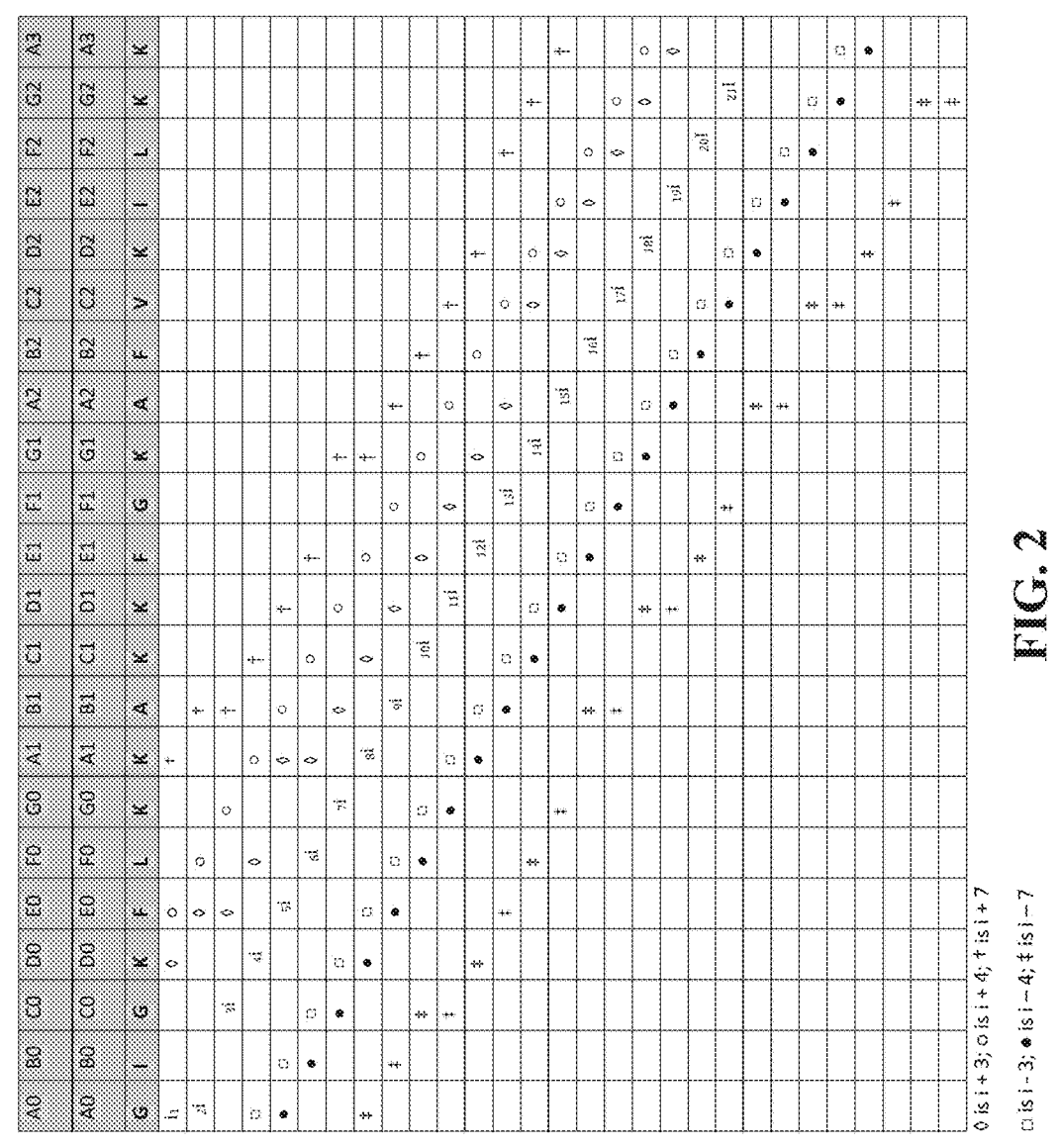

In FIG. 1 and FIG. 2 positions of cross-links are indicated by symbols and the letter "i". For example, $i_{10}$ ($C_1$) can be linked via a i+3 staple to $F_1$ or $G_0$ (also called i–3) or a i+4 staple to $G_1$ or $F_0$ (also called i–4) or a i+7 staple to $C_2$ or $C_0$ (also called i–7). Of course, $i_{10}$ ($C_1$) could be stitched to, for example $F_1$ (i+3) and $C_0$ (i–7).

Selection of amino acids for modification (e.g., to support an internal cross-link) can also be facilitated by staple scanning. The terms "staple scan" and "staple walk" refer interchangeably to the synthesis of a library of stapled peptides whereby the location of the i and i+3; i and i+4; and i and i+7 single and multiple staple, or stitches, are positioned sequentially down the length of the peptide sequence, sampling all possible positions, to identify desired, effective, suitable, or optimal properties and activities for the stapled or stitched constructs. Examples of staple scanning methods are illustrated in the figures.

Suitable tethers are described herein and in, e.g., US2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain aspects, a "terminally unsaturated amino acid side chain" is a terminal olefinic amino acid side chain. In certain aspects, a "terminally unsaturated amino acid side chain" is a terminal acetylenic amino acid side chain. In certain aspects, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking (see FIG. 1 and FIG. 2). Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (see, e.g., Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon.

Compounds

In some aspects, the stabilized peptides can have 5, 6, 7, 8, 9, 10, 11, 12, 13, 14, 15, 16, 17, 18, 19, 20, 21, 22, 23, 24, 25, 26, 27, 28, 29, or 30 amino acids.

The invention features a modified polypeptide of Formula (I),

Formula (I)

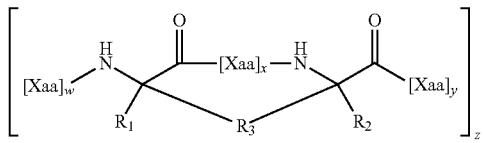

or a pharmaceutically-acceptable salt thereof, wherein;

each $R_1$ and $R_2$ are independently H, or a $C_1$ to $C_{10}$ alkyl, alkenyl, alkynyl, arylalkyl, cycloalkylalkyl, heteroarylalkyl, or heterocyclylalkyl;

each $R_3$ is alkylene, alkenylene, or alkynylene (e.g., a $C_6$, $C_7$, or $C_{11}$ alkenylene) substituted with 1-6 $R_4$;

each $R_4$ is independently —$NH_3$ or —OH, wherein each —$NH_3$ is optionally substituted;

wherein each $R_3$ replaces, relative to the corresponding parent (i.e., unmodified) non-internally cross-linked AMP, the side chains of at least one pair (e.g., one or two pairs) of amino acids separated by 2, 3, or 6 amino acids (i.e., x=2, 3, or 6).

As used above, and elsewhere in the present document, a "corresponding parent (i.e., unmodified) non-internally cross-linked AMP" can be a wild-type AMP, or any of the variants of a wild-type AMP disclosed in the present document, except that such a variant would not include an internal cross-link as described herein.

In the case of Formula I, the following aspects are among those disclosed.

In cases where x=2 (i.e., i+3 linkage), $R_3$ can be, for example, a $C_7$ alkylene, alkenylene. Where it is an alkenylene, there can one or more double bonds. In cases where x=6 (i.e., i+4 linkage), $R_3$ can be, for example, a $C_{11}$, $C_{12}$, or $C_{13}$ alkylene or alkenylene. Where it is an alkenylene there can be one or more double bonds. In cases where x=3 (i.e., i+4 linkage), $R_3$ can be, for example, a $C_8$ alkylene, alkenylene. Where it is an alkenylene, there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

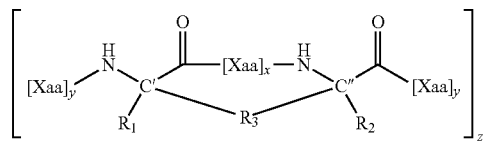

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. An $R_3$ double bond (based on the definition above, $R_3$ contains an alkane, alkene, or alkyne moiety; in general, it is an alkene) can be in the E or Z stereochemical configuration. Similar configurations are possible for the carbons in Formula II corresponding to C' and C" in the formula depicted immediately above.

In some instances, the polypeptide includes an amino acid sequence which, in addition to the amino acids side chains that are replaced by a cross-link, have 1, 2, 3, 4, 5, 6, 7, 8, 9, 10, 11, or 12 amino acid changes (e.g., conservative amino acid changes) in any of SEQ ID NOs: 1-17.

In some aspects, a compound has the Formula (II):

Formula (II)

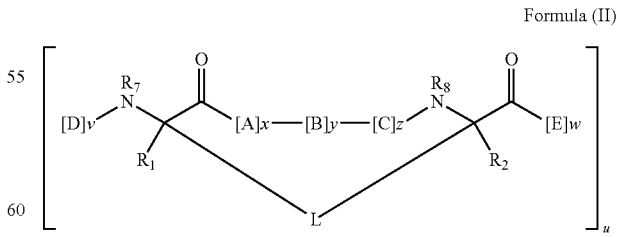

wherein:
each A, C, D, and E is independently a natural or non-natural amino acid;
each B is independently a natural or non-natural amino acid, amino acid analog,

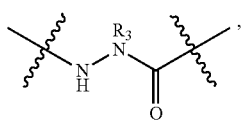

[—NH-L$_4$-CO—], [—NH-L$_4$-SO$_2$—], or [—NH-L$_4$-];

each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_1$ and the atom to which both R$_1$ and L are bound forms a ring;

each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_2$ and the atom to which both R$_2$ and L are bound forms a ring;

each R$_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

each L is independently a macrocycle-forming linker;

each L$_4$ is independently alkylene, alkenylene, alkynylene, heteroalkylene, cycloalkylene, heterocycloalkylene, arylene, heteroarylene, or [—R$_4$—K—R$_4$—]$_n$, any of which is unsubstituted or substituted;

each R$_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$;

each n is independently 1, 2, 3, 4, or 5;

each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue; each R$_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each v and w is independently an integer from 0-1000, from 1-1000, or 3-1000;

each x, y, and z is independently 0, 1, 2, 3, 4, 5, 6, 7, 8, 9, or 10; and u is 1, 2, 3, 4, 5, 6, 7, 8, 9, or 10.

In some aspects, each v and w is independently 0, 1, 2, 3, 4, 5, 6, 7, 8, 9, 10, 11, 12, 13, 14, 15, 16, 17, 18, 19, or 20. In some aspects, each w is independently an integer from 3-1000, for example, 3-500, 3-200, 3-100, 3-50, 3-30, 3-20, or 3-10. In some aspects, w is an integer from 3-10, for example 3-6, 3-8, 6-8, or 6-10. In some aspects, w is 3. In other aspects, w is 6. In some aspects, each v is independently an integer from 1-1000, for example 1-500, 1-200, 1-100, 1-50, 1-30, 1-20, or 1-10. In some aspects, v is 2. In one example, at least one of R$_1$ and R$_2$ is alkyl that is unsubstituted or substituted with halo-. In another example, both R$_1$ and R$_2$ are independently alkyl that is unsubstituted or substituted with halo-. In some aspects, at least one of R$_1$ and R$_2$ is methyl. In other aspects, R$_1$ and R$_2$ are methyl.

In some aspects, x+y+z is at least 2 or at least 3. In other aspects, x+y+z is 1, 2, 3, 4, 5, 6, 7, 8, 9 or 10. In some aspects, the sum of x+y+z is 3 or 6. In some aspects, the sum of x+y+z is 3. In other aspects, the sum of x+y+z is 6.

Each occurrence of A, B, C, D, or E in a macrocycle or macrocycle precursor is independently selected. For example, a sequence represented by the formula [A]$_x$, when x is 3, encompasses aspects where the amino acids are not identical, e.g., Gln-Asp-Ala, as well as aspects where the amino acids are identical, e.g., Gln-Gln-Gln. This applies for any value of x, y, or z in the indicated ranges. Similarly, when u is greater than 1, each compound can encompass compounds that are the same or different. For example, a compound can comprise compounds comprising different linker lengths or chemical compositions.

In some aspects, the compound comprises a secondary structure that is an α-helix where R$_8$ is —H, allowing for intrahelical hydrogen bonding. In some aspects, at least one of A, B, C, D, or E is an α,α-disubstituted amino acid. In one example, B is an α,α-disubstituted amino acid. For instance, at least one of A, B, C, D, or E is 2-aminoisobutyric acid. In other aspects, at least one of A, B, C, D, or E is

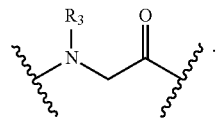

In other aspects, the length of the macrocycle-forming linker L as measured from a first Cα to a second Cα is selected to stabilize a desired secondary peptide structure, such as an α-helix formed by residues of the compound including, but not necessarily limited to, those between the first Cα to a second Cα.

In some aspects, a compound of Formula (II) has the Formula (IIa):

Formula (IIa)

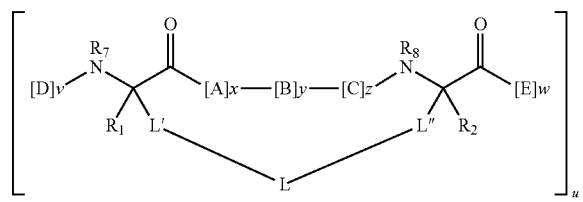

wherein:

each A, C, D, and E is independently a natural or non-natural amino acid;

each B is independently a natural or non-natural amino acid, amino acid analog,

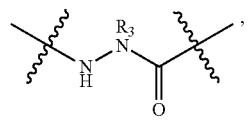

[—NH-L$_4$-CO—], [—NH-L$_4$-SO$_2$—], or [—NH-L$_4$-];

each L is independently a macrocycle-forming linker;

each L' is independently alkylene, alkenylene, alkynylene, heteroalkylene, cycloalkylene, heterocycloalkylene, arylene, or heteroarylene, any of which is unsubstituted or substituted, or a bond, or together with $R_1$ and the atom to which both $R_1$ and L' are bound forms a ring;

each L" is independently alkylene, alkenylene, alkynylene, heteroalkylene, cycloalkylene, heterocycloalkylene, arylene, or heteroarylene, any of which is unsubstituted or substituted, or a bond, or together with $R_2$ and the atom to which both $R_2$ and L" are bound forms a ring;

each $R_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both $R_1$ and L' are bound forms a ring;

each $R_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with L" and the atom to which both $R_2$ and L" are bound forms a ring;

$R_3$ is hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

each $L_4$ is independently alkylene, alkenylene, alkynylene, heteroalkylene, cycloalkylene, heterocycloalkylene, arylene, heteroarylene, or [—$R_4$—K—$R_4$—]$_n$, any of which is unsubstituted or substituted;

each $R_4$ is alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $CONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_1$ or $R_2$;

each n is independently 1, 2, 3, 4, or 5;

each $R_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each v and w is independently an integer from 0-1000, from 1-1000, or 3-1000;

each x, y, and z is independently 0, 1, 2, 3, 4, 5, 6, 7, 8, 9, or 10; and u is 1, 2, 3, 4, 5, 6, 7, 8, 9, or 10.

In some aspects, L is a macrocycle-forming linker of the formula -$L_1$-$L_2$-. In some aspects, $L_1$ and $L_2$ are independently alkylene, alkenylene, alkynylene, heteroalkylene, cycloalkylene, heterocycloalkylene, arylene, heteroarylene, or [—$R_4$—K—$R_4$-]$_n$, any of which is unsubstituted or substituted.

In one example, at least one of $R_1$ and $R_2$ is alkyl that is unsubstituted or substituted with halo-. In another example, both $R_1$ and $R_2$ are independently alkyl that is unsubstituted or substituted with halo-. In some aspects, at least one of $R_1$ and $R_2$ is methyl. In other aspects, $R_1$ and $R_2$ are methyl.

In some aspects, x+y+z is at least 2 or at least 3. In other aspects, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses aspects where the amino acids are not identical, e.g. Gln-Asp-Ala as well as aspects where the amino acids are identical, e.g. Gln-Gln-Gln. This applies for any value of x, y, or z in the indicated ranges. Similarly, when u is greater than 1, each compound may encompass moieties which are the same or different. For example, a compound may comprise moieties comprising different linker lengths or chemical compositions.

In some aspects, the compound comprises a secondary structure that is a helix where $R_8$ is —H, allowing intrahelical hydrogen bonding. In some aspects, at least one of A, B, C, D, or E is an α,α-disubstituted amino acid. In one example, B is an α,α-disubstituted amino acid. For instance, at least one of A, B, C, D, or E is 2-aminoisobutyric acid. In other aspects, at least one of A, B, C, D or E is

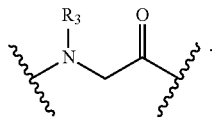

In other aspects, the length of the macrocycle-forming linker L as measured from a first Cα to a second Cα is selected to stabilize a desired secondary peptide structure, such as a helix formed by residues of the compound including, but not necessarily limited to, those between the first Cα to a second Cα.

In some aspects, the compound of Formula (II) has the Formula (IIb):

(Formula IIb)

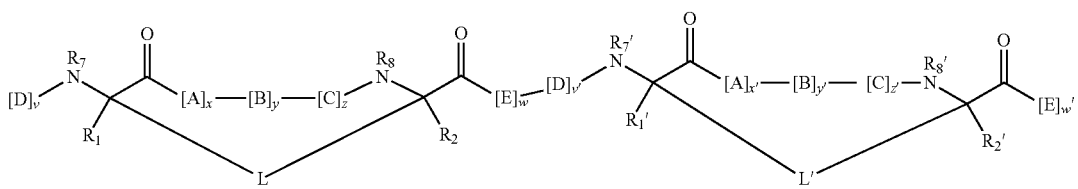

wherein:
each A, C, D, and E is independently an amino acid, wherein A, B, C, D, and E, taken together with the crosslinked amino acids connected by the macrocycle-forming linkers L and L', form the amino acid sequence of a target peptide;

each B is independently an amino acid,

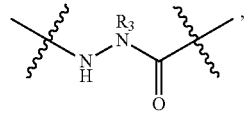

[—NH-$L_4$-CO—], [—NH-$L_4$-$SO_2$—], or [—NH-$L_4$-];

L is a macrocycle-forming linker of the formula -L₁-L₂-;

each R₁ is independently —H, alkyl, alkenyl, alkynyl, arylalkyl, cycloalkyl, cycloalkylalkyl, heteroalkyl, or heterocycloalkyl, any of which is unsubstituted or substituted, or together with L and the atom to which both R₁ and L are bound forms a ring;

each R₂ is independently —H, alkyl, alkenyl, alkynyl, arylalkyl, cycloalkyl, cycloalkylalkyl, heteroalkyl, or heterocycloalkyl, any of which is unsubstituted or substituted, or together with L and the atom to which both R₂ and L are bound forms a ring;

R₃ is hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

L' is a macrocycle-forming linker of the formula -L₁'-L₂'-;

each R₁' is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both and L' are bound forms a ring;

each R₂' is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both R₂' and L' are bound forms a ring;

L₁', L₂', and L₄ are independently alkylene, alkenylene, alkynylene, heteroalkylene, cycloalkylene, heterocycloalkylene, arylene, heteroarylene, or [—R₄—K—R₄-]ₙ, any of which is unsubstituted or substituted;

each R₄ is alkylene, alkenylene, alkynylene, heteroalkylene, cycloalkylene, heterocycloalkylene, arylene, or heteroarylene, any of which is unsubstituted or substituted;

each K is independently O, S, SO, SO₂, CO, CO₂, CONR₃, OSO₂NR₃, NR₃q, CONR₃q, OCONR₃q, or OSO₂NR₃q, wherein each R₃q is independently a point of attachment to R₁, R₂, R₁', or R₂';

each n is independently 1, 2, 3, 4, or 5;

each R₇ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each R₈ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each R₇' is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each R₈' is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each x, y and z is independently 0, 1, 2, 3, 4, 5, 6, 7, 8, 9, or 10;

each x', y' and z' is independently 0, 1, 2, 3, 4, 5, 6, 7, 8, 9, or 10;

each v and w is independently an integer from 0-1000, from 1-1000, or 3-1000;

each v' and w' is independently an integer from 0-1000, from 1-1000, or 3-1000; and each n is 1, 2, 3, 4, or 5.

In some aspects, the sum of x'+y'+z' is 1, 2, 3, 4, 5, 6, 7, 8, 9, or 10, for example 3 or 6, at least 2, or at least 3.

In some aspects, the compounds have the Formula (IIc):

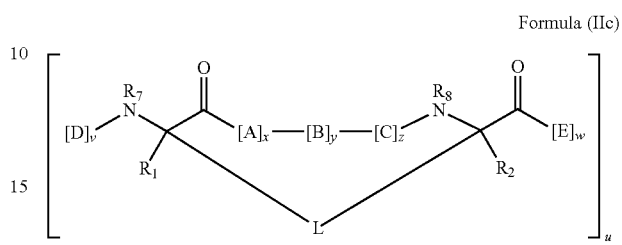

Formula (IIc)

wherein:

each A, C, D, and E is independently a natural or non-natural amino acid;

each B is independently a natural or non-natural amino acid, amino acid analog.

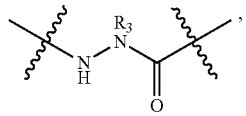

[—NH-L₄-CO—], [—NH-L₄-SO₂—], or [—NH-L₄-];

each R₁ is independently —H, alkyl, alkenyl, alkynyl, arylalkyl, cycloalkyl, cycloalkylalkyl, heteroalkyl, or heterocycloalkyl, any of which is unsubstituted or substituted, or together with R₁ and the atom to which both R₁ and L are bound forms a ring;

each R₂ is independently —H, alkyl, alkenyl, alkynyl, arylalkyl, cycloalkyl, cycloalkylalkyl, heteroalkyl, or heterocycloalkyl, any of which is unsubstituted or substituted, or together with R₂ and the atom to which both R₂ and L are bound forms a ring;

each R₃ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

each L is independently macrocycle-forming linker of the formula

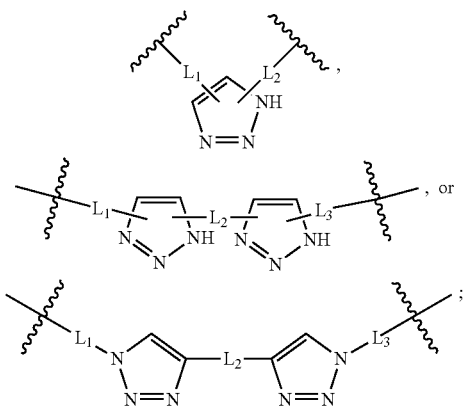

each $L_1$, $L_2$, and $L_3$ is independently alkylene, alkenylene, alkynylene, heteroalkylene, cycloalkylene, heterocycloalkylene, arylene, heteroarylene, or [—$R_4$—K—$R_4$-]$_n$, any of which is unsubstituted or substituted;

each $R_4$ is alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $CONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_1$ or $R_2$;

each $R_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each v and w is independently an integer from 0-1000, from 1-1000, or 3-1000;

each x, y and z is independently 0, 1, 2, 3, 4, 5, 6, 7, 8, 9, or 10;

u is 1, 2, 3, 4, 5, 6, 7, 8, 9, or 10; and each n is 1, 2, 3, 4, or 5.

In one example, at least one of $R_1$ and $R_2$ is alkyl that is unsubstituted or substituted with halo-. In another example, both $R_1$ and $R_2$ are independently alkyl that is unsubstituted or substituted with halo-. In some aspects, at least one of $R_1$ and $R_2$ is methyl. In other aspects, $R_1$ and $R_2$ are methyl.

In some aspects, x+y+z is at least 2 or at least 3. In other aspects, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses aspects where the amino acids are not identical, e.g. Gln-Asp-Ala as well as aspects where the amino acids are identical, e.g. Gln-Gln-Gln. This applies for any value of x, y, or z in the indicated ranges.

In some aspects, each of the first two amino acid represented by E comprises an uncharged side chain or a negatively charged side chain. In some aspects, each of the first three amino acid represented by E comprises an uncharged side chain or a negatively charged side chain. In some aspects, each of the first four amino acid represented by E comprises an uncharged side chain or a negatively charged side chain. In some aspects, one or more or each of the amino acid that is i+1, i+2, i+3, i+4, i+5, and/or i+6 with respect to E comprises an uncharged side chain or a negatively charged side chain.

In some aspects, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some aspects, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain. In some aspects, one or more or each of the amino acid that is i+1, i+2, i+3, i+4, i+5, and/or i+6 with respect to E comprises an uncharged side chain or a negatively charged side chain.

In some aspects, each w is independently an integer from 1 to 1000. For example, the first amino acid represented by E comprises a small hydrophobic side chain. In some aspects, w is between 2 and 1000. For example, the second amino acid represented by E comprises a small hydrophobic side chain. In some aspects, w is between 3 and 1000. For example, the third amino acid represented by E comprises a small hydrophobic side chain. For example, the third amino acid represented by E comprises a small hydrophobic side chain. In some aspects, w is between 4 and 1000. In some aspects, w is between 5 and 1000. In some aspects, w is between 6 and 1000. In some aspects, w is between 7 and 1000. In some aspects, w is between 8 and 1000.

In some aspects, the compound comprises a secondary structure that is a helix where $R_8$ is —H, allowing intrahelical hydrogen bonding. In some aspects, at least one of A, B, C, D, or E is an α,α-disubstituted amino acid. In one example, B is an α,α-disubstituted amino acid. For instance, at least one of A, B, C, D, or E is 2-aminoisobutyric acid. In other aspects, at least one of A, B, C, D, or E is

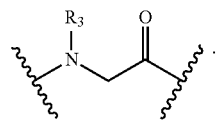

In other aspects, the length of the macrocycle-forming linker L as measured from a first Cα to a second Cα is selected to stabilize a desired secondary peptide structure, such as a helix formed by residues of the compound including, but not necessarily limited to, those between the first Cα to a second Cα.

In some aspects, L is a macrocycle-forming linker of the formula

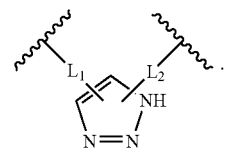

In some aspects, L is a macrocycle-forming linker of the formula

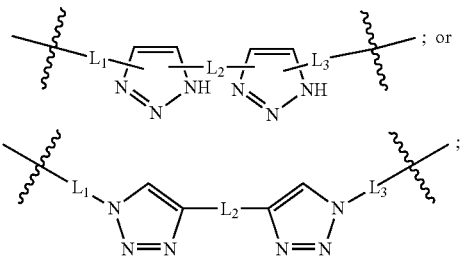

or a tautomer thereof.

Exemplary aspects of the macrocycle-forming linker L are shown below.

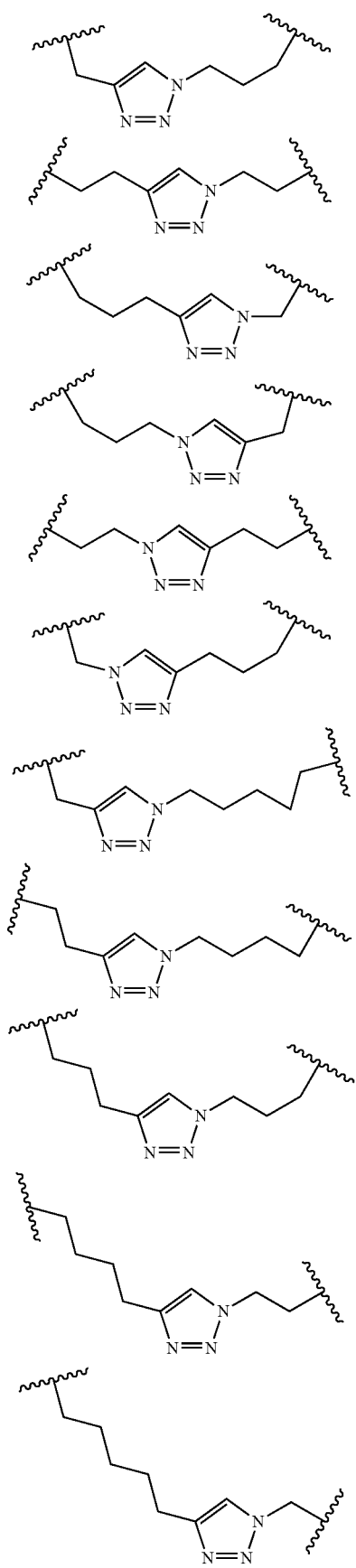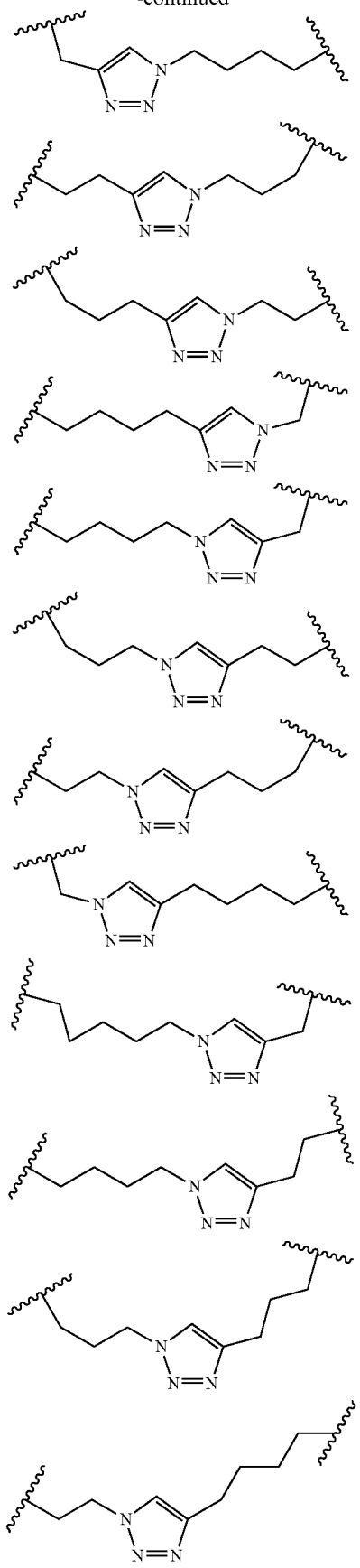

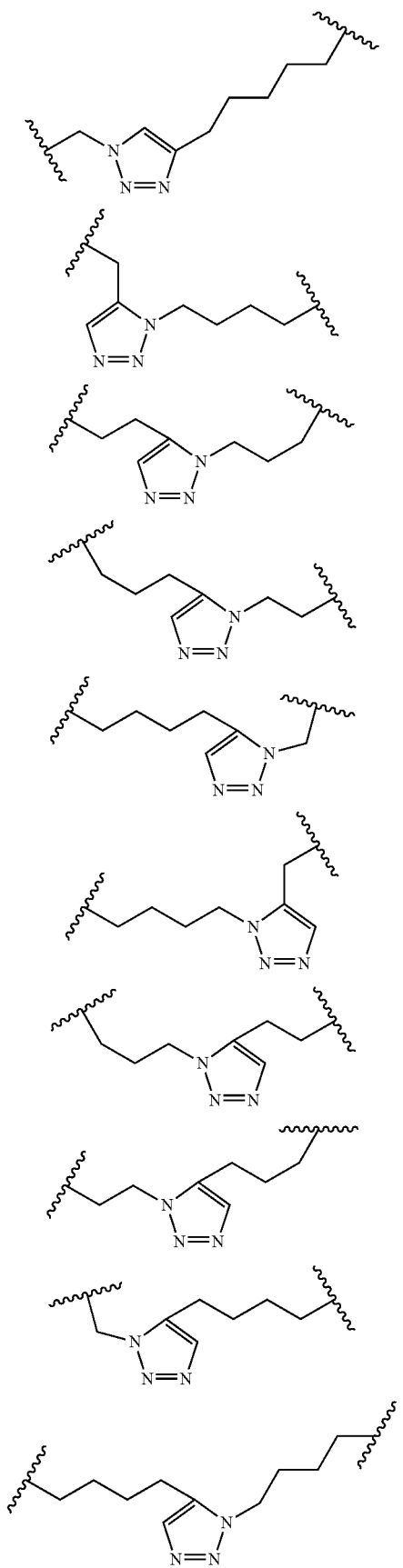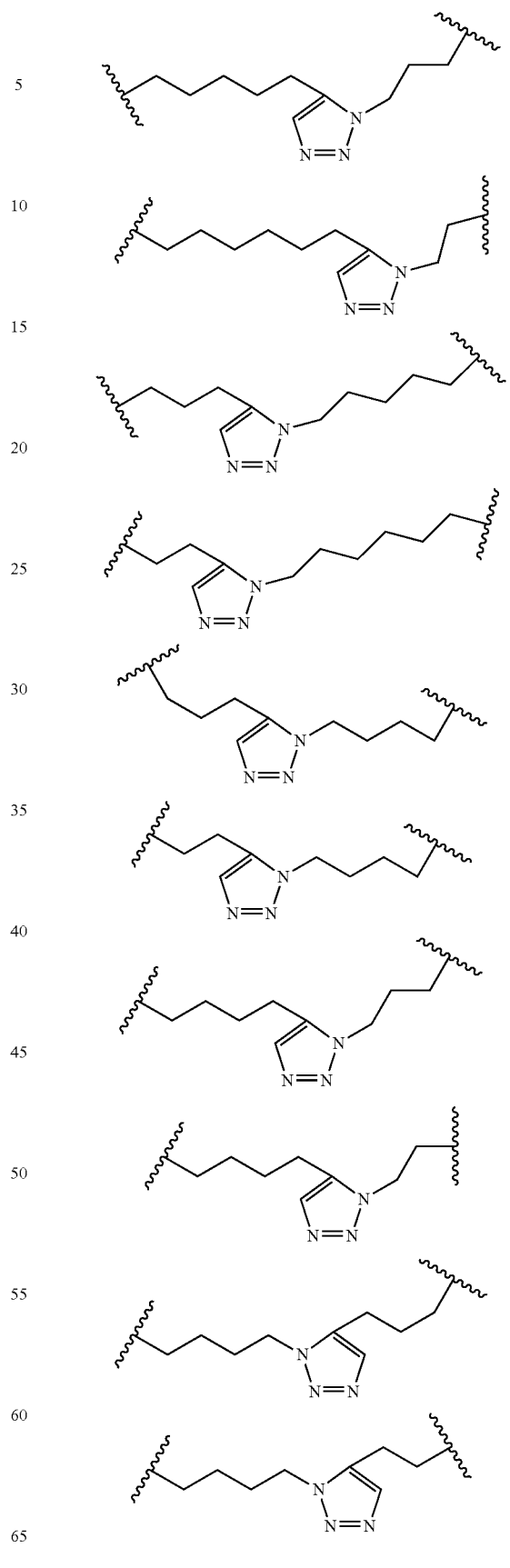

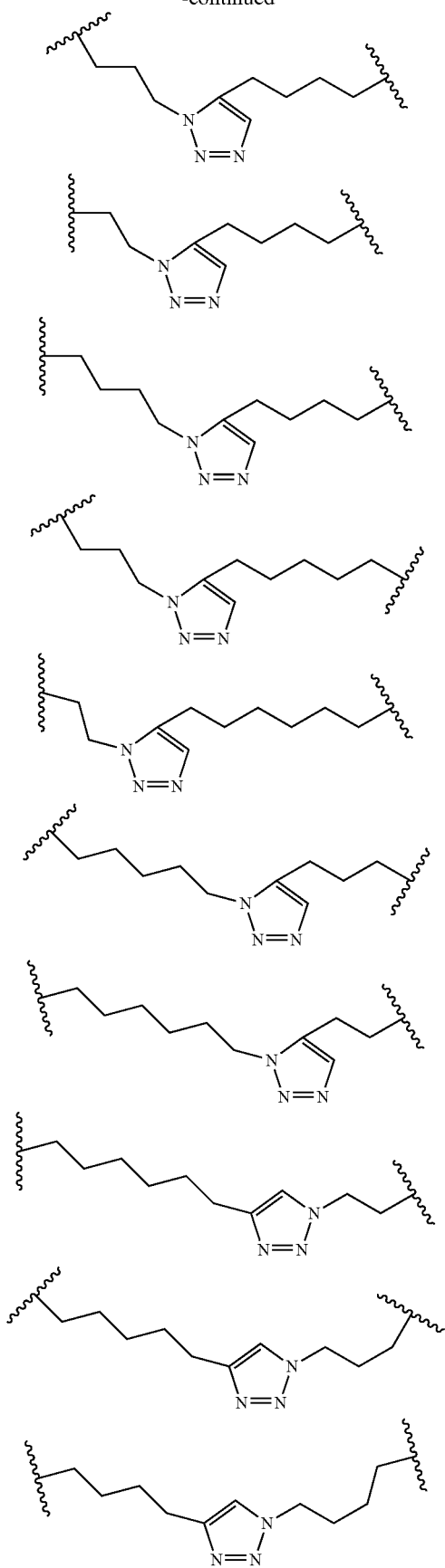
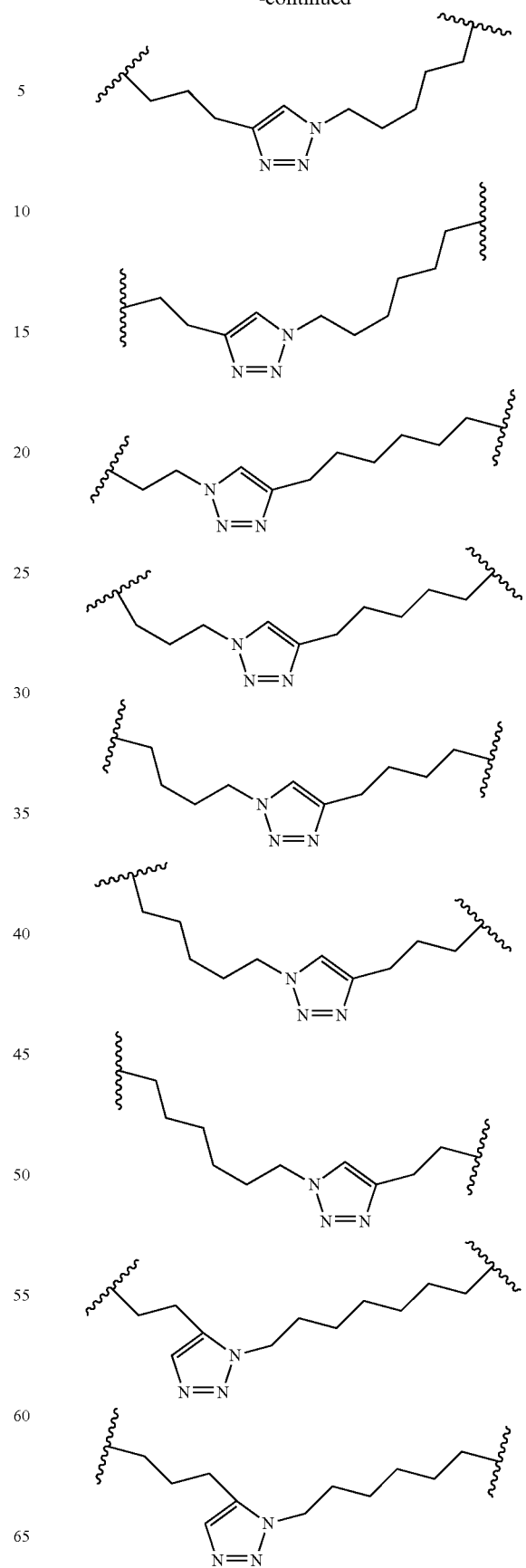

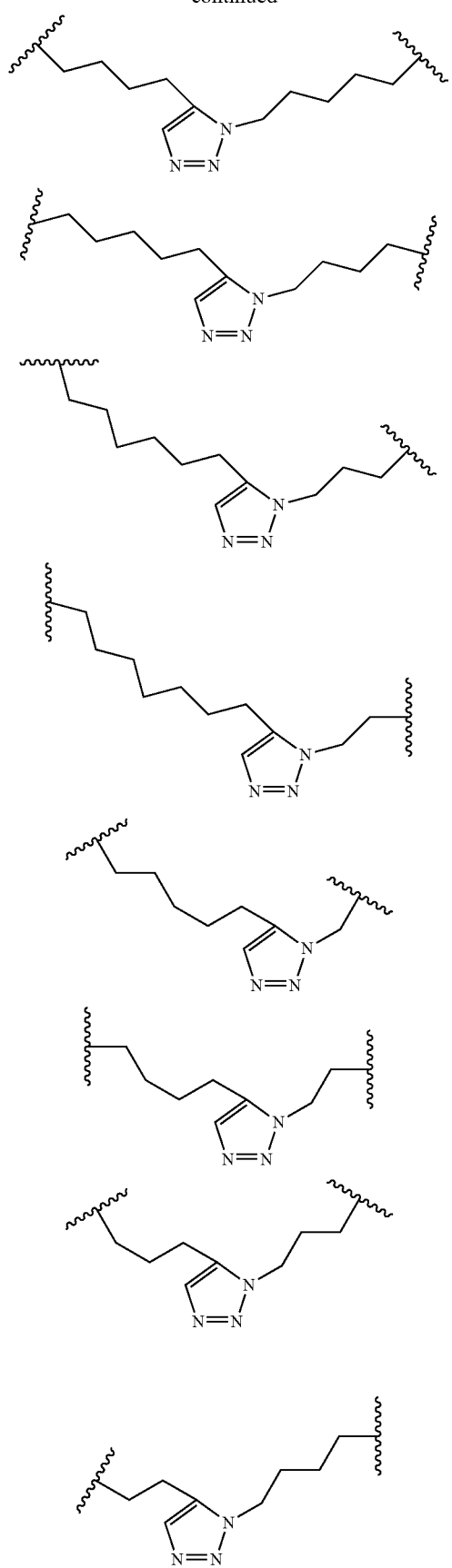
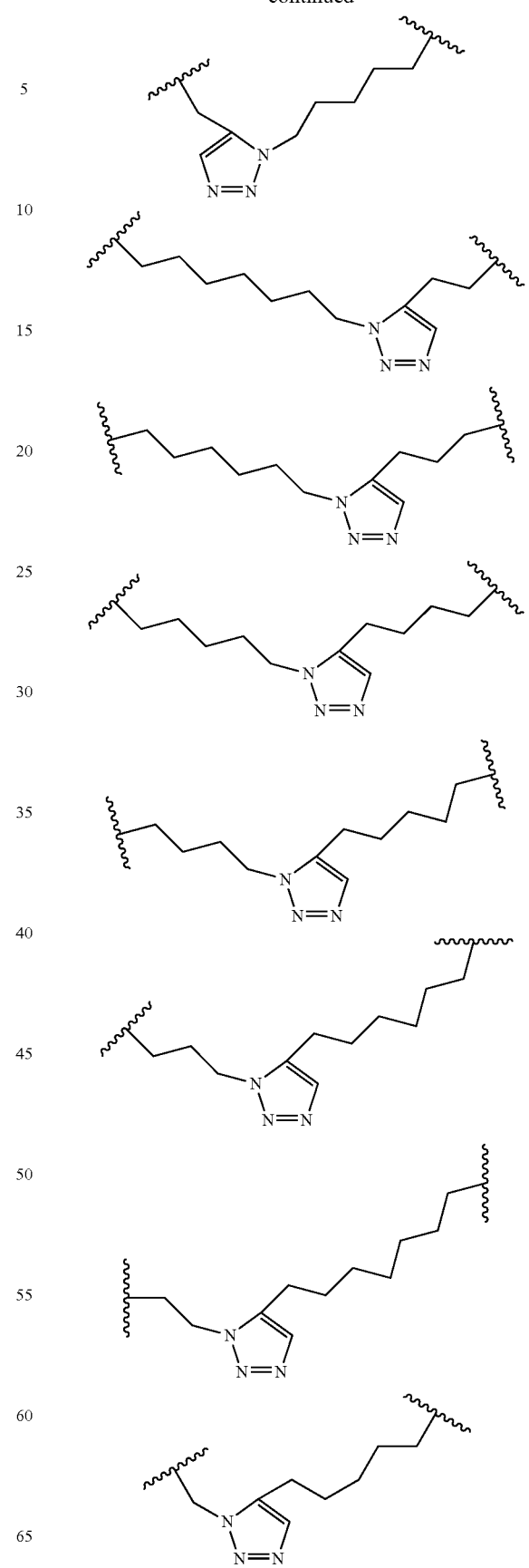

-continued

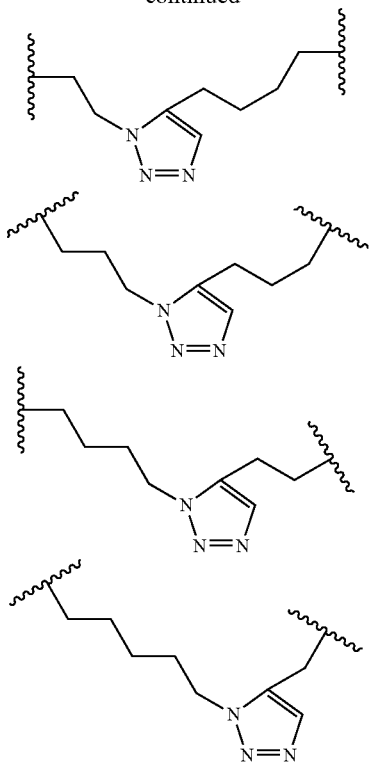

Amino acids that are used in the formation of triazole crosslinkers are represented according to the legend indicated below. Stereochemistry at the α-position of each amino acid is S unless otherwise indicated. For azide amino acids, the number of carbon atoms indicated refers to the number of methylene units between the α-carbon and the terminal azide. For alkyne amino acids, the number of carbon atoms indicated is the number of methylene units between the α-position and the triazole moiety plus the two carbon atoms within the triazole group derived from the alkyne.

| | |
|---|---|
| $5a5 | α-Me alkyne 1,5 triazole (5 carbon) |
| $5n3 | α-Me azide 1,5 triazole (3 carbon) |
| $4rn6 | α-Me R-azide 1,4 triazole (6 carbon) |
| $4a5 | α-Me alkyne 1,4 triazole (5 carbon) |

Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In any aspect herein, each v, w, v', and w' can be, independently, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In any aspect herein, each v, w, v', and w' can be, independently, 0-1000, 0-500, 0-400, 0-300, 0-200, 0-100, 0-50, 0-40, 0-30, 0-25, 0-20, 0-15, 0-10, 0-8, 0-6, 0-5, 1-1000, 1-500, 1-400, 1-300, 1-200, 1-100, 1-50, 1-40, 1-30, 1-25, 1-20, 1-15, 1-10, 1-8, 1-6, 1-5, 3-1000, 3-500, 3-400, 3-300, 3-200, 3-100, 3-50, 3-40, 3-30, 3-25, 3-20, 3-15, 3-10, 3-8, 3-6, or 3-5.

In one aspect, the compound of Formula (II) is:

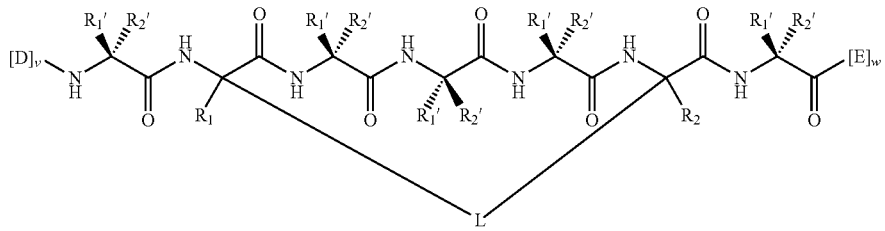

wherein each $R_1$ and $R_2$ is independently —H, alkyl, alkenyl, alkynyl, arylalkyl, cycloalkyl, cycloalkylalkyl, heteroalkyl, or heterocycloalkyl, any of which is unsubstituted or substituted.

In related aspects, the compound comprises a structure of Formula (II) which is:

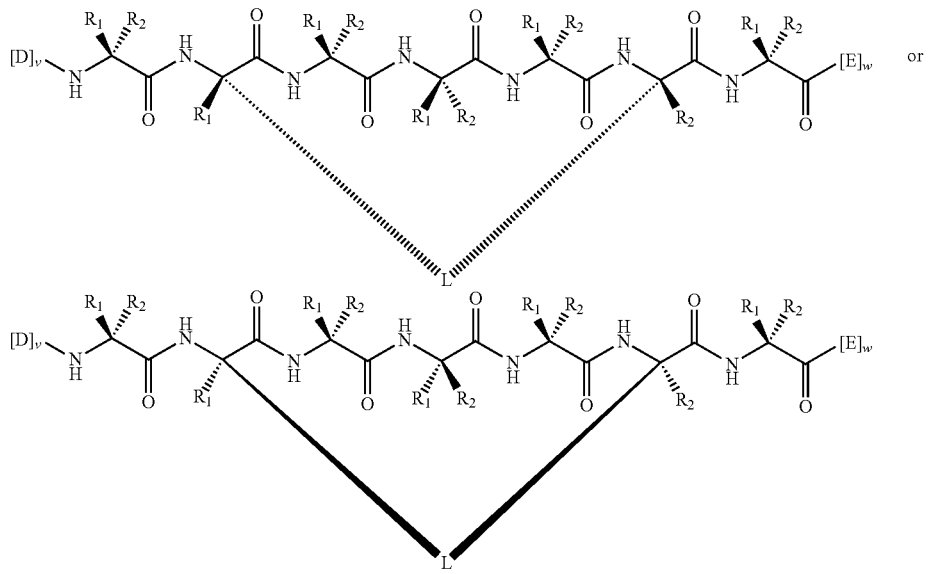

In some aspects, the compound of Formula (II) is:

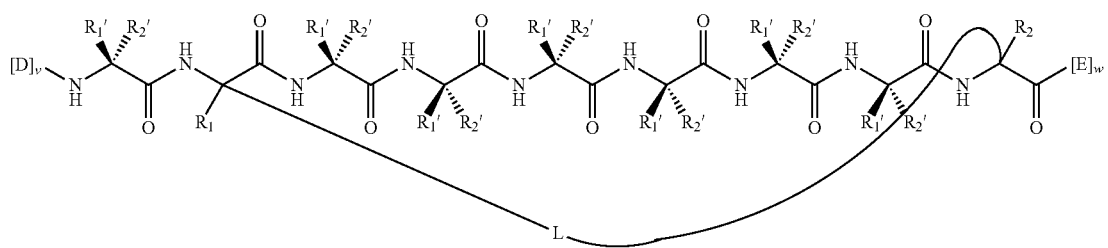

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related aspects, the compound of Formula (II) is:

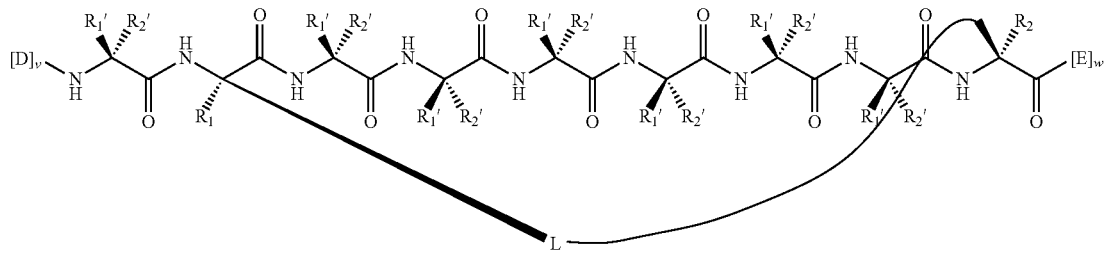

wherein each and $R_2'$ is independently an amino acid side chain.

In other aspects, the compound of Formula (II) is a compound of any of the formulas shown below:

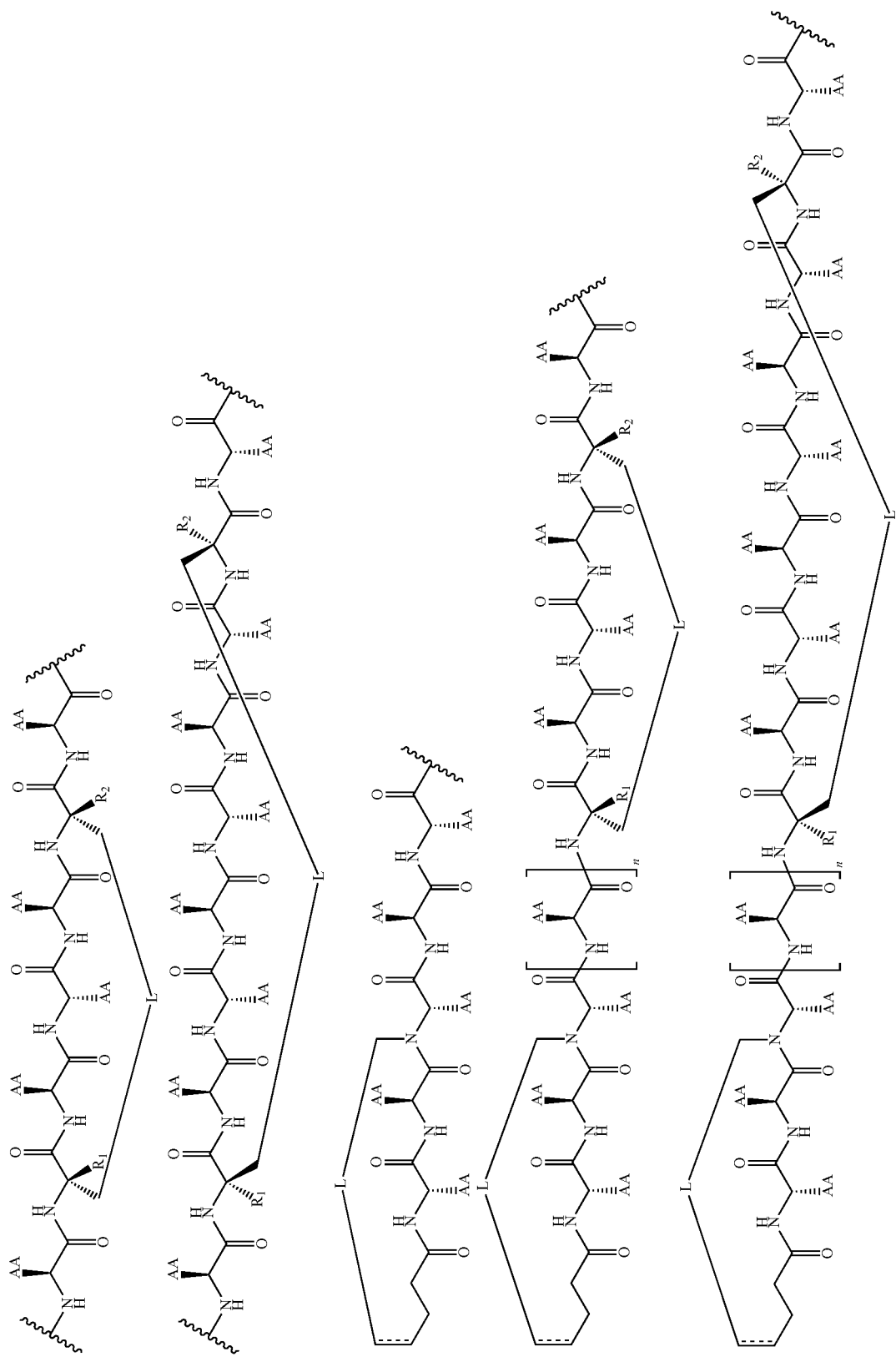

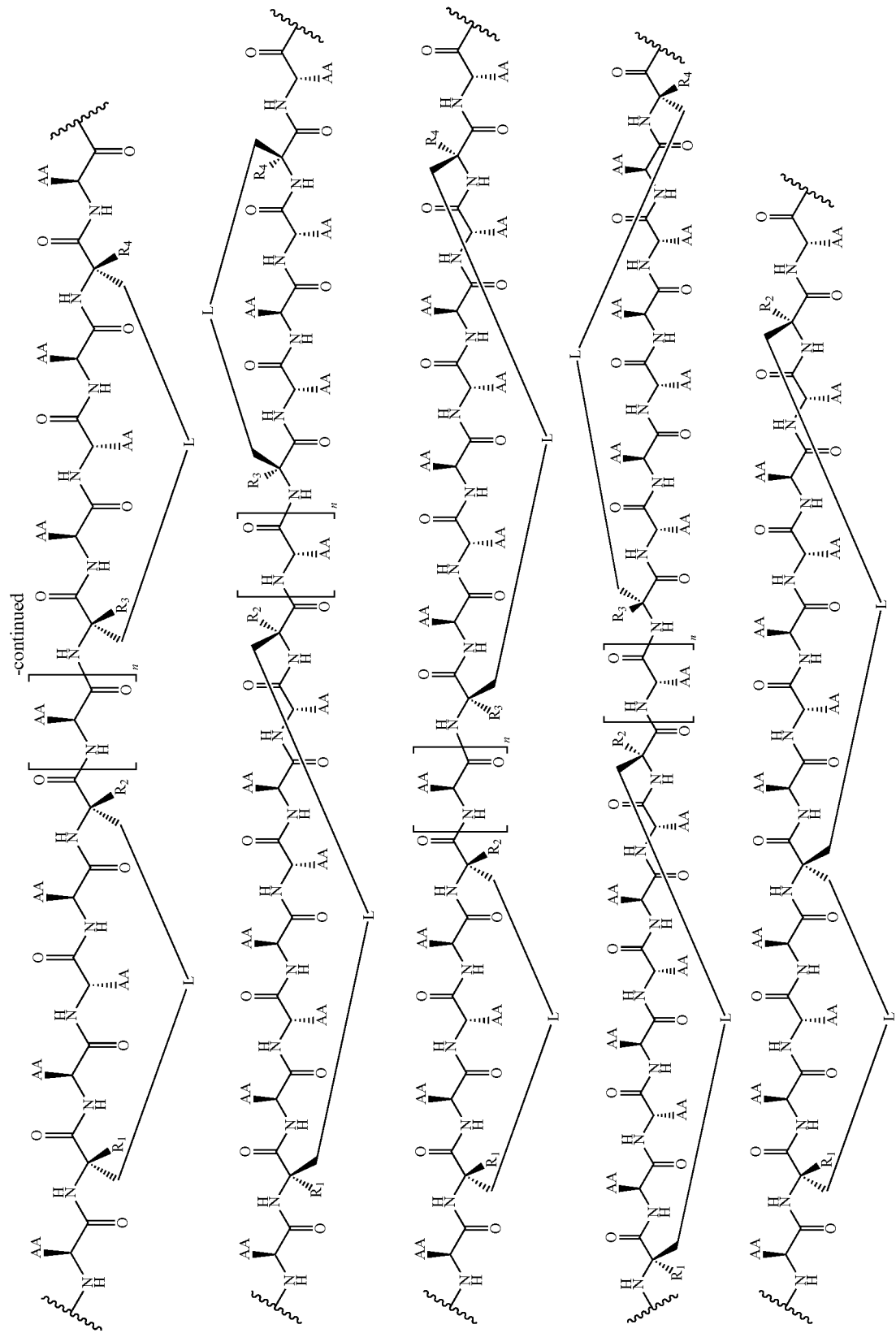

-continued
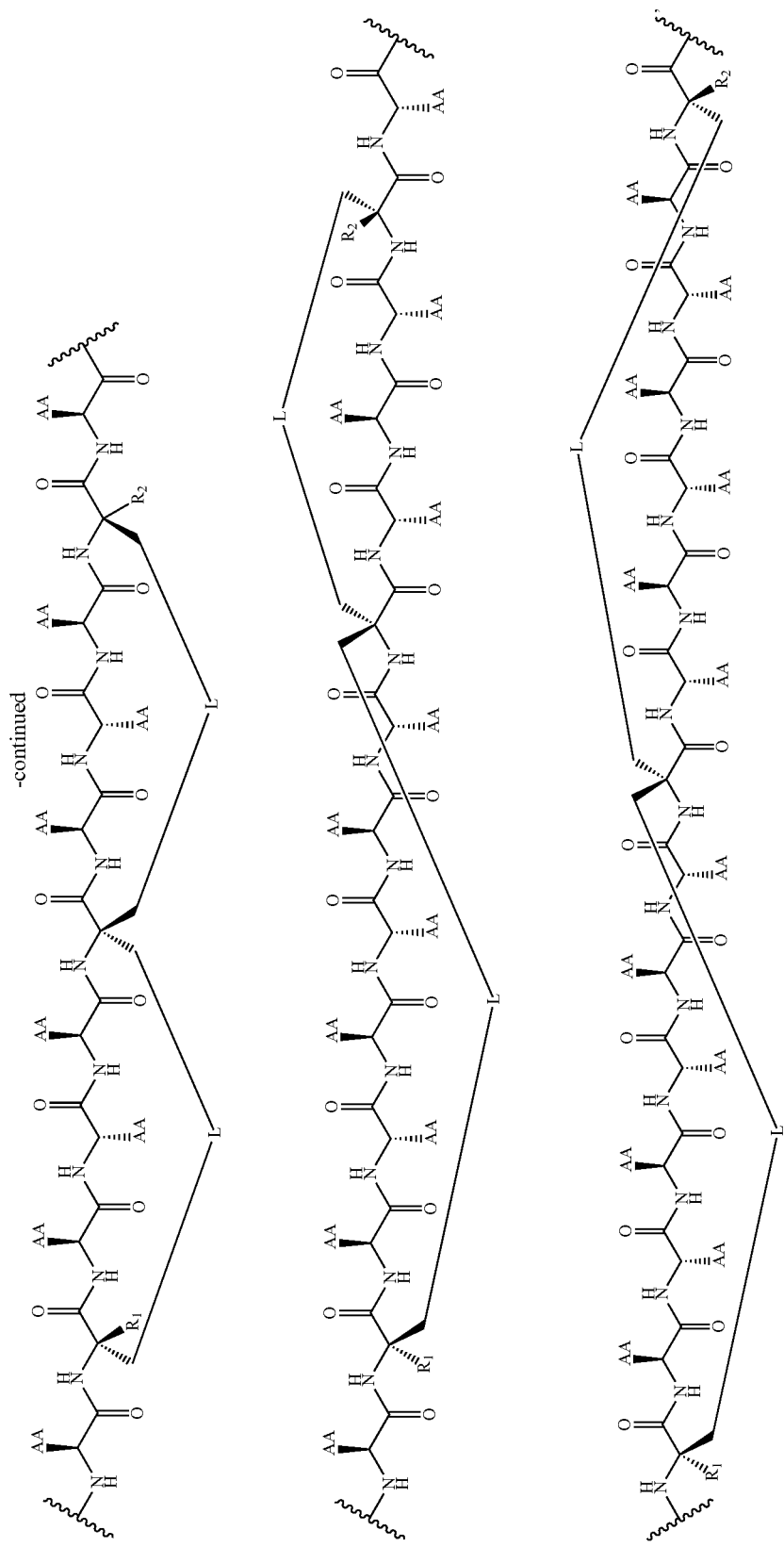

wherein "AA" represents any natural or non-natural amino acid side chain, "╱" is $[D]_v$ or $[E]_w$ as defined above, and n is an integer from 0 to 20, 50, 100, 200, 300, 400 or 500. In some aspects, the substituent "n" shown in the preceding paragraph is 0. In other aspects, the substituent "n" shown in the preceding paragraph is less than 50, 40, 30, 20, 10, or 5.

Exemplary aspects of the macrocycle-forming linker L are shown below.

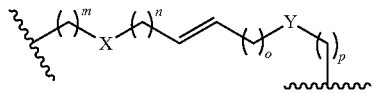

where X, Y = —CH$_2$—, O, S, or NH m, n, o, p = 0-10

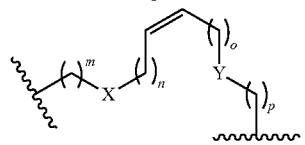

where X, Y = —CH$_2$—, O, S, or NH m, n, o, p = 0-10

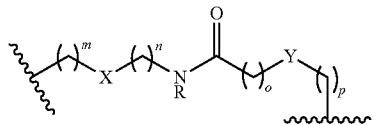

where X, Y = —CH$_2$—, O, S, or NH m, n, o, p = 0-10

R = H, alkyl, other substituent

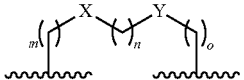

where X, Y = —CH$_2$—, O, S, or NH m, n, o, p = 0-10

In other aspects, [D] and/or [E] in the compound of Formula (II) are further modified in order to facilitate cellular uptake. In some aspects, lipidating or PEGylating a compound facilitates cellular uptake, increases bioavailability, increases blood circulation, alters pharmacokinetics, decreases immunogenicity, and/or decreases the needed frequency of administration.

In other aspects, at least one of [D] and [E] in the compound of Formula (II) represents a moiety comprising an additional macrocycle-forming linker such that the compound comprises at least two macrocycle-forming linkers. In a specific aspect, a compound comprises two macrocycle-forming linkers. In one aspect, u is 2.

In some aspects, L is a macrocycle-forming linker of the formula -L$_1$-L$_2$-. In some aspects, L$_1$ and L$_2$ are independently alkylene, alkenylene, alkynylene, heteroalkylene, cycloalkylene, heterocycloalkylene, arylene, heteroarylene, or $[—R_4—K—R_4-]_n$, any of which is unsubstituted or substituted; each R$_4$ is alkylene, alkenylene, alkynylene, heteroalkylene, cycloalkylene, heterocycloalkylene, arylene, or heteroarylene, any of which is unsubstituted or substituted; each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$; and each n is independently 1, 2, 3, 4, or 5.

In an aspect of any of the Formulas described herein, L$_1$ and L$_2$, either alone or in combination, form a triazole or a thioether.

In an aspect of any of the Formulas described herein, L$_1$ and L$_2$, either alone or in combination, do not form a triazole or a thioether.

In other aspects, the length of the macrocycle-forming linker L as measured from a first α-carbon to a second α-carbon is selected to stabilize a desired secondary peptide structure, such as a helix formed by residues of the compound including, but not necessarily limited to, those between the first α-carbon to a second α-carbon.

In one example, at least one of R$_1$ and R$_2$ is alkyl, unsubstituted or substituted with halo-. In another example, both R$_1$ and R$_2$ are independently alkyl, unsubstituted or substituted with halo-. In some aspects, at least one of R$_1$ and R$_2$ is methyl. In other aspects, R$_1$ and R$_2$ are methyl.

In some aspects, x+y+z is at least 2 or at least 3. In other aspects, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula $[A]_x$, when x is 3, encompasses aspects where the amino acids are not identical, e.g. Gln-Asp-Ala, as well as aspects where the amino acids are identical, e.g. Gln-Gln-Gln. This applies for any value of x, y, or z in the indicated ranges. Similarly, when u is greater than 1, each compound may encompass compounds which are the same or different. For example, a compound may comprise compounds comprising different linker lengths or chemical compositions.

In some aspects, the compound comprises a secondary structure that is a helix where R$_8$ is —H, allowing intrahelical hydrogen bonding. In some aspects, at least one of A, B, C, D, or E is an α,α-disubstituted amino acid. In one example, B is an α,α-disubstituted amino acid. For instance, at least one of A, B, C, D, or E is 2-aminoisobutyric acid. In other aspects, at least one of A, B, C, D or E is

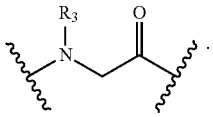

In some aspects, w is from 1 to 1000. For example, the first amino acid represented by E comprises a small hydrophobic side chain. In some aspects, w is from 2 to 1000. For example, the second amino acid represented by E comprises a small hydrophobic side chain. In some aspects, w is from 3 to 1000. For example, the third amino acid represented by E can comprise a small hydrophobic side chain. For example, the third amino acid represented by E can comprise a small hydrophobic side chain. In some aspects, w is from 4 and 1000. In some aspects, w is from 5 and 1000. In some aspects, w is from 6 and 1000. In some aspects, w is from 7 and 1000. In some aspects, w is from 8 and 1000. In some aspects, w is an integer from 3-10, for example 3-6, 3-8, 6-8, or 6-10. In some aspects, w is 3. In other aspects, w is 6. In some aspects, v is an integer from 1-10, for example 2-5. In some aspects, v is 2. In some aspects, v is 3.

In some aspects, each of the first two amino acid represented by E comprises an uncharged side chain or a negatively charged side chain. In some aspects, each of the first three amino acid represented by E comprises an uncharged side chain or a negatively charged side chain. In some aspects, each of the first four amino acid represented by E comprises an uncharged side chain or a negatively charged side chain.

In some aspects, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some aspects, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain.

In some aspects, one or more or each of the amino acid that is i+1, i+2, i+3, i+4, i+5, and/or i+6 with respect to a first E comprises an uncharged side chain or a negatively charged side chain. In some aspects, each E is independently an amino acid selected from the group consisting of Ala (alanine), D-Ala (D-alanine), Aib (α-aminoisobutyric acid), Sar (N-methyl glycine), and Ser (serine).

In other aspects, [D] and/or [E] in the compound of Formula I, Ia, Ib, or Ic are further modified in order to facilitate cellular uptake. In some aspects, lipidating or PEGylating a compound facilitates cellular uptake, increases bioavailability, increases blood circulation, alters pharmacokinetics, decreases immunogenicity and/or decreases the needed frequency of administration.

In other aspects, at least one of [D] and [E] in the compound of Formula I, Ia, Ib, or Ic represents a moiety comprising an additional macrocycle-forming linker such that the compound comprises at least two macrocycle-forming linkers. In a specific aspect, a compound comprises two macrocycle-forming linkers. In an aspect, u is 2.

In other aspects, the invention provides compounds of Formula (III):

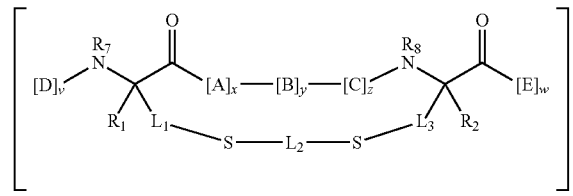

Formula (III)

wherein:
each A, C, D, and E is independently a natural or non-natural amino acid;
each B is independently a natural or non-natural amino acid, amino acid analog,

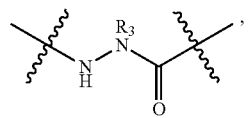

[—NH-L$_4$-CO—], [—NH-L$_4$-SO$_2$—], or [—NH-L$_4$-];
each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_1$ and the atom to which R$_1$ and L are bound forms a ring;
each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_2$ and the atom to which R$_2$ and L are bound forms a ring;
each R$_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;
each L$_1$, L$_2$, L$_3$, and L$_4$ is independently alkylene, alkenylene, alkynylene, heteroalkylene, cycloalkylene, heterocycloalkylene, arylene, heteroarylene or [—R$_4$—K—R$_4$—]$_n$, any of which is unsubstituted or substituted;
each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$;
each R$_4$ is independently alkylene, alkenylene, alkynylene, heteroalkylene, cycloalkylene, heterocycloalkylene, arylene, or heteroarylene, any of which is unsubstituted or substituted;
each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;
each R$_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;
each v and w is independently an integer from 0-1000, from 1-1000, or 3-1000;
each x, y and z is independently 0, 1, 2, 3, 4, 5, 6, 7, 8, 9, or 10;
u is 1, 2, 3, 4, 5, 6, 7, 8, 9, or 10; and
each n is independently 1, 2, 3, 4, or 5.

In some aspects, the length of the macrocycle-forming linker [-L$_1$-S-L$_2$-S-L$_3$-] as measured from a first α-carbon to a second α-carbon is selected to stabilize a desired secondary peptide structure, such as a helix (including, but not limited to a 3$_{10}$ helix or an α-helix) formed by residues of the compound including, but not necessarily limited to, those between the first α-carbon to a second α-carbon. In some aspects, the thiol moieties are the side chains of the amino acid residues L-cysteine, D-cysteine, α-methyl-L cysteine, α-methyl-D-cysteine, L-homocysteine, D-homocysteine, α-methyl-L-homocysteine, or α-methyl-D-homocysteine. A bis-alkylating reagent is of the general formula X-L$_2$-Y, wherein L$_2$ is a linker moiety and X and Y are leaving groups that are displaced by —SH moieties to form bonds with L$_2$. In some aspects, X and Y are halogens, such as I, Br, or Cl.

In other aspects, the invention provides compounds of Formula (IV) or (IVa):

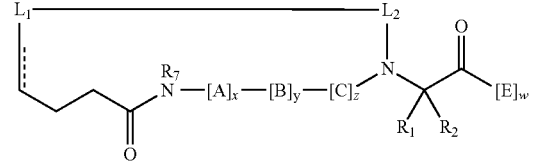

Formula (IV)

Formula (IVa)

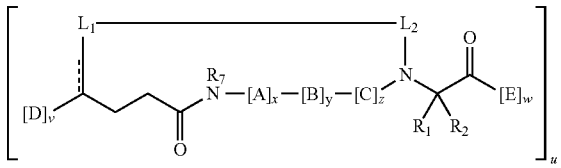

wherein:
each A, C, D, and E is independently a natural or non-natural amino acid;
each B is independently a natural or non-natural amino acid, amino acid analog.

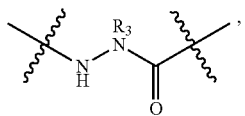

[—NH-L$_4$-CO—], [—NH-L$_4$-SO$_2$—], or [—NH-L$_4$-];
each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or part of a cyclic structure with an E residue;
each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or part of a cyclic structure with an E residue;
each R$_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;
each L is independently a macrocycle-forming linker of the formula -L$_1$-L$_2$-;
each L$_1$, L$_2$, and L$_4$ is independently alkylene, alkenylene, alkynylene, heteroalkylene, cycloalkylene, heterocycloalkylene, arylene, heteroarylene, or [—R$_4$—K—R$_4$-]$_n$, any of which is unsubstituted or substituted;
each R$_4$ is independently alkylene, alkenylene, alkynylene, heteroalkylene, cycloalkylene, heterocycloalkylene, arylene, or heteroarylene, any of which is unsubstituted or substituted;
each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$;

each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted;
each v and w is independently integers from 0-1000, from 1-1000, or 3-1000;
each x, y, and z is independently 0, 1, 2, 3, 4, 5, 6, 7, 8, 9, or 10;
u is 1, 2, 3, 4, 5, 6, 7, 8, 9, or 10; and
each n is independently 1, 2, 3, 4, 5.
In one example, L$_1$ and L$_2$, either alone or in combination, do not form a triazole or a thioether.
In one example, at least one of R$_1$ and R$_2$ is alkyl that is unsubstituted or substituted with halo-. In another example, both R$_1$ and R$_2$ are independently alkyl that is unsubstituted or substituted with halo-. In some aspects, at least one of R$_1$ and R$_2$ is methyl. In other aspects, R$_1$ and R$_2$ are methyl.
In some aspects, x+y+z is at least 1. In other aspects, x+y+z is at least 2. In other aspects, x+y+z is 1, 2, 3, 4, 5, 6, 7, 8, 9, or 10. Each occurrence of A, B, C, D, or E in a macrocycle or macrocycle precursor is independently selected. For example, a sequence represented by the formula [A]$_x$, when x is 3, encompasses aspects where the amino acids are not identical, e.g. Gln-Asp-Ala, as well as aspects where the amino acids are identical, e.g. Gln-Gln-Gln. This applies for any value of x, y, or z in the indicated ranges.
In some aspects, the compound comprises a secondary structure which is an α-helix and R$_8$ is —H, allowing intrahelical hydrogen bonding. In some aspects, at least one of A, B, C, D or E is an α,α-disubstituted amino acid. In one example, B is an α,α-disubstituted amino acid. For example, at least one of A, B, C, D, or E is 2-aminoisobutyric acid. In other aspects, at least one of A, B, C, D, or E is

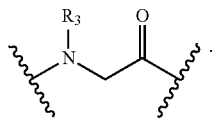

In other aspects, the length of the macrocycle-forming linker L as measured from a first Cα to a second Cα is selected to stabilize a desired secondary peptide structure, such as an α-helix formed by residues of the compound including, but not necessarily limited to, those between the first Cα to a second Cα.
In some aspects, the compound has the Formula (V) or Formula (Va):

Formula (V)

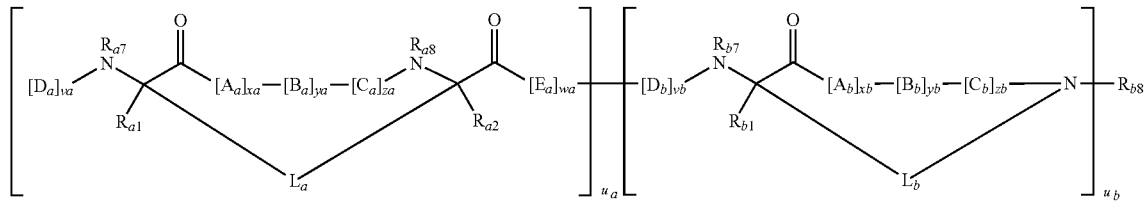

Formula (Va)

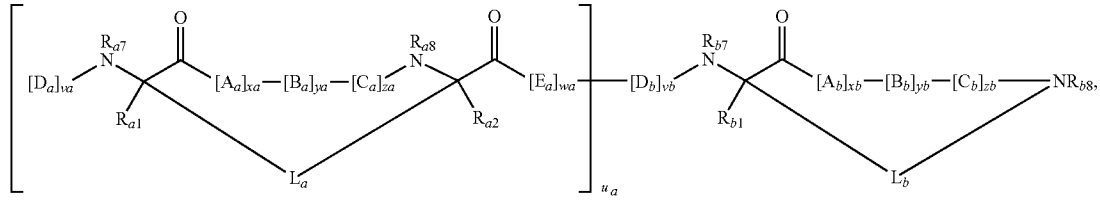

wherein:
each $A_a$, $C_a$, $D_a$, $E_a$, $A_b$, $C_b$, and $D_b$ is independently a natural or non-natural amino acid;
each $B_a$ and $B_b$ is independently a natural or non-natural amino acid,

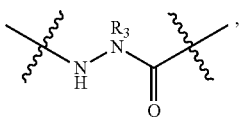

[—NH-$L_4$-CO—], [—NH-$L_4$-$SO_2$—], or [—NH-$L_4$-];
each $R_{a1}$ is independently alkyl, alkenyl, alkynyl, arylalkyl, cycloalkyl, cycloalkylalkyl, heteroalkyl, or heterocycloalkyl, any of which is unsubstituted or substituted; or H; or $R_{a1}$ forms a macrocycle-forming linker L' connected to the alpha position of one of the $D_a$ or $E_a$ amino acids; or together with $L_a$ forms a ring that is unsubstituted or substituted;
each $R_{a2}$ is independently alkyl, alkenyl, alkynyl, arylalkyl, cycloalkyl, cycloalkylalkyl, heteroalkyl, or heterocycloalkyl, any of which is unsubstituted or substituted; or H; or $R_{a2}$ forms a macrocycle-forming linker L' connected to the alpha position of one of the $D_a$ or $E_a$ amino acids; or together with $L_a$ forms a ring that is unsubstituted or substituted;
each $R_{b1}$ is independently alkyl, alkenyl, alkynyl, arylalkyl, cycloalkyl, cycloalkylalkyl, heteroalkyl, or heterocycloalkyl, any of which is unsubstituted or substituted; or H; or $R_{b1}$ forms a macrocycle-forming linker L' connected to the alpha position of one of the $D_b$ amino acids; or together with $L_b$ forms a ring that is unsubstituted or substituted;
each $R_3$ is independently alkyl, alkenyl, alkynyl, arylalkyl, heteroalkyl, cycloalkyl, heterocycloalkyl, cycloalkylalkyl, cycloaryl, or heterocycloaryl, any of which is unsubstituted or substituted, or H;
each $L_a$ is independently a macrocycle-forming linker, and optionally forms a ring with $R_{a1}$ or $R_{a2}$ that is unsubstituted or substituted;
each $L_b$ is independently a macrocycle-forming linker, and optionally forms a ring with $R_{b1}$ that is unsubstituted or substituted;
each L' is independently a macrocycle-forming linker;
each $L_4$ is independently alkylene, alkenylene, alkynylene, heteroalkylene, cycloalkylene, heterocycloalkylene, cycloarylene, heterocycloarylene, or [—$R_4$—K—$R_4$—]$_n$, any of which is unsubstituted or substituted;
each $R_4$ is independently alkylene, alkenylene, alkynylene, heteroalkylene, cycloalkylene, heterocycloalkylene, arylene, or heteroarylene, any of which is unsubstituted or substituted;
each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_{a1}$, $R_{a2}$, or $R_{b1}$;
each $R_{a7}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with a $D_a$ amino acid;
each $R_{b7}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with a $D_b$ amino acid;
each $R_{a8}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with an $E_a$ amino acid;
each $R_{b8}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or an amino acid sequence of 1-1000 amino acid residues;
each va and vb is independently an integer from 0-1000;
each wa and wb is independently an integer from 0-1000;
each ua and ub is independently 0, 1, 2, 3, 4, 5, 6, 7, 8, 9, or 10, wherein ua+ub is at least 1;
each xa and xb is independently 0, 1, 2, 3, 4, 5, 6, 7, 8, 9, or 10;
each ya and yb is independently 0, 1, 2, 3, 4, 5, 6, 7, 8, 9, or 10;
each za and zb is independently 0, 1, 2, 3, 4, 5, 6, 7, 8, 9, or 10; and
each n is independently 1, 2, 3, 4, or 5,
or a pharmaceutically-acceptable salt thereof.
In some aspects, the compound of the invention has the formula defined above, wherein:
each $L_a$ is independently a macrocycle-forming linker of the formula -$L_1$-$L_2$-, and optionally forms a ring with $R_{a1}$ or $R_{a2}$ that is unsubstituted or substituted;
each $L_b$ is independently a macrocycle-forming linker of the formula -$L_1$-$L_2$-, and optionally forms a ring with $R_{b1}$ that is unsubstituted or substituted;
each L' is independently a macrocycle-forming linker of the formula -$L_1$-$L_2$-;
each $L_1$ and $L_2$ is independently alkylene, alkenylene, alkynylene, heteroalkylene, cycloalkylene, heterocycloalkylene, cycloarylene, heterocycloarylene, or [—$R_4$—K—$R_4$—]$_n$, any of which is unsubstituted or substituted;

each $R_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_{a1}$, $R_{a2}$, or $R_{b1}$;

or a pharmaceutically-acceptable salt thereof.

In some aspects, the compound has the formula defined above wherein each $L_a$ and $L_b$ is independently a triazole-containing macrocycle-forming linker. In some aspects, the compound has the formula defined above, wherein:

each $L_a$ and $L_b$ is independently a macrocycle-forming linker of the formula:

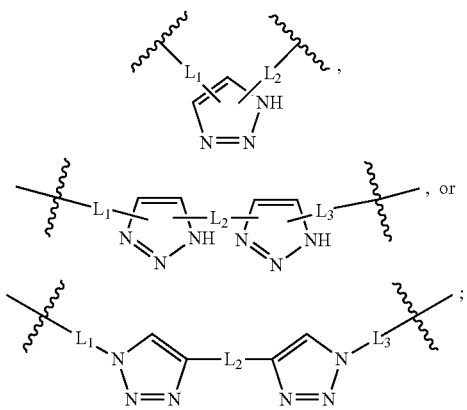

each $L_1$, $L_2$, and $L_3$ is independently alkylene, alkenylene, alkynylene, heteroalkylene, cycloalkylene, heterocycloalkylene, cycloarylene, heterocycloarylene, or $[—R_4—K—R_4—]_n$, any of which is unsubstituted or substituted;

each $R_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_{a1}$, $R_{a2}$, or $R_{b1}$; and each n is independently 1, 2, 3, 4, or 5, or a pharmaceutically-acceptable salt thereof.

In some aspects, the compound has the formula defined above, wherein:

each $L_a$ and $L_b$ is independently a macrocycle-forming linker of the formula $-L_1-SR_9R_{10}-L_2-SR_{11}R_{12}-L_3-$, wherein each $L_1$, $L_2$, and $L_3$ is independently alkylene, alkenylene, alkynylene, heteroalkylene, cycloalkylene, heterocycloalkylene, cycloarylene, heterocycloarylene, or $[—R_4—K—R_4—]_n$, any of which is unsubstituted or substituted; and each $R_9$, $R_{10}$, $R_{11}$, and $R_{12}$ is independently absent or O;

each $R_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_{a1}$, $R_{a2}$, or $R_{b1}$; and each n is independently 1, 2, 3, 4, or 5, or a pharmaceutically-acceptable salt thereof.

In some aspects, the compound has the formula defined above wherein one or both $L_a$ and $L_b$ is independently a bis-thioether-containing macrocycle-forming linker. In some aspects, each $L_a$ and $L_b$ is independently a macrocycle-forming linker of the formula $-L_1-S-L_2-S-L_3-$.

In some aspects, the compound has the formula defined above wherein one or both $L_a$ and $L_b$ is independently a bis-sulfone-containing macrocycle-forming linker. In some aspects, each $L_a$ and $L_b$ is independently a macrocycle-forming linker of the formula $-L_1-SO_2-L_2-SO_2-L_3-$.

In some aspects, the compound has the formula defined above wherein one or both $L_a$ and $L_b$ is independently a bis-sulfoxide-containing macrocycle-forming linker. In some aspects, each $L_a$ and $L_b$ is independently a macrocycle-forming linker of the formula $-L_1-S(O)-L_2-S(O)-L_3-$.

In some aspects, a compound of the invention comprises one or more secondary structures. In some aspects, the compound comprises a secondary structure that is an α-helix. In some aspects, the compound comprises a secondary structure that is a β-hairpin turn.

In some aspects, $u_a$ is 0. In some aspects, $u_a$ is 0, and $L_b$ is a triazole-containing macrocycle-forming linker that crosslinks an α-helical secondary structure. In some aspects, $u_a$ is 0, and $L_b$ is a hydrocarbon-containing macrocycle-forming linker that crosslinks an α-helical secondary structure.

In some aspects, $u_b$ is 0. In some aspects, $u_b$ is 0, and $L_a$ is a triazole-containing macrocycle-forming linker that crosslinks an α-helical secondary structure. In some aspects, $u_b$ is 0, and $L_a$ is a hydrocarbon-containing macrocycle-forming linker that crosslinks an α-helical secondary structure.

In some aspects, the compound comprises only α-helical secondary structures.

In other aspects, the compound comprises a combination of secondary structures, wherein the secondary structures are α-helical and β-hairpin structures. In some aspects, $L_a$ and $L_b$ are a combination of hydrocarbon-, triazole, or sulfur-containing macrocycle-forming linkers. In some aspects, the compound comprises $L_a$ and $L_b$, wherein $L_a$ is a hydrocarbon-containing macrocycle-forming linker that crosslinks a β-hairpin structure, and $L_b$ is a triazole-containing macrocycle-forming linker that crosslinks an α-helical structure. In some aspects, the compound comprises $L_a$ and $L_b$, wherein $L_a$ is a hydrocarbon-containing macrocycle-forming linker that crosslinks an α-helical structure, and $L_b$ is a triazole-containing macrocycle-forming linker that crosslinks a β-hairpin structure. In some aspects, the compound comprises $L_a$ and $L_b$, wherein $L_a$ is a triazole-containing macrocycle-forming linker that crosslinks an α-helical structure, and $L_b$ is a hydrocarbon-containing macrocycle-forming linker that crosslinks a β-hairpin structure. In some aspects, the compound comprises $L_a$ and $L_b$, wherein $L_a$ is a triazole-containing macrocycle-forming linker that crosslinks a β-hairpin structure, and $L_b$ is a hydrocarbon-containing macrocycle-forming linker that crosslinks an α-helical structure.

In some aspects, $u_a+u_b$ is at least 1. In some aspects, $u_a+u_b=2$.

In some aspects, $u_a$ is 1, and $u_b$ is 1. In some aspects, $u_a$ is 1, $u_b$ is 1, $L_a$ is a triazole-containing macrocycle-forming linker that crosslinks an α-helical secondary structure, and $L_b$ is a triazole-containing macrocycle-forming linker that crosslinks an α-helical secondary structure. In some aspects, $u_a$ is 1, $u_b$ is 1, $L_a$ is a triazole-containing macrocycle-forming linker that crosslinks an α-helical secondary structure, and $L_b$ is a triazole-containing macrocycle-forming linker that crosslinks a β-hairpin secondary structure. In some aspects, $u_a$ is 1, $u_b$ is 1, $L_a$ is a triazole-containing macrocycle-forming linker that crosslinks a β-hairpin secondary structure, and $L_b$ is a triazole-containing macrocycle-forming linker that crosslinks an α-helical secondary structure.

In some aspects, $u_a$ is 1, $u_b$ is 1, $L_a$ is a triazole-containing macrocycle-forming linker that crosslinks an α-helical secondary structure, and $L_b$ is a hydrocarbon-containing macrocycle-forming linker that crosslinks an α-helical structure. In some aspects, $u_a$ is 1, $u_b$ is 1, $L_a$ is a triazole-containing macrocycle-forming linker that crosslinks an α-helical secondary structure, and $L_b$ is a hydrocarbon-containing macrocycle-forming linker that crosslinks a β-hairpin structure. In some aspects, $u_a$ is 1, $u_b$ is 1, $L_a$ is a triazole-containing macrocycle-forming linker that crosslinks a β-hairpin secondary structure, and $L_b$ is a hydrocarbon-containing macrocycle-forming linker that crosslinks an α-helical structure.

In some aspects, $u_a$ is 1, $u_b$ is 1, $L_a$ is a hydrocarbon-containing macrocycle-forming linker that crosslinks an α-helical secondary structure, and $L_b$ is a triazole-containing macrocycle-forming linker that crosslinks an α-helical secondary structure. In some aspects, $u_a$ is 1, $u_b$ is 1, $L_a$ is a hydrocarbon-containing macrocycle-forming linker that crosslinks an α-helical secondary structure, and $L_b$ is a triazole-containing macrocycle-forming linker that crosslinks a β-hairpin secondary structure. In some aspects, $u_a$ is 1, $u_b$ is 1, $L_a$ is a hydrocarbon-containing macrocycle-forming linker that crosslinks a β-hairpin secondary structure, and $L_b$ is a triazole-containing macrocycle-forming linker that crosslinks an α-helical secondary structure.

In some aspects, $u_a$ is 1, $u_b$ is 1, $L_a$ is a triazole-containing macrocycle-forming linker that crosslinks an α-helical secondary structure, and $L_b$ is a sulfur-containing macrocycle-forming linker.

In some aspects, $u_a$ is 1, $u_b$ is 1, $L_a$ is a sulfur-containing macrocycle-forming linker, and $L_b$ is a triazole-containing macrocycle-forming linker with an α-helical secondary structure.

In some aspects, $u_a$ is 1, $u_b$ is 1, $L_a$ is a hydrocarbon-containing macrocycle-forming linker with an α-helical secondary structure, and $L_b$ is a sulfur-containing macrocycle-forming linker.

In some aspects, $u_a$ is 1, $u_b$ is 1, $L_a$ is a sulfur-containing macrocycle-forming linker, and $L_b$ is a hydrocarbon-containing macrocycle-forming linker with an α-helical secondary structure.

In some aspects, $u_a$ is 1, $u_b$ is 1, $L_a$ is a sulfur-containing macrocycle-forming linker, and $L_b$ is a sulfur-containing macrocycle-forming linker.

In some aspects, $u_a$ is 1, $u_b$ is 1, $L_a$ is a hydrocarbon-containing macrocycle-forming linker that crosslinks an α-helical structure, and $L_b$ is a hydrocarbon-containing macrocycle-forming linker that crosslinks an α-helical structure. In some aspects, $u_a$ is 1, $u_b$ is 1, $L_a$ is a hydrocarbon-containing macrocycle-forming linker that crosslinks an α-helical structure, and $L_b$ is a hydrocarbon-containing macrocycle-forming linker that crosslinks a β-hairpin structure. In some aspects, $u_a$ is 1, $u_b$ is 1, $L_a$ is a hydrocarbon-containing macrocycle-forming linker that crosslinks a β-hairpin structure, and $L_b$ is a hydrocarbon-containing macrocycle-forming linker that crosslinks an α-helical structure.

In some aspects, $R_{b1}$ is H.

In some aspects, each v and w is 0, 1, 2, 3, 4, 5, 6, 7, 8, 9, 10, 11, 12, 13, 14, 15, 16, 17, 18, 19, or 20. In some aspects, w is an integer from 3-1000, for example 3-500, 3-200, 3-100, 3-50, 3-30, 3-20, or 3-10. In some aspects, the sum of x+y+z is 3 or 6. In some aspects, the sum of x+y+z is 3. In other aspects, the sum of x+y+z is 6.

Unless otherwise stated, any compounds (including compounds, macrocycle precursors, and other compositions) are also meant to encompass compounds which differ only in the presence of one or more isotopically enriched atoms. For example, compounds having the described structures except for the replacement of a hydrogen by a deuterium or tritium, or the replacement of a carbon by $^{13}$C- or $^{14}$C-enriched carbon are within the scope of this disclosure.

In some aspects, the compounds disclosed herein can contain unnatural proportions of atomic isotopes at one or more of atoms that constitute such compounds. For example, the compounds can be radiolabeled with radioactive isotopes, such as for example tritium ($^3$H), iodine-125 ($^{125}$I) or carbon-14 ($^{14}$C). In other aspects, one or more carbon atoms are replaced with a silicon atom. All isotopic variations of the compounds disclosed herein, whether radioactive or not, are contemplated herein.

A compound described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis. Purity can be assessed, e.g., by HPLC, MS, LC/MS, melting point, or NMR.

Two or more peptides can share a degree of homology. A pair of peptides can have, for example, up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology. A pair of peptides can have, for example, at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology.

Various methods and software programs can be used to determine the homology between two or more peptides, such as NCBI BLAST, Clustal W, MAFFT, Clustal Omega, AlignMe, Praline, or another suitable method or algorithm.

In some aspects, the compound comprises at least one helical motif, such as a $3_{10}$ or an α-helix motif. For example, A, B, and/or C in the compound of Formula I, II, or III include one or more helices. As a general matter, helices include from 3 to 4 amino acid residues per turn. In some aspects, the helix of the compound includes 1 to 5 turns and, therefore, 3 to 20 amino acid residues. In specific aspects, the helix includes 1 turn, 2 turns, 3 turns, 4 turns, or 5 turns. In some aspects, the macrocycle-forming linker stabilizes a helix motif included within the compound. Thus, in some aspects, the length of the macrocycle-forming linker L from a first α-carbon to a second α-carbon is selected to increase the stability of a helix. In some aspects, the macrocycle-forming linker spans from 1 turn to 5 turns of the helix. In some aspects, the macrocycle-forming linker spans approximately 1 turn, 2 turns, 3 turns, 4 turns, or 5 turns of the helix. In some aspects, the length of the macrocycle-forming linker is approximately 5 Å to 9 Å per turn of the helix, or approximately 6 Å to 8 Å per turn of the helix. Where the macrocycle-forming linker spans approximately 1 turn of a helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of a helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of a helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of a helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of a helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of a helix, the linkage contains approximately 4 atoms to 12 atoms, approximately 6 atoms to 10 atoms, or approximately 8 atoms. Where the macrocycle-forming linker spans approximately 2 turns of the helix, the linkage contains approximately 7 atoms to 15 atoms, approximately 9 atoms to 13 atoms, or approximately 11 atoms. Where the macrocycle-forming linker spans approximately 3 turns of the helix, the linkage contains approximately 13 atoms to 21 atoms, approximately 15 atoms to 19 atoms, or approximately 17 atoms. Where the macrocycle-forming linker spans approximately 4 turns of the helix, the linkage contains approximately 19 atoms to 27 atoms, approximately 21 atoms to 25 atoms, or approximately 23 atoms. Where the macrocycle-forming linker spans approximately 5 turns of the helix, the linkage contains approximately 25 atoms to 33 atoms, approximately 27 atoms to 31 atoms, or approximately 29 atoms. Where the macrocycle-forming linker spans approximately 1 turn of the helix, the resulting macrocycle forms a ring containing approximately 17 members to 25 members, approximately 19 members to 23 members, or approximately 21 members. Where the macrocycle-forming linker spans approximately 2 turns of the helix, the resulting macrocycle forms a ring containing approximately 29 members to 37 members, approximately 31 members to 35 members, or approximately 33 members. Where the macrocycle-forming linker spans approximately 3 turns of the helix, the resulting macrocycle forms a ring containing approximately 44 members to 52 members, approximately 46 members to 50 members, or approximately 48 members. Where the macrocycle-forming linker spans approximately 4 turns of the helix, the resulting macrocycle forms a ring containing approximately 59 members to 67 members, approximately 61 members to 65 members, or approximately 63 members. Where the macrocycle-forming linker spans approximately 5 turns of the helix, the resulting macrocycle forms a ring containing approximately 74 members to 82 members, approximately 76 members to 80 members, or approximately 78 members.

Peptides can contain one or more asymmetric centers and thus occur as racemates and racemic mixtures, single enantiomers, individual diastereomers and diastereomeric mixtures and geometric isomers (e.g., Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain aspects substantially free means that a composition contains at least about 90% by weight of a preferred enantiomer. In other aspects the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N Y, 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide, it can be desirable for the composition to be substantially homogeneous.

The addition of polyethelene glycol (PEG) moieties can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

XO—(CH$_2$CH$_2$O)$_n$—CH$_2$CH$_2$—Y where n is 2 to 10,000 and X is H or a terminal modification, e.g., a C$_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described, e.g., in WO 99/34833, WO 99/14259, and U.S. Pat. No. 6,348,558.

In certain aspects, macromolecular polymer (e.g., PEG) is attached to an agent described herein through an intermediate linker. In certain aspects, the linker is made up of from 1 to 20 amino acids linked by peptide bonds, wherein the amino acids are selected from the 20 naturally occurring amino acids. Some of these amino acids may be glycosylated, as is well understood by those in the art. In other aspects, the 1 to 20 amino acids are selected from glycine, alanine, proline, asparagine, glutamine, and lysine. In other aspects, a linker is made up of a majority of amino acids that are sterically unhindered, such as glycine and alanine. Non-peptide linkers are also possible. For example, alkyl linkers such as —NH(CH$_2$)$_n$C(O)—, wherein n=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, e.g., those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, e.g., Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C$_1$-C$_{20}$ straight or branched alkyl groups); fatty acid radicals; and combinations thereof.

α,α-Disubstituted non-natural amino acids containing olefinic side chains of varying length can be synthesized by known methods (see, e.g., Williams et al. J. Am. Chem. Soc., 113:9276, 1991; Schafmeister et al., J. Am. Chem Soc., 122:5891, 2000; and Bird et al., Methods Enzymol., 446: 369, 2008; Bird et al, Current Protocols in Chemical Biology, 2011). For peptides where an i linked to i+7 staple is used (two turns of the helix stabilized), either: a) one S$_5$ amino acid and one R$_8$ is used or b) one S$_8$ amino acid and one R$_5$ amino acid is used. R$_8$ is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_8$—OH and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (see, e.g., Williams et al., Org. Synth., 80:31, 2003).

The compounds of this invention may be modified by appending appropriate functionalities to enhance selective biological properties (including, e.g., hydrophobicity and/or the position/occurrence of hydrophobic patches). Such modifications are known in the art and include those which increase biological penetration into a given biological compartment (e.g., blood, lymphatic system, central nervous system), increase oral availability, increase solubility to allow administration by injection, alter metabolism, and alter rate of excretion.

A stabilized AMP selective for microbial versus mammalian membranes (i.e., a peptide able to kill or inhibit the growth of a microbe while also having a relatively low ability to lyse or inhibit the growth of a mammalian cell) may, e.g., possess a MIC for one or more microbes more than about 1.5-fold lower, more than about 2-fold lower, more than about 2.5-fold lower, more than about 3-fold lower, more than about 4-fold lower, more than about 5-fold lower, more than about 6-fold lower, more than about 7-fold lower, more than about 8-fold lower, more than about 9-fold lower, more than about 10-fold lower, more than about 15-fold lower, or more than about 20-fold lower than the MIC of the corresponding parent (i.e., unmodified) non-internally cross-linked peptide for the same one or more microbes. An antimicrobial peptide selective for microbial versus mammalian membranes can have a MIC of, e.g., about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 12 µg/ml, about 14 µg/ml, about 16 µg/ml, about 18 µg/ml, about 20 µg/ml, about 22 µg/ml, about 24 µg/ml, about 26 µg/ml, about 28 µg/ml, or about 30 µg/ml. An antimicrobial peptide selective for microbial versus mammalian membranes may lyse, e.g., less than about 50%, less than about 40%, less than about 30%, less than about 25%, less than about 20%, less than about 15%, less than about 10%, less than about 5%, less than about 2.5%, less than about 2%, or less than about 1% of red blood cells (RBCs) in a RBC hemolytic activity assay when administered at a concentration, e.g., greater than or approximately equal to 1-fold, 1.5-fold, 2-fold, 2.5-fold, 3-fold, 4-fold, 5-fold, 6-fold, 7-fold, 8-fold, 9-fold, or 10-fold its MIC for one or more microbes.

To avoid mammalian cell lytic properties and generate microbial-selective stabilized (e.g., stapled) AMPs, any of the stabilized (e.g., stapled) AMPs of this document can include an α-helical region that contains a first surface hydrophobic patch. In these stabilized AMPs the replacement of a relevant pair of amino acids by a linking group (e.g., $R_3$ in Formula (I)) results in discontinuity between the first surface hydrophobic patch and an additional one or more (e.g., 2, 3, 4, 5, 6, 8, or 10) surface hydrophobic patches in α-helical region. See, e.g., Example 11. Referring to Formula (I), such stabilized AMPs can be made, e.g., by determining the location of an established surface hydrophobic patch in an α-helical region of the stabilized AMP, and selecting integers w and y such that all amino acids $[Xaa]_x$ are located within the established surface hydrophobic patch. In an alternative method for generating microbial-selective structurally-stabilized AMPs, again referring to Formula (I), the location of two or more (e.g., 3, 4, 5, 6, 8, or 10) established surface hydrophobic patches in an α-helical region of the stabilized AMP is determined and integers w and y are selected such that amino acids $[Xaa]_x$ do not connect two or more (e.g., 3, 4, 5, 6, 8, or 10) established surface hydrophobic patches in the α-helical region of the stabilized AMP.

Another method of making the above-described selective and internally cross-linked (ICL) anti-microbial peptide (AMP) involves synthesizing the ICL AMP such that the ICL AMP includes an α-helical region comprising a first surface hydrophobic patch, and the replacement of a relevant pair of amino acids by a linking group (e.g., $R_3$ in Formula (I)) maintains or results in, relative to the corresponding parent non-internally crosslinked AMP, discontinuity between the first hydrophobic patch and one or more (e.g., 2, 3, 4, 5, 6, 8, or 10) additional surface hydrophobic patches on the ICL AMP.

The document also includes a method of designing an internally cross-linked (ICL) anti-microbial peptide (AMP) that includes: (a) creating one or more panels of ICL AMPs, each panel containing a plurality of panel member ICL AMPs in each of which: (a) the side chains of at least one pair of amino acids separated by 2, 3, or 6 amino acids are replaced by the linking group, $R_3$ (see Formula (I)), which connects the alpha carbons of the pair of amino acids; and (b) in each member of each panel, the pair of amino acids is at different positions as compared to the other members of the relevant panel; and (b) testing each member of all panels for (i) the presence of discontinuity between a first surface hydrophobic patch in an α-helical region of the relevant member and one or more additional surface hydrophobic patches on the α-helical region of the member; and (ii) the ability of each member of each panel for its ability to kill or inhibit the growth of a microbe (e.g., any of those disclosed herein such as a bacterium) and lyse or inhibit the growth of a mammalian cell. This method can further include manufacturing one or members of all the panels that have a relatively high ability to kill or inhibit the growth of a microbe (e.g., a bacterium) and a relatively low ability to lyse or inhibit the growth of a mammalian (e.g., human) cell. Methods of measuring the ability of chemical and biological agents to kill and/or inhibit the growth of microbial organisms and to lyse or inhibit the growth of human cells (e.g., red blood cells, leukocytes, or epithelial cells) are well known in the art (see, e.g., the Examples herein).

Hydrophobic patches within a peptide or protein may be identified using techniques generally known in the art, including, e.g., computational prediction/simulation (e.g., using ExPASy ProtScale, Scooby-domain prediction, PSIPRED, Kyte Doolittle plotting, and/or SPLIT,) and/or experimental determination (e.g., using techniques involving NMR spectroscopy, electron microscopy, homology modeling, small-angle X-ray and/or neutron scattering (SAXS/SANS), and/or X-ray crystallography) of the structure of the peptide or protein.

Pharmaceutically-acceptable salts of the compounds of this invention include those derived from pharmaceutically-acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

Methods suitable for obtaining (e.g., synthesizing), stapling, and purifying the peptides disclosed herein are also known in the art (see, e.g., Bird et. al., *Meth Enzymol.*, 446:369-386 (2008); Bird et al, *Curr Protoc Chem Biol.*, 2011; Walensky et al., *Science*, 305:1466-1470 (2004); Schafmeister et al., *J Am Chem Soc.*, 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein (see, e.g., Example 1).

In some aspects, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50%, or 60% DMSO. In a specific aspect, a 50%/50% DMSO/NMP solution is used. The solution may be incubated for a period of 1, 6, 12, or 24 hours, following which the resin may be washed, for example with dichloromethane or NMP. In one aspect, the resin is washed with NMP. Shaking and bubbling an inert gas into the solution may be performed.

Properties of the cross-linked polypeptides of the invention can be assayed, for example, using the methods described below.

Assays to Determine α-Helicity:

Compounds are dissolved in an aqueous solution (e.g. 5 mM potassium phosphate solution at pH 7, or distilled H$_2$O, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Cross-linked or the unmodified template peptides are dissolved in distilled H$_2$O or other buffer or solvent (e.g. at a final concentration of 50 μM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The compounds of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the compound and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the compound and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Compounds and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under N$_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays:

A key benefit of peptide stapling is the translation of in vitro protease resistance into markedly improved pharmacokinetics in vivo. Structurally-stabilized AMPs with potent and selective antimicrobial activity are screened for protease stability in vivo, e.g., using previously published methods (see, e.g., Bird et al., PNAS, 2010).

Pharmaceutical Compositions

One or more of the stabilized peptides disclosed herein (e.g., one or more of SEQ ID NOs: 1-17) can be formulated for use as or in pharmaceutical compositions. Such compositions can be formulated or adapted for administration to a subject via any route, e.g., any route approved by the Food and Drug Administration (FDA). Exemplary methods are described in the FDA Data Standards Manual (DSM).

The pharmaceutical compositions of this invention may be administered, e.g., orally, parenterally, by inhalation spray or nebulizer, topically, rectally, nasally, buccally, vaginally, via an implanted reservoir, by injection (e.g., intravenously, intra-arterially, subdermally, intraperitoneally, intramuscularly, and/or subcutaneously), in an ophthalmic preparation, or via transmucosal administration. Suitable dosages may range from about 0.001 to about 100 mg/kg of body weight, or according to the requirements of the particular drug. The pharmaceutical compositions of this invention may contain any conventional non-toxic pharmaceutically-acceptable carriers, adjuvants or vehicles. In some cases, the pH of the formulation may be adjusted with pharmaceutically-acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques. Alternatively or in addition, the present invention may be administered according to any of the methods as described in the FDA DSM.

As used herein, the compounds of this invention, including the compounds of formulae described herein, are defined to include pharmaceutically-acceptable derivatives or prodrugs thereof. A "pharmaceutically-acceptable derivative or prodrug" means any pharmaceutically-acceptable salt, ester, salt of an ester, or other derivative of a compound or agent disclosed herein which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

The methods herein contemplate administration of an effective amount of compound or compound composition to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Dosing can be determined using various techniques. The selected dosage level can depend upon a variety of factors, including, e.g., the activity of the particular compound employed, the route of administration, the time of administration, the rate of excretion or metabolism of the particular compound being employed, the duration of the treatment, other drugs, compounds, and/or materials used in combination with the particular compound employed, the age, sex, weight, condition, general health, and/or prior medical history of the patient being treated, and like factors well known in the medical arts. The dosage values can also vary with the severity of the condition to be alleviated. For any particular subject, specific dosage regimens can be adjusted over time according to the individual need and the professional judgment of the person administering or supervising the administration of the compositions.

In some aspects, a suitable daily dose of a compound of the disclosure can be that amount of the compound which is the lowest dose effective to produce a therapeutic effect. Such an effective dose will generally depend upon the factors described above. The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like.

A physician or veterinarian can prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some aspects, a dose can be expressed in terms of an amount of the drug divided by the mass of the subject, for example, milligrams of drug per kilograms of subject body mass. In some aspects, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Dosage can be based on the amount of the compound per kg body weight of the patient. Alternatively, the dosage of the subject disclosure can be determined by reference to the plasma concentrations of the compound. For example, the maximum plasma concentration ($C_{max}$) and the area under the plasma concentration-time curve from time 0 to infinity (AUC) can be used.

In some aspects, the subject is a human subject and the amount of the compound administered is 0.01-100 mg per kilogram body weight of the human subject. For example, in various examples, the amount of the compound administered is about 0.01-50 mg/kg, about 0.01-20 mg/kg, about 0.01-10 mg/kg, about 0.1-100 mg/kg, about 0.1-50 mg/kg, about 0.1-20 mg/kg, about 0.1-10 mg/kg, about 0.5-100 mg/kg, about 0.5-50 mg/kg, about 0.5-20 mg/kg, about 0.5-10 mg/kg, about 1-100 mg/kg, about 1-50 mg/kg, about 1-20 mg/kg, about 1-10 mg/kg body weight of the human subject. In one aspect, about 0.5 mg-10 mg of the compound per kilogram body weight of the human subject is administered. In some examples the amount of the compound administered is about 0.16 mg, about 0.32 mg, about 0.64 mg, about 1.28 mg, about 3.56 mg, about 7.12 mg, about 14.24 mg, or about 20 mg per kilogram body weight of the human subject. In some examples the amount of the compound administered is about 0.16 mg, about 0.32 mg, about 0.64 mg, about 1.28 mg, about 3.56 mg, about 7.12 mg, or about 14.24 mg per kilogram body weight of the human subject. In some examples the amount of the compound administered is about 0.16 mg per kilogram body weight of the human subject. In some examples the amount of the compound administered is about 0.32 mg per kilogram body weight of the human subject. In some examples the amount of the compound administered is about 0.64 mg per kilogram body weight of the human subject. In some examples the amount of the compound administered is about 1.28 mg per kilogram body weight of the human subject. In some examples the amount of the compound administered is about 3.56 mg per kilogram body weight of the human subject. In some examples the amount of the compound administered is about 7.12 mg per kilogram body weight of the human subject. In some examples the amount of the compound administered is about 14.24 mg per kilogram body weight of the human subject.

In some aspects about 0.5-about 20 mg or about 0.5-about 10 mg of the compound per kilogram body weight of the human subject is administered two times a week. For example about 0.5-about 1 mg, about 0.5-about 5 mg, about 0.5-about 10 mg, about 0.5-about 15 mg, about 1-about 5 mg, about 1-about 10 mg, about 1-about 15 mg, about 1-about 20 mg, about 5-about 10 mg, about 1-about 15 mg, about 5-about 20 mg, about 10-about 15 mg, about 10-about 20 mg, or about 15-about 20 mg of the compound per kilogram body weight of the human subject is administered about twice a week. In some examples, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, or about 20 mg of the compound per kilogram body weight of the human subject is administered two times a week. In some examples, the amount of the compound administered is about 1.25 mg, about 2.5 mg, about 5 mg, about 10 mg, or about 20 mg per kilogram body weight of the human subject and the compound is administered two times a week. In some examples, the amount of the compound administered is about 1.25 mg, about 2.5 mg, about 5 mg or about 10 mg per kilogram body weight of the human subject. The compound can be administered once a week, two times a week, three, four, five, six, or seven times a week. The compound can be administered once every 3 weeks.

In some aspects, the compound is administered gradually over a period of time. A desired amount of compound can, for example can be administered gradually over a period of from about 0.1 h-24 h. In some cases, a desired amount of compound is administered gradually over a period of 0.1 h, 0.5 h, 1 h, 1.5 h, 2 h, 2.5 h, 3 h, 3.5 h, 4 h, 4.5 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h. In some examples, a desired amount of compound is administered gradually over a period of 0.25-12 h, for example over a period of 0.25-1 h, 0.25-2 h, 0.25-3 h, 0.25-4 h, 0.25-6 h, 0.25-8 h, or 0.25-10 h. In some examples, a desired amount of compound is administered gradually over a period of 0.25-2 h. In some examples, a desired amount of compound is administered gradually over a period of 0.25-1 h. In some examples, a desired amount of compound is administered gradually over a period of 0.25 h, 0.3 h, 0.4 h, 0.5 h, 0.6 h, 0.7 h, 0.8 h, 0.9 h, 1.0 h, 1.1 h, 1.2 h, 1.3 h, 1.4 h, 1.5 h, 1.6 h, 1.7 h, 1.8 h, 1.9 h, or 2.0 h. In some examples, a desired amount of compound is administered gradually over a period of 1 h. In some examples, a desired amount of compound is administered gradually over a period of 2 h.

Administration of the compounds can continue as long as necessary. In some aspects, one or more compound of the disclosure is administered for more than 1 day, more than 1 week, more than 1 month, more than 2 months, more than 3 months, more than 4 months, more than 5 months, more than 6 months, more than 7 months, more than 8 months, more than 9 months, more than 10 months, more than 11 months, more than 12 months, more than 13 months, more than 14 months, more than 15 months, more than 16 months, more than 17 months, more than 18 months, more than 19 months, more than 20 months, more than 21 months, more than 22 months, more than 23 months, or more than 24 months. In some aspects, one or more compound of the disclosure is administered for less than 1 week, less than 1 month, less than 2 months, less than 3 months, less than 4 months, less than 5 months, less than 6 months, less than 7 months, less than 8 months, less than 9 months, less than 10 months, less than 11 months, less than 12 months, less than 13 months, less than 14 months, less than 15 months, less than 16 months, less than 17 months, less than 18 months, less than 19 months, less than 20 months, less than 21 months, less than 22 months, less than 23 months, or less than 24 months.

In some aspects, the compound is administered on day 1, 8, 15, and 28 of a 28 day cycle. In some aspects, the compound is administered on day 1, 8, 15, and 28 of a 28 day cycle and administration is continued for two cycles. In some aspects, the compound is administered on day 1, 8, 15, and 28 of a 28 day cycle and administration is continued for three cycles. In some aspects, the compound is administered on day 1, 8, 15, and 28 of a 28 day cycle and administration is continued for 4, 5, 6, 7, 8, 9, 10, or more cycles.

In some aspects, the compound is administered on day 1, 8, 11, and 21 of a 21-day cycle. In some aspects, the compound is administered on day 1, 8, 11, and 21 of a 21-day cycle and administration is continued for two cycles. In some aspects, the compound is administered on day 1, 8, 11, and 21 of a 21-day cycle and administration is continued for three cycles. In some aspects, the compound is administered on day 1, 8, 11, and 21 of a 21-day cycle and administration is continued for 4, 5, 6, 7, 8, 9, 10, or more cycles.

In some aspects, one or more compound of the disclosure is administered chronically on an ongoing basis. In some aspects administration of one or more compound of the disclosure is continued until documentation of disease progression, unacceptable toxicity, or patient or physician decision to discontinue administration.

Pharmaceutical compositions of this invention can include one or more peptides and any pharmaceutically-acceptable carrier and/or vehicle. In some instances, pharmaceuticals can further include one or more additional therapeutic agents in amounts effective for achieving a modulation of disease or disease symptoms. Such additional therapeutic agents may include antimicrobial agents (e.g., antibiotics) known in the art.

When co-administered, stapled AMPS of the invention operate in conjunction with antimicrobial agents to produce mechanistically additive or synergistic antimicrobial effects. For example, this can be due to structurally-stabilized AMPS piercing otherwise resistant bacterial membranes to allow for entry of alternative antibiotics and drug modalities. It is understood that the same additional therapeutic agents may be administered as a complex chemically bound (covalently or non-covalently) to an appropriate stapled peptide.

Examples of antibiotics suitable for co-administration with the stapled peptides disclosed herein include, but are not limited to, quinolones (e.g., levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, besifloxacin); β-lactams including cephalosporins (e.g., cefacetrile, cefixime, cefadroxil, cefaloglycin, cefalonium, cefaloridine, cefalotin, cefapirin, cefcapene, cefdaloxime, cefdinir, cefditoren, cefatrizine, cefetamet, cefazaflur, cefazedone, cefazolin, cefaradine, cefroxadine, ceftezole, cefteram, ceftibuten, ceftiofur, ceftiolene, ceftizoxime, cefaclor, cefprozil, cefuroxime, cefuzonam, cefmenoxime, cefodizime, cefotaxime, cefovecin, cefpimizole, cefpirome, cefquinome, ceftobiprole, cefpodoxime, ceftazidime, ceftaroline, cefclidine, cefepime, cefluprenam, cefoselis, cefozopran, cephalexin, cephaloridine, cefamandole, cefsulodin, cefonicid, cefoperazine, cefoperazone, cefprozil, ceftriaxone), penicillins and penicillin derivatives (e.g., penicillin G, penicillin V, procaine penicillin, benzathine penicillin, benzathine benzylpenicillin, ampicillin, epicillin, amoxicillin, benzylpenicillin, clometocillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, azidocillin, cloxacillin, nafcillin, pivampicillin, penamecillin, mecillinam, propicillin, pheneticillin, ticarcillin temocillin), carbapenems (e.g., thienamycin, tomopenem, lenapenem, tebipenem, razupenem, imipenem, meropenem, ertapenem, doripenem, panipenem (betamipron), biapenem), carbacephems (e.g., loracarbef), penems (e.g., faropenem), cephamycins (e.g., cefbuperazone, cefmetazole, cefminox, cefotetan, cefoxitin), monobactams (e.g., aztreonam, nocardicin A, tabtoxin, tigemonam), and oxacephems (e.g., flomoxef, latamoxef); lipopeptide antibiotics (e.g., amphomycin, aspartocin, brevistin, cerexin A, cerexin B, glumamycin, laspartomycin, tsushimycin, zaomycin, daptomycin); polymyxin antibiotics (e.g., polymyxin B, colistin (polymyxin E), polymyxin M); aminoglycosides (e.g., gentamicin, amikacin, tobramycin, debekacin, kanamycin, neomycin, netilmicin, paromomycin, sisomycin, spectinomycin, streptomycin); glycopeptides (e.g., vancomycin, teicoplanin, telavancin, ramoplanin, daptomycin, decaplanin, bleomycin); macrolides (e.g., azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin, cineromycin B); ansamycins (e.g., streptovaricin, geldanamycin, herbimycin, rifamycin, rifampin, rifabutin, rifapentine, rifamixin); linezolid; pristinamycin; and sulfonamides (e.g., sulfanilamide, sulfacetamide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole, phthalylsulfathiazole).

When the compositions of this invention comprise a combination of a compound of the formulae described herein and one or more additional therapeutic or prophylactic agents, both the compound and the additional agent should be present at dosage levels of between about 1% to about 100%, or between about 5% to about 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The term "pharmaceutically-acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically-acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin can also be advantageously used to enhance delivery of compounds of the formulae described herein.

The pharmaceutical compositions of this invention may contain any conventional non-toxic pharmaceutically-acceptable carriers, adjuvants, or vehicles. In some cases, the pH of the formulation may be adjusted with pharmaceutically-acceptable acids, bases, or buffers to enhance the stability of the formulated compound or its delivery form. The term parenteral as used herein includes parenteral, epidural, subcutaneous, intra-cutaneous, intra-venous, intra-muscular, intra-articular, intra-arterial, intra-synovial, intra-sternal, intra-thecal, intra-lesional and intra-cranial injection or infusion techniques.

An effective amount of a compound of the disclosure can be administered in either single or multiple doses by any of the accepted modes of administration. Regardless of the route of administration selected, the compounds of the present disclosure, and/or the pharmaceutical compositions of the present disclosure, are formulated into pharmaceutically-acceptable dosage forms. The compounds according to the disclosure can be formulated for administration in any convenient way for use in human or veterinary medicine, by analogy with other pharmaceuticals.

In one aspect, the disclosure provides pharmaceutical formulation comprising a therapeutically-effective amount of one or more of the compounds described above, formulated together with one or more pharmaceutically acceptable carriers (additives) and/or diluents. In one aspect, one or more of the compounds described herein are formulated for parenteral administration for parenteral administration, one or more compounds disclosed herein can be formulated as aqueous or non-aqueous solutions, dispersions, suspensions, or emulsions or sterile powders which can be reconstituted into sterile injectable solutions or dispersions just prior to use. Such formulations can comprise sugars, alcohols, antioxidants, buffers, bacteriostats, solutes which render the formulation isotonic with the blood of the intended recipient or suspending or thickening agents. These compositions can also contain adjuvants such as preservatives, wetting agents, emulsifying agents and dispersing agents. Prevention of the action of microorganisms upon the subject compounds can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin. If desired, the formulation can be diluted prior to use with, e.g., an isotonic saline solution or a dextrose solution. In some examples, the compound is formulated as an aqueous solution and is administered intravenously.

Pharmaceutical compositions can be in the form of a solution or powder for injection. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically-acceptable dosage forms such as emulsions and or suspensions. Other commonly used surfactants such as Tweens or Spans and/or other similar emulsifying agents or bioavailability enhancers which are commonly used in the manufacture of pharmaceutically-acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain aspects, the association is covalent. In other aspects, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of infection. The terms "treat", "treating", or "treatment" as used herein, refers to partially or completely alleviating, inhibiting, ameliorating, and/or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., infection) refers to any lessening, whether permanent or temporary, lasting or transient that can be attributed to or associated with treatment by the compositions and methods of the present invention. In some aspects, treatment can promote or result in, for example, a decrease in the number of microbial cells or organisms (e.g., in a subject) relative to the number of microbial cells or organisms prior to treatment; a decrease in the viability (e.g., the average/mean viability) of microbial cells or organisms (e.g., in a subject) relative to the viability (e.g., the average/mean viability) of microbial cells or organisms (e.g., in the subject) prior to treatment; and/or reductions in one or more symptoms associated with one or more infections in a subject relative to the subject's symptoms prior to treatment.

Examples of bacteria internally cross-linked AMPs are active against include, without limitation, Staphylococci (e.g., *S. aureus, S. intermedius, S. epidermidis*, and other coagulase negative Staphylococci), Neisseriae (e.g., *N. gonorrheae* and *N. meningitidis*), Streptococci (e.g., Group A *Streptococcus* (e.g., *S. pyogenes*), Group B *Streptococcus* (e.g., *S. agalactiae*), Group C *Streptococcus*, Group G *Streptococcus*, *S. pneumoniae*, and *viridans* Streptococci), *Chlamydia trachomatis*, Treponemae (e.g., *T. pallidum*, T pertenue, and T cerateum), *Haemophilus* bacteria (e.g., *H. ducreyi, H. influenzae*, and *H. aegyptius*), Bordetellae (e.g., *B. pertussis, B. parapertussis*, and *B. bronchiseptica*), *Gardnerella vaginalis*, *Bacillus* (e.g., *B. anthracis* and *B. cereus*), Mycobacteria (e.g., *M. tuberculosis* and *M. leprae*), *Listeria monocytogenes*, *Borrelia burgdorferi*, *Actinobacillus pleuropneumonias*, *Helicobacter pylori*, *Clostridium* (e.g. *C. perfringens, C. septicum, C. novyi*, and *C. tetani*), *Escherichia coli, Porphyromonas gingivalis, Vibrio cholerae, Salmonella* bacteria (e.g., *S. enteriditis, S. typhimurium*, and *S. typhi*), *Shigella* bacteria, *Francisella* bacteria, *Yersinia* bacteria (e.g. *Y. pestis* and *Y. enterocolitica*), *Burkholderia* bacteria, *Pseudomonas* bacteria, and *Brucella* bacteria. Mycoplasmal organisms AMPs are active against include, e.g., *M. pneumoniae, M. fermentans, M. hominis*, and *M. penetrans*.

Examples of fungal (including yeast) organisms internally cross-linked AMPs are active against include, but are not limited to, *Candida albicans*, other *Candida* species, *Cryptococcus neoformans, Histoplasma capsulatum*, and *Pneumocystis carinii*.

Examples of protozoan parasites internally cross-linked AMPs are active against include, without limitation, *Trichomonas vaginalis, Plasmodium falciparum, P. vivax, P. ovale, P. malariae, Entamoeba histolytica, Toxoplasma brucei, Toxoplasma gondii*, and *Leishmania major*.

Examples of viruses internally cross-linked AMPS may be employed against include, but are not limited to, human immunodeficiency virus (HIV) 1 and 2, human lymphotropic virus (HTLV), measles virus, rabies virus, hepatitis virus A, B, and C, rotaviruses, rhinoviruses, influenza virus, parainfluenza virus, respiratory syncytial virus, adenoviruses, parvoviruses (e.g., parvovirus B 19), roseola virus, enteroviruses, papilloma viruses, retroviruses, herpesviruses (e.g., herpes simplex virus, varicella zoster virus, Epstein Barr virus (EBV), human cytomegalovirus (CMV), human herpesvirus 6, 7 and 8), poxviruses (e.g., *variola major* and *variola minor*, vaccinia, and monkeypox virus), feline leukemia virus, feline immunodeficiency virus, and simian immunodeficiency virus.

Disorders that can be treated by the compositions, formulations, and/or methods described herein include, but are not limited to, infectious diseases. Infectious diseases can be caused by pathogens, such as bacteria, viruses, fungi or parasites. In some aspects, an infectious disease can be passed from person to person. In some aspects, an infectious disease can be transmitted by bites from insects or animals. In some aspects, an infectious disease can be acquired by ingesting contaminated food or water or being exposed to organisms in the environment. Some infectious diseases can be prevented by vaccines.

In specific aspects, infectious diseases that can be treated by the compositions, formulations, and/or methods described herein include, but are not limited to, *Acinetobacter* infections, Actinomycosis, African sleeping sickness (African trypanosomiasis), AIDS (Acquired immunodeficiency syndrome), Amebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Bartonellosis, *Baylisascaris* infection, BK virus infection, Black *piedra*, Blastocystosis, Blastomycosis, Bolivian hemorrhagic fever, Botulism (and Infant botulism), Brazilian hemorrhagic fever, Brucellosis, Bubonic plague, *Burkholderia* infection, Buruli ulcer, Caicivirus infection (Norovirus and Sapovirus), Campylobacteriosis, Candidiasis (Moniliasis; Thrush), Capillariasis, Carrion's disease, Cat-scratch disease, Cellulitis, Chagas Disease (American trypanosomiasis), Chancroid, Chickenpox, Chikungunya, *Chlamydia*, *Chlamydophila pneumoniae* infection (Taiwan acute respiratory agent or TWAR), Cholera, Chromoblastomycosis, Chytridiomycosis, Clonorchiasis, *Clostridium difficile* colitis, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, *Desmodesmus* infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolasis, Fasciolopsiasis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann-Stráussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot, and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma (disambiguation), Myiasis, Neonatal conjunctivitis (Ophthalmia neonatorum), Variant Creutzfeldt-Jakob disease (vCJD, nvCJD), Nocardiosis, Onchocerciasis (River blindness), Opisthorchiasis, Paracoccidioidomycosis (South American blastomycosis), Paragonimiasis, Pasteurellosis, *Pediculosis capitis* (Head lice), *Pediculosis corporis* (Body lice), *Pediculosis pubis* (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Relapsing fever, Respiratory syncytial virus infection, Rhinosporidiosis, Rhinovirus infection, *Rickettsial* infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (*Variola*), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea* nigra, *Tinea* pedis (Athlete's foot), *Tinea* unguium (Onychomycosis), *Tinea versicolor* (*Pityriasis versicolor*), Toxocariasis (Ocular Larva Migrans (OLM)), Toxocariasis (Visceral Larva Migrans (VLM)), Trachoma, Toxoplasmosis, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile Fever, White *piedra* (*Tinea* blanca), *Yersinia pseudotuberculosis* infection, Yersiniosis, Yellow fever, and Zygomycosis.

The compositions, formulations, and/or methods described herein can be used to treat a pathogen. In some aspects, the pathogen can be a virus, bacterium, prion, a fungus, or a parasite. In specific aspects, the pathogen described herein include, but are not limited to, *Acinetobacter baumannii*, *Actinomyces israelii*, *Actinomyces gerencseriae* and *Propionibacterium propionicus*, *Trypanosoma brucei*, HIV (Human immunodeficiency virus), *Entamoeba histolytica*, *Anaplasma* species, *Angiostrongylus*, *Anisakis*, *Bacillus anthracis*, *Arcanobacterium haemolyticum*, Junin virus, *Ascaris lumbricoides*, *Aspergillus* species, Astroviridae family, *Babesia* species, *Bacillus cereus*, bacterial vaginosis microbiota, *Bacteroides* species, *Balantidium coli*, *Bartonella*, *Baylisascaris* species, BK virus, Piedraia hortae, *Blastocystis* species, *Blastomyces dermatitidis*, *Machupo virus*, *Clostridium botulinum*, Sabia, *Brucella* species, Enterobacteriaceae, *Burkholderia cepacia* and other *Burkholderia* species, *Mycobacterium ulcerans*, Caliciviridae family, *Campylobacter* species, *Candida albicans* and other *Candida* species, *Capillaria philippinensis*, *Capillaria* hepatica, *Capillaria aerophila*, *Bartonella bacilliformis*, *Bartonella henselae*, Group A *Streptococcus* and *Staphylococcus*, *Trypanosoma cruzi*, *Haemophilus ducreyi*, Varicella zoster virus (VZV), Alphavirus, *Chlamydia trachomatis*, *Chlamydophila pneumoniae*, *Vibrio cholera*, *Fonsecaea pedrosoi*, *Batrachochytrium dendrabatidis*, *Clonorchis sinensis*, *Clostridium difficile*, *Coccidioides immitis* and *Coccidioides posadasii*, Colorado tick fever virus (CTFV), rhinoviruses and coronaviruses, PRNP, Crimean-Congo hemorrhagic fever virus, *Cryptococcus neoformans*, *Cryptosporidium* species, *Ancylostoma braziliense*; multiple other parasites, *Cyclospora cayetanensis*, *Taenia solium*, Cytomegalovirus, Dengue viruses (DEN-1, DEN-2, DEN-3 and DEN-4)—Flaviviruses, Green algae *Desmodesmus armatus*, *Dientamoeba fragilis*, *Corynebacterium diphtheria*, *Diphyllobothrium*, *Dracunculus medinensis*, Ebolavirus (EBOV), *Echinococcus* species, *Ehrlichia* species, *Enterobius vermicularis*, *Enterococcus* species, *Enterovirus* species, *Rickettsia prowazekii*, Parvovirus B 19, Human herpesvirus 6 (HHV-6) and Human herpesvirus 7 (HHV-7), *Fasciola hepatica* and *Fasciola gigantica*, *Fasciolopsis buski*, PRNP, Filarioidea superfamily, *Clostridium perfringens*, *Fusobacterium* species, *Clostridium perfringens*, other *Clostridium* species, *Geotrichum candidum*, *Giardia lamblia*, *Burkholderia mallei*, *Gnathostoma spinigerum* and *Gnathostoma hispidum*, *Neisseria gonorrhoeae*, *Klebsiella granulomatis*, *Streptococcus pyogenes*, *Streptococcus agalactiae*, *Haemophilus* influenza, Enteroviruses, mainly Coxsackie A virus and Enterovirus 71 (EV71), Sin Nombre virus, Heartland virus, *Helicobacter pylori*, *Escherichia coli* O157:H7, O111 and O104:H4, Bunyaviridae family, Hepatitis A virus, Hepatitis B virus, Hepatitis C virus, Hepatitis D Virus, Hepatitis E virus, Herpes simplex virus 1 and 2 (HSV-1 and HSV-2), *Histoplasma capsulatum*, *Ancylostoma duodenale* and *Necator americanus*, Human bocavirus (HBoV), *Ehrlichia ewingii*, *Anaplasma phagocytophilum*, Human metapneumovirus (hMPV), *Ehrlichia chaffeensis*, Human papillomavirus (HPV), Human parainfluenza viruses (HPIV), *Hymenolepis nana* and *Hymenolepis diminuta*, Epstein-Barr Virus (EBV), Orthomyxoviridae family, *Isospora belli*, *Kingella kingae*, Lassa virus, *Legionella pneumophila*, *Leishmania* species, *Mycobacterium leprae*, *Mycobacterium lepromatosis*, *Leptospira* species, *Listeria monocytogenes*, *Borrelia burgdorferi*, *Borrelia garinii*, *Borrelia afzelii*, *Wuchereria bancrofti*, *Brugia malayi*, Lymphocytic choriomeningitis virus (LCMV), *Plasmodium* species, Marburg virus, Measles virus, Middle East respiratory syndrome coronavirus, *Burkholderia pseudomallei*, *Neisseria meningitides*, *Metagonimus yokagawai*, *Microsporidia* phylum, Molluscum contagiosum virus (MCV), Monkeypox virus, Mumps virus, *Rickettsia typhi*,

*Mycoplasma pneumoniae,* Actinomycetoma, Eumycetoma, parasitic dipterous fly larvae, *Chlamydia trachomatis, Neisseria gonorrhoeae, Nocardia asteroides, Nocardia* species, *Onchocerca volvulus, Opisthorchis viverrini* and *Opisthorchis felineus, Paracoccidioides brasiliensis, Pediculus humanus capitis,* Phthirus pubis, *Bordetella pertussis, Yersinia pestis, Streptococcus pneumoniae, Pneumocystis jirovecii,* Poliovirus, *Prevotella* species, *Naegleria fowleri,* JC virus, *Chlamydophila psittaci, Coxiella burnetii,* Rabies virus, *Borrelia hermsii, Borrelia recurrentis, Borrelia* species, Respiratory syncytial virus (RSV), *Rhinosporidium seeberi,* Rhinovirus, *Rickettsia* species, *Rickettsia akari,* Rift Valley fever virus, *Rickettsia rickettsia,* Rotavirus, Rubella virus, *Salmonella* species, SARS coronavirus, *Sarcoptes scabiei, Schistosoma* species, *Shigella* species, Varicella zoster virus (VZV), *Variola major, Variola minor, Sporothrix schenckii, Staphylococcus* species, *Strongyloides stercoralis,* Measles virus, *Treponema pallidum, Taenia* species, *Clostridium tetani, Trichophyton* species, *Trichophyton tonsurans, Epidermophyton floccosum, Trichophyton rubrum, Trichophyton mentagrophytes, Trichophyton rubrum, Hortaea werneckii, Trichophyton* species, *Malassezia* species, *Toxocara canis, Toxocara cati, Chlamydia trachomatis, Toxoplasma gondii, Trichinella spiralis, Trichomonas vaginalis, Trichuris trichiura, Mycobacterium tuberculosis, Francisella tularensis, Salmonella enterica* subsp. *enterica,* serovar typhi, *Rickettsia, Ureaplasma urealyticum, Coccidioides immitis, Coccidioides posadasii,* Venezuelan equine encephalitis virus, Guanarito virus, *Vibrio vulnificus, Vibrio parahaemolyticus,* multiple viruses, West Nile virus, *Trichosporon beigelii, Yersinia pseudotuberculosis, Yersinia enterocolitica,* Yellow fever virus, Mucorales order (Mucormycosis), and Entomophthorales order (Entomophthoramycosis).

All the methods of treatment and prophylaxis described herein may be applied to at least any or all the above-listed microbial organisms.

In some aspects, the compounds of the invention can be toxic to one microbe. In some aspects, the compounds of the invention can be toxic to two microbes. In some aspects, the compounds of the invention can be toxic to three microbes. In some aspects, the compounds of the invention can be toxic to four microbes. In some aspects, the compounds of the invention can be toxic to five microbes.

In some aspects, the compounds of the invention can be used to treat a microbe without damaging the host subject. In some aspects, the compounds of the invention can be used to treat two microbes without damaging the host subject. In some aspects, the compounds of the invention can be used to treat three microbes without damaging the host subject. In some aspects, the compounds of the invention can be used to treat four microbes without damaging the host subject. In some aspects, the compounds of the invention can be used to treat five microbes without damaging the host subject.

In general, methods include selecting a subject and administering to the subject an effective amount of one or more of the peptides herein, e.g., in or as a pharmaceutical composition, and optionally repeating administration as required for the prophylaxis or treatment of a microbial infection and can be administered, e.g., orally, intravenously or topically.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the therapeutic compounds described herein can include a single treatment or a series of treatments. For example, effective amounts can be administered at least once. Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the peptides herein can further be co-administered with one or more additional therapeutic agents in amounts effective for achieving a modulation of disease or disease symptoms. Such additional therapeutic agents may include conventional antimicrobial agents (e.g., antibiotics) known in the art. When co-administered, stapled AMPs of the invention operate in conjunction with conventional antimicrobial agents to produce mechanistically additive or synergistic antimicrobial effects. Without being limited by any particular mechanism of action, certain internally cross-linked (e.g., stapled) AMPs having the ability to produce "pores" in the membranes of certain microbial organisms (including, e.g., Gram-negative bacteria) can act to facilitate and/or enhance the passage of appropriate conventional antimicrobial agents to the interiors of relevant microbial cells. For the same purpose, the internally cross-linked AMPs can be conjugated (covalently or non-covalently) to appropriate antimicrobial agents, the resulting conjugates being administered to appropriate subjects.

The ability of internally cross-linked AMPs to produce "pores" in the membranes of microbial organisms provides the basis for another utility for them. Thus, e.g., relevant microbial organisms (e.g., any of those disclosed herein) can be contacted either in a subject or in vitro to a internally cross-linked AMP with the ability to produce "pores" or even lysis of the microbial organism. As result of this activity, nucleic acids (e.g., DNA and/or RNA) are released from microbial organisms into their surroundings. This phenomenon can be used as a basis for accurate, rapid, and inexpensive identification of the microbial organism. Where the contacting occurs in a subject, any of a variety of bodily fluids (e.g., blood, lymph, urine, feces, mucus, or tears) or body lavages can be tested. Where the contacting occurs in vitro, culture medium can be tested.

Application to Medical or Hygienic Devices

The antimicrobial peptides of the invention can be applied to, or incorporated into, various medical and/or hygienic devices (e.g., as a coating, or impregnated within a biodegradable device for exposure or release as the device degrades or dissolves after the device is inserted into a bodily canal of a vertebrate subject, inserted into a bodily cavity of a vertebrate subject, or applied to a tissue or organ of a vertebrate animal) to prevent or inhibit microbial (e.g., bacterial or biofilm) growth. Medical or hygienic devices suitable for use with the stapled peptides disclosed herein include, but are not limited to, devices that are inserted into a bodily canal of a vertebrate subject, inserted into a bodily cavity of a vertebrate subject, or applied to a tissue or organ of a vertebrate animal for the purpose of: (a) wound protection; (b) preventing or reducing unwanted, or overcoming restricted, release from the body of the vertebrate subject of a bodily fluid, bodily secretion, or excreta (e.g., blood, menses, urine, lymphatic fluid, cerebrospinal fluid, semen, saliva, vaginal secretions, mucus, or feces); (c) delivering a drug or some other therapeutic or prophylactic agent to a subject; (d) replacing absent or supplementing defective organ functions; or (e) maintaining the patency of a bodily canal (e.g., a blood vessel). Specific examples of medical or hygienic devices include, without limitation: peripheral IVs, central lines, portacaths, dialysis catheters; rectal devices such as suppositories, enemas, and catheters; nasal, tracheal, or esophageal delivery devices; vaginal devices such as vaginal tampons and contraceptive devices (e.g., diaphragms or intrauterine devices (IUDs)); venous, arterial, intracranial and other needles, catheters and stents; renal dialysis accesses; surgical bandages, sutures, or dressings; ostomy devices; natural and synthetic implantable tissue matrices (see, e.g., U.S. Pat. No. 5,885,829, incorporated herein by reference in its entirety); pace makers and pace maker wires and leads; synthetic and natural prostheses such as hip and knee and joint prostheses and heart valves; osmotic pumps (e.g., mini osmotic pumps) that are implanted in body cavity (e.g., the peritoneal cavity) and provide slow delivery of a drug or some other therapeutic or prophylactic agent.

Treatment of Biofilms and Biofilm-Associated Infections

Stapled AMPS of the invention can be used to treat or sterilize bacterial biofilms in vivo or in vitro. For example, effective amounts can be administered to the lung for treating cystic fibrosis or (topically) to the vagina for treating bacterial vaginosis (BV). BV is a syndrome in which the vaginal flora becomes altered such that *Lactobacillus* species no longer dominate [Forsum et al. (2005) APMIS 113:81-90]. BV is characterized by overgrowth of organisms such as *Gardnerella vaginalis*, some anaerobes, and *Mycoplasma hominis*. Vaginal organisms such as Atopobium species may be associated with BV [Verstraelen et al. (2004) Am J. Obstet. and Gynecol. 191:1130-1132]. The anaerobes associated with BV include *Bacteroides, Prevotella, Peptostreptococcus*, and *Morbiluncus* species [Forsum et al. (2005), supra]. In studies of pregnant women, both asymptomatic and symptomatic BV patients were found to have a 10-fold or higher increase in these organisms, particularly *Gardnerella*. Symptomatic women have 100- to 1000-fold increases in *Gardnerella* bacteria and anaerobes. In such patients there is a concomitant drop in lactobacilli, and for unknown reasons, the lactobacilli that are present make less hydrogen peroxide that their normal counterparts. The amine product trimethylamine is a metabolic product of bacterial overgrowth and its fishy odor is indicative of BV. Factors that have been associated with BV include sexual activity, particularly new sexual partners, antibiotic use, reduction for unknown reasons of pH, and use of IUDs (intrauterine devices) [Hawes et al. (1996) J. Infect. Dis. 190:1374-1381]. Approximately one half of BV patients are asymptomatic. Persistent vaginal inflammation is associated with BV.

The clinical diagnosis of BV is based on having three of the four of the following characteristics in vaginal discharges: (1) pH above 4.5; (2) a thin skim milk appearance; (3) a fishy amine odor when 10% potassium hydroxide is placed on the discharge; and (4) clue cells [Amsel et al. (1983) Am. J. Med. 74:14-22]. Clue cells are vaginal cells that are so covered with bacteria that their borders are obscured. On microscopic examination of vaginal discharges from patients with BV, long lactobacilli morphotypes are seen to be diminished.

Pregnant women with BV have 50% to 100% increases in preterm, low birth-weight deliveries, amniotic fluid infections, and chorioamnion infections [Hillier et al. (1995) N. Engl. J. Med. 333:1737-1742]. The high concentration of potentially virulent microbes also predisposes the upper genital tract to infections, including postpartum endometritis after cesarean delivery, pelvic inflammatory disease following therapeutic abortion, and vaginal cuff cellulitis following abdominal hysterectomy.

Treatment options for BV include metronidazole (orally) and clindamycin (topically) in non-pregnant women and metronidazole in symptomatic pregnant women as first line treatment regimens. For recurrent BV, regular treatment and then biweekly suppressive doses of metronidazole are recommended. *Lactobacillus* given orally or intravaginally may help, though its effectiveness is still in debate.

Further Applications

Stapled peptides as disclosed herein can also be used to prevent or reduce a likelihood of viral (e.g., HIV) infection. For example, stapled AMPS can be administered intravaginally (e.g., topically) to eliminate distinct vaginal bacterial flora that pose an inflammatory risk shown to increase the risk of viral (e.g., HIV-1 or HIV-2) transmission and/or infection.

The peptides herein can be applied in the food or beverage processing context (e.g., to food and beverage (e.g., beer) products in sterilization and/or fermentation processes) to reduce or eliminate the risk of microbial (e.g., bacterial) contamination. Currently, the naturally occurring antibacterial peptide nisin is used in food processing to eradicate pathogenic Gram-positive bacteria. However, no effective antimicrobial agent is available to eradicate Gram-negative bacteria in the food processing context. Unlike nisin, the synthetic peptides of the invention display broad-spectrum activity against both Gram-positive and Gram-negative bacteria.

Stapled AMPS of the invention can also be applied in veterinary and/or agricultural applications to prevent and/or treat microbial infection in, e.g., an animal or a plant suffering from an infection or at risk of infection. Examples of suitable animals for treatment are generally known in the art and include (but are not limited to), e.g., poultry and other birds (including chickens, turkeys, ducks, ostrich, emu, quail), ruminants (including goats, sheep, and cattle), fish, pigs, rabbits, mice, rats, horses, donkeys, monkeys, apes, felines (including cats), hamsters, ferrets, guinea pigs, and canines (including dogs). Examples of suitable plants for treatment are generally known in the art and include (but are not limited to), e.g., almond, apple, amaranth, artichoke, asparagus, avocado, banana and plantain, barley, beet, berries (including blueberry, blackberry, strawberry, and raspberry), breadfruit and jackfruit, brussels sprout, cabbage, carrot, cassava, cauliflower and broccoli, celery, chayote, cherry, coconut, collard and kale, corn (maize), cucumber and zucchini, dandelion, eggplant, endive and chicory, garlic, kohlrabi, grape, legume, lettuce, melons (including honeydew, cantaloupe, and watermelon), mustard, oat, oca, olive, okra, onion, orange and grapefruit, oyster plant, pear, peach, pemmican, pepper, potato and other tubers, *quinoa*, radish, rice, rhubarb, rye, sago, sorghum, soybean, spinach, pumpkin and other squashes, sunchoke, taro, teff, tomato, turnip, ulluco, vanilla, watercress, wheat, yam, and yautia. Examples of suitable foods for treatment are generally known in the art and include (but are not limited to), e.g., algae, mushrooms, and products derived from animals (e.g., beef, butter, eggs, (ice) cream, gravy, milk, pork, veal, yogurt) and/or plants (e.g., beer, bread, cereal, chocolate, coffee, ketchup, mustard sauce, oatmeal, juice, monosodium glutamate, salad, soda, soft drinks, soymilk, soy sauce, tea, tofu, fries, vinegar, wine) as described above.

The peptides herein can also be applied in the personal care and/or consumer products context (e.g., to health or beauty products in sterilization processes) to reduce or eliminate the risk of microbial (e.g., bacterial) contamination. Examples of suitable products for treatment are generally known in the art and include (but are not limited to), e.g., brushes, conditioners, clips, clippers, curling irons, shampoos, soaps, lotions, topical acne ointments, oils, colorants, dyes, perfumes, pins, fragrances, razors, shaving devices, deodorants, cosmetics, kitchen and/or dining devices (e.g., cutting boards, racks, containers, pots, pans, utensils), and cleaning products (e.g., brooms, mops, dustpans, sweepers) and cleaning solutions.

EXAMPLES

Example 1: Synthesis of Stapled Magainin II Analogues

Magainin II is a well characterized AMP that was used as scaffold for the design of compounds. A panel of stapled magainin II peptides was generated (FIG. 3A). For the initial panel, seven different locations using an i, i+7 staple that spans two α-helical turns were sampled. The staple locations on the hydrophobic and hydrophilic face of the peptide and on the two interfaces were tested (FIG. 3B). Three mutations (SBA, G13A, G18A) were introduced since alanine can promote helicity within a peptide sequence.

Example 2: Helical Characterization of Stapled Magainin II Analogues

Figure 4A:
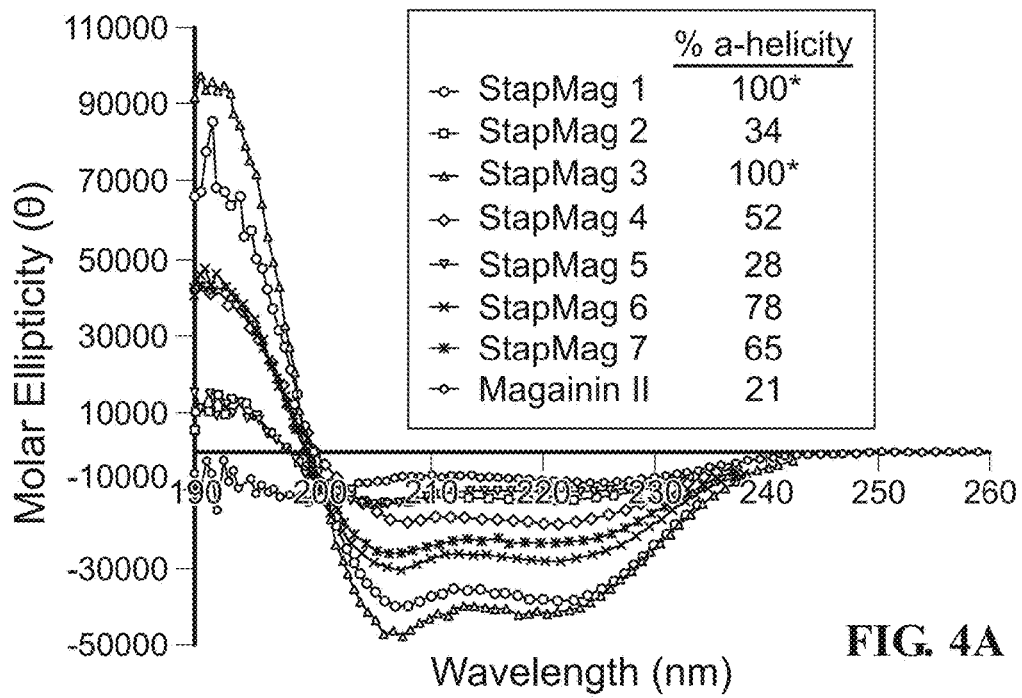
FIG. 4A is a series of line graphs depicting the CD spectra of magainin II and stapled analogues in aqueous solution.
Figure 4B:
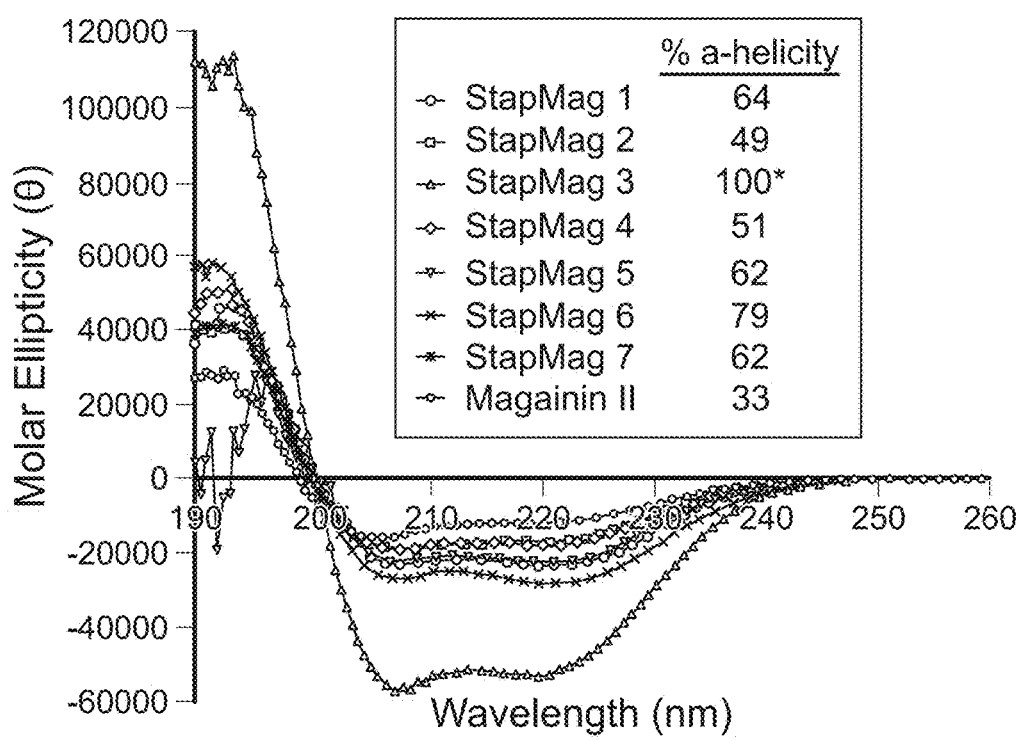
FIG. 4B is a series of line graphs depicting the CD spectra of magainin II and stapled analogues in TFE:Water (1:1) mixture. An * indicates that the measured α-helicity exceeds the calculated ideal α-helicity of an undecapeptide standard.

To determine the helicity of the panel of stapled magainin II analogues, the peptides were dissolved in water using CD spectroscopy in the presence and absence of trifluoroethanol (TFE; 50% v/v), a helix-promoting solvent. In the absence of TFE, the stapled analogues displayed much higher levels of helicity compared to unstapled magainin II, which was partially disordered (FIG. 4A). Levels of helicity ranged from approximately 34% for MagStap 2 to 100% for MagStap 1 and 3, as compared to an idealized α-helical peptide. These results suggest that the location of the hydrocarbon staple has significant impact on inducing α-helical structure. When the helicity in the presence of TFE was measured, most of the stapled analogues were 50-60% helical except for MagStap 3, which retained 100% α-helical content. In contrast, the induced α-helicity for magainin II did not exceed 32%, even in the presence of TFE (FIG. 4B).

Example 3: Antimicrobial Activity of Stapled Magainin II Peptides

The panel of stapled magainin II peptides was tested on two Gram-negative bacterial strains, *E. coli* and *S. marcescens* and two Gram-positive strains, *B. cereus* and *E. durans*. The results of this analysis are present in Table 3.

TABLE 3

Minimum inhibitory concentrations (MICs) of magainin II and stapled derivatives against Gram-negative and Gram-positive bacterial strains

| Peptide | Antimicrobial Activity MIC (µg/ml) | | | |
|---|---|---|---|---|
| | *E. coli* | *S. marcescens* | *B. cereus* | *E. durans* |
| Magainin II | 50 | >50 | >50 | >50 |
| MagStap 1 | 12.5 | >50 | 12.5 | 25 |
| MagStap 2 | 3.1 | >50 | 3.1 | 12.5 |
| Magstap 3 | 3.1 | >50 | 6.2 | 25 |
| MagStap 4 | 12.5 | >50 | 6.2 | 25 |
| MagStap 5 | 12.5 | >50 | 12.5 | 25 |
| MagStap 6 | 3.1 | >50 | 3.1 | 12.5 |
| MagStap 7 | 6.2 | >50 | 6.2 | 25 |

The peptides in Table 3 are SEQ ID NOs: 134 and 178-184, numbered consecutively from top to bottom.

The minimum inhibitory concentration (MIC) of the stapled peptides in *E. coli* was more than 3-fold lower than the MIC of magainin II; with select compounds, like MagStap 2 and 6, exhibiting greater than a 15-fold increase in potency. Even though the MICs for all the peptides tested in *S. marcescens* were greater than the range of concentrations tested, treatment with the stapled peptides resulted in partial inhibition of growth when compared to magainin II. The MICs of the panel, when tested on *B. cereus*, were very similar to the values obtained with *E. coli*. These results suggest that the double membrane structure of Gram-negatives does not protect the pathogens from AMP toxicity. Our MIC results with *E. durans* exhibited a 2 to 3-fold increase in antimicrobial activity. Of note, *E. durans* MIC measurements were conducted in the presence of 5% lysed horse blood for optimal *E. durans* growth. Since the solubility experiments demonstrated that the addition of bovine serum albumin (BSA) attenuates peptide activity, the serum proteins present in the horse blood may be binding to the AMPs and impeding their activity.

Understanding how the staple location affects the antimicrobial activity of AMPs can be crucial to refining peptide design. When comparing MIC values of the stapled panel, staple positions 2 and 6 consistently resulted in a much lower MIC value. However, staple positions 1 and 5 had the highest MIC value among the peptides in the panel across all 4 strains. Thus, when the staple location is on the hydrophobic face of the peptide, a marked increase in antimicrobial potency can be achieved. On the other hand, when the staple location was installed on the hydrophilic face, the gains in potency were lower.

Example 4: Hemolytic Activity of Stapled Magainin II Peptides

Figure 5:
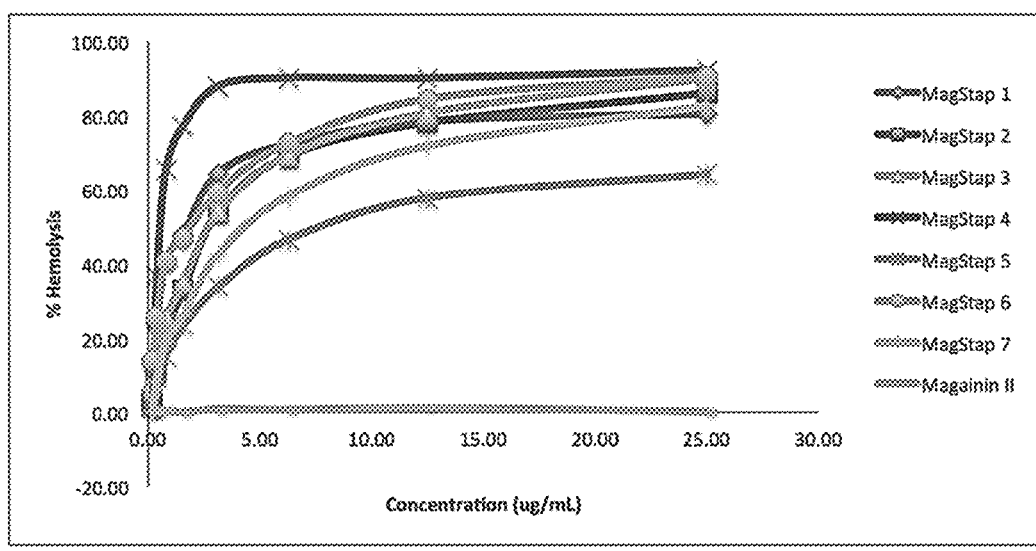
FIG. 5 is a series of line graphs depicting the hemolytic activity of magainin II and stapled analogues. Peptides were incubated with 1% (v/v) human red blood cells in phosphate-buffered solution for 1 hour at 37° C. and then the supernatant was isolated and the amount of hemoglobin released was measured at 540 nm. % hemolysis was calculated relative to an untreated control.

The ability of AMPs to distinguish between eukaryotic and bacterial membranes is central to their activity as it helps prevent injury to the host organism's cells. Nevertheless, a big obstacle in the field of AMP therapy is increasing AMP potency while minimizing injury to mammalian (e.g., human) cells. While increases in helicity and hydrophobicity often result in favorable gains in antimicrobial activity, increased helicity and hydrophobicity can also result in much lower membrane selectivity. In order to assess how selective the initial panel of stapled peptides were; the ability to lyse red blood cells isolated from healthy patient blood samples was measured (FIG. 5). Magainin II displayed no hemolytic activity across the span of concentrations tested, while the stapled analogues were all highly hemolytic even at concentrations below their MICs. Of the stapled analogues, MagStap 5 displayed the lowest hemolytic activity, while MagStap 4 had the highest hemolytic activity. One possible explanation for these results is that the hydrocarbon staple resulted in a significant increase in hydrophobicity as evidenced by the elution times on a C-18 HPLC column (see, e.g., Example 11).

Example 5: Synthesis of Stapled Pexiganan Analogues

Figures 6A, 6B:
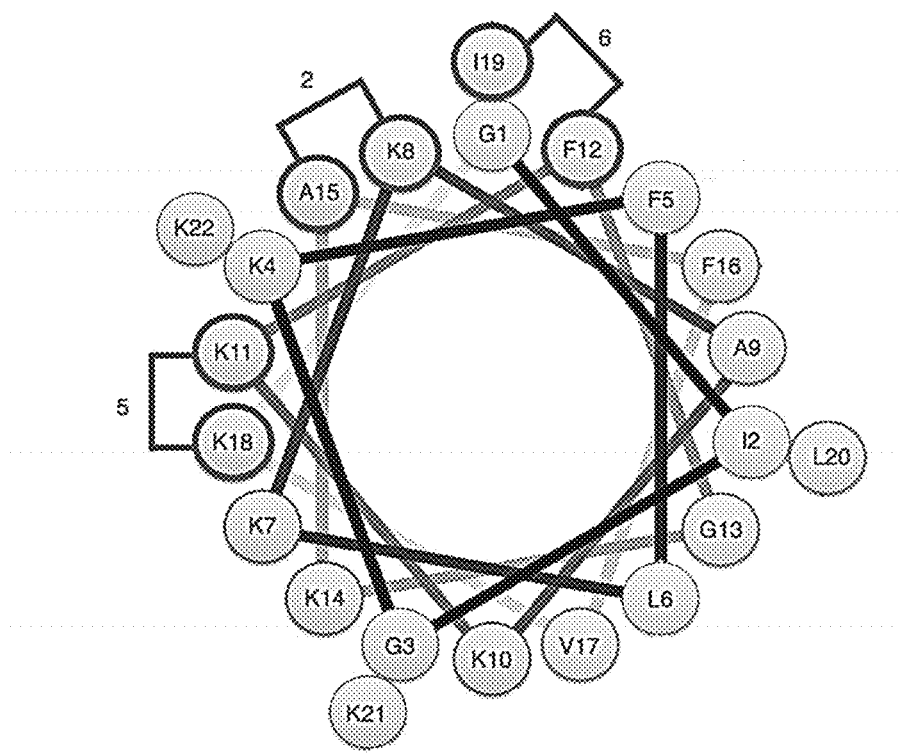
FIG. 6A is a depiction of the pexiganan amino acid sequence aligned with the sequences of stapled derivatives to show the positions of the i, i+7 staples. The amino acids set forth in this figure correspond to SEQ ID NOs: 2 and 185-187, numbered consecutively.
FIG. 6B is a helical wheel projection of the pexiganan amino acid sequence (SEQ ID NO: 2) with staple positions denoted by sequence numbers. Residues A15, K22, K4, K11, K18, K7, K14, G3, K21, and K10 are the hydrophilic amino acids and residues K8, G1, I19, F12, F5, F16, A9, I2, L20, G13, L6, and V17 are the hydrophobic amino acids.

Three Pexiganan analogues were synthesized where the staple was placed in the position corresponding to that used in MagStap2, MagStap5, and MagStap6 to test the locations that displayed the most and least activity (FIG. 6A and FIG. 6B).

Example 6: Helical Characterization of Stapled Pexiganan Analogues

Figure 7A:
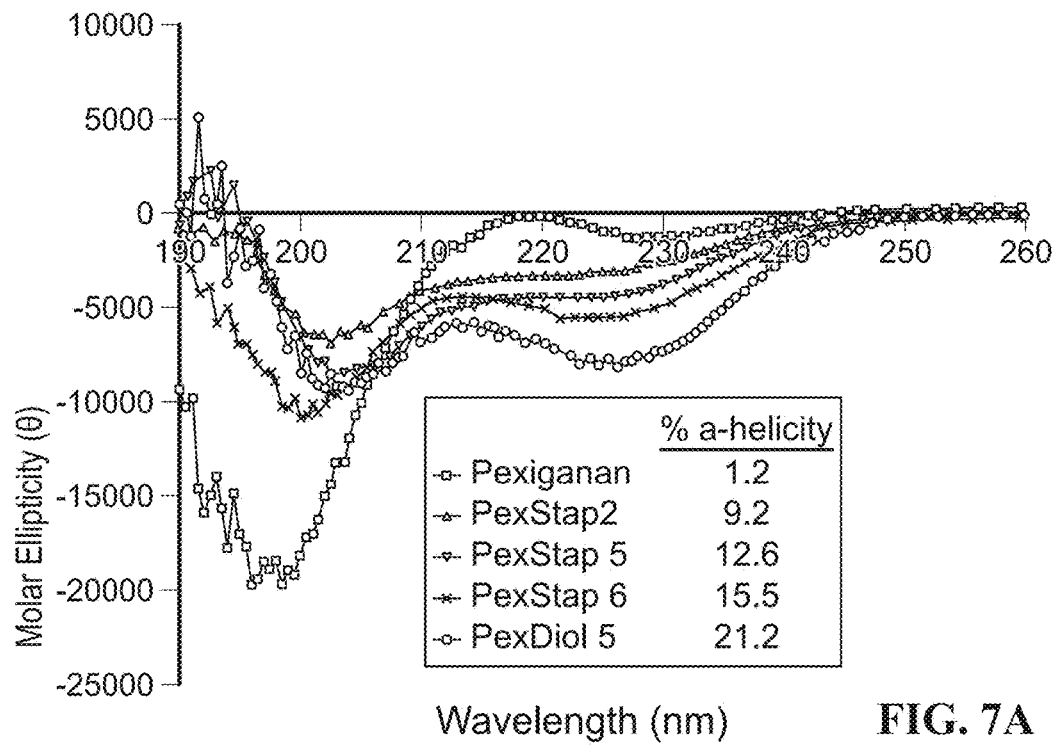
FIG. 7A is a series of line graphs depicting the CD spectra of pexiganan and stapled analogues in aqueous solution.
Figure 7B:
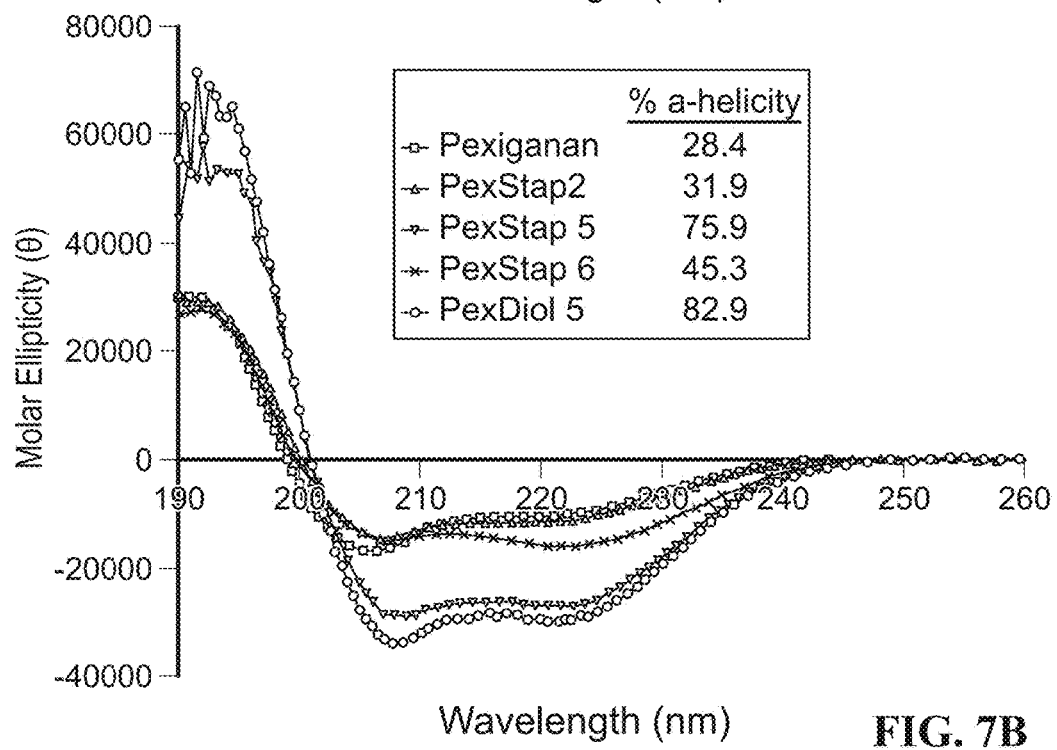
FIG. 7B is a series of line graphs depicting the CD spectra of pexiganan and stapled analogues in TFE:Water (1:1) mixture.

The helicity of Pexiganan and its stapled analogues in water in the presence and absence of the helicity inducer, TFE (50% v/v), were measured. In the absence of TFE, Pexiganan displayed little secondary structure in solution while the stapled analogues showed very low amounts of helical conformation (FIG. 7A). Upon the addition of TFE, Pexiganan, PexStap2, and PexStap6 displayed similar levels of helical conformation in the range of 25-35%. These results suggest that the electrostatic repulsion made the helical conformation less favorable (FIG. 7B). Furthermore, the PexStap5 analogue, where the staple was added to the hydrophilic side and replaced two lysine residues, displayed a much higher degree of helicity around 83%. This result further underscores the importance of electrostatic repulsion between residues on the hydrophilic side in determining the relative amount of helicity an AMP can adopt.

Example 7: Antimicrobial Activity of Stapled Pexiganan Analogues

Pexiganan and its stapled analogues were tested against the following strains of bacteria: *E. coli, S. marcescens, B. cereus, S. aureus*, and *P. aeruginosa*. The results of this study are presented in Table 4.

TABLE 4

Minimum inhibitory concentrations of pexiganan and stapled derivatives against Gram-negative and Gram-positive bacterial strains

| Peptide | Antimicrobial Activity MIC (µg/ml) | | | | |
| --- | --- | --- | --- | --- | --- |
| | E. coli | S. marcescens | B. cereus | S. aureus | P. aeruginosa |
| Pexiganan | 3.1 | >50 | 3.1 | 6.3 | 1.6 |
| PexStap 2 | 3.1 | >50 | 3.1 | 3.1 | 3.1 |
| PexStap 5 | 1.6 | >50 | 1.6 | 3.1 | 1.6 |
| PexStap 6 | 3.1 | >50 | 6.3 | 3.1 | 1.6 |
| PexDiol 5 | 1.6 | >50 | 3.1 | 3.1 | 1.6 |

The stapled pexiganan analogues did not exhibit a significant increase in antimicrobial activity. Their activity was mostly maintained across the strains that were tested and in the case of *S. marcescens*, the stapled analogues displayed partial growth inhibition when compared to pexiganan. Due to the mechanism of action of AMPs that requires the presence of a certain concentration of peptide for pore formation to occur, an upper limit in terms of peptide potency may have been reached. Nevertheless, the protease resistance and favorable pharmacokinetic profiles afforded by peptide stapling, represent potential benefits for stapled pexiganan AMPs compared to the unmodified peptide.

Example 8: Hemolytic Activity of Stapled Pexiganan Analogues

Figure 8:
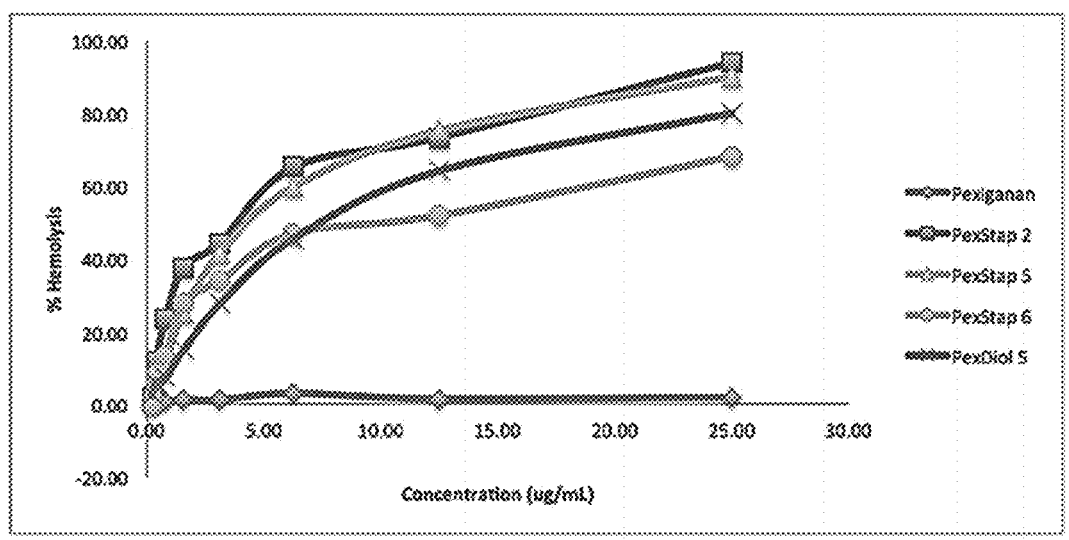
FIG. 8 is a series of line graphs depicting the hemolytic activity of pexiganan and stapled analogues. Peptides were incubated with 1% (v/v) human red blood cells in phosphate-buffered solution for 1 hour at 37° C. and then the supernatant was isolated and the amount of hemoglobin released was measured at 540 nm. % hemolysis was calculated relative to an untreated control.

When human red blood cells were incubated in the presence of stapled pexiganan peptides, a significant amount of hemolytic activity was detected as opposed to no hemolysis in the case of pexiganan (FIG. 8). However, when compared to the stapled magainin II panel, the pexiganan analogues displayed lower levels of hemolytic activity across the range of concentrations tested. The increase in cationic residues resulted in a decrease in the overall hydrophobicity of the peptides, which partially restored their membrane selectivity. In addition, PexStap5 displayed higher levels of hemolytic activity when compared to PexStap2 and PexStap6, providing further evidence that increased hydrophobicity reduces membrane selectivity. Interestingly, PexStap5 is more hemolytic than MagStap5 even though it is less hydrophobic. In terms of helicity, a certain threshold appears to exist, which when exceeded can drastically increase the hemolytic activity of an AMP (see, e.g., Example 11).

Example 9: Dihydroxylation of the Hydrocarbon Staple

While the addition of the hydrocarbon staple has resulted in significant improvements in antimicrobial activity there was also an increase in hemolytic activity was observed, which can be due to the hydrophobic nature of the hydrocarbon staple. Thus, one approach to retain antimicrobial potency enhancement, while mitigating hydrophobicity that can predispose to lysis, is to modulate the hydrophobicity of the staple itself; thus, the Sharpless dihydroxylation reaction was used to introduce two alcohol groups into the alkene group present in the staple. The presence of these two hydrophilic groups on the staple can reduce its hydrophibicity resulting in lower hemolytic activity. To test this hypothesis, a dihydroxylated form of PexStap5, referred to as PexDiolS, was synthesized.

First, the degree of helical folding in PexDiol 5 was measured and similar levels of helicity were found in the presence and absence of TFE (50% v/v) when compared to PexStap5 (FIG. 7). Second, the antimicrobial activity of PexDiolS was tested against our panel of bacterial pathogens. Antimicrobial activity was maintained in the presence of the diol moiety on the staple (Table 3). Finally, the hemolytic activity of PexDiolS was tested. Though PexDiolS displayed significant hemolytic activity across the range of concentrations tested, it was notably lower that the activity of PexStap5 (FIG. 8). This result validated the reasoning that the staple's hydrophobicity played a key role in the decrease in membrane selectivity.

Example 10: Aminohydroxylation of the Hydrocarbon Staple

While the diol moiety partially decreased the overall hydrophobicity of the peptides, adding a point charge through the addition of an amine moiety can further decrease the hydrophobicity of the staple. Furthermore, an amine handle on the staple provides an opportunity to attach other chemical groups to the staple that could further enhance antimicrobial activity. To this end, Sharpless aminohydroxylation reaction was used to modify the alkene group in PexStap2, PexStap5, and PexStap6 and generate PexAmino12, PexAmino15, and PexAmino16.

Figures 10, 11:
FIG. 10 is a depiction of the amino acid sequences of various pexiganan stapled analogues containing i+3, i+4, and i+7 staples (SEQ ID NOs: 253-258, respectively, in order of appearance). The arrows denote the direction of the staple scan or walk, in which the position of a staple spanning a fixed number of amino acids (e.g., 2, 3, or 6) is shifted one amino acid at a time down the length of the peptide.
FIG. 11 is a depiction of the amino acid sequences of the members of a magainin II i+4 and i+7 stapled peptide library (SEQ ID NOs: 135-168, respectively, in order of appearance). Amino acid B stands for the unnatural amino acid norleucine. X,X represents S5 pentenyl alanine pairs in i, i+4 stapled peptides and S5 pentenyl and $R_8$ octenyl alanine pairs in i, i+7 stapled peptides.
Figure 12:
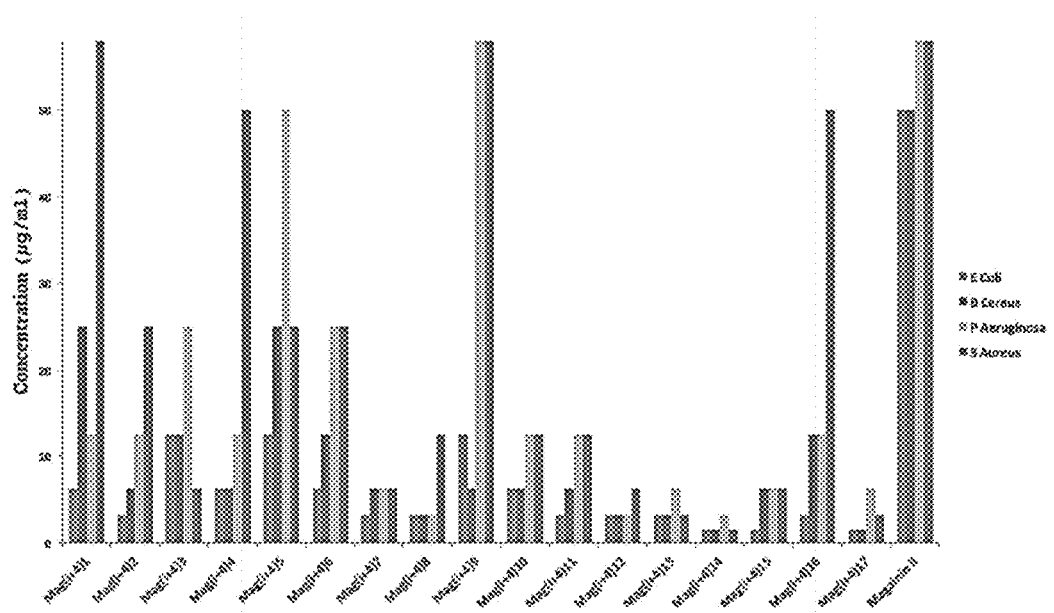
FIG. 12 is a bar graph depicting the minimum inhibitory concentrations (MIC) of magainin II i, i+4 stapled peptides against *Escherichia coli*, *Bacillus cereus*, *Pseudomonas aeruginosa*, and *Staphylococcus aureus*. MIC values over 50 μg/mL were not determined.
Figure 13:
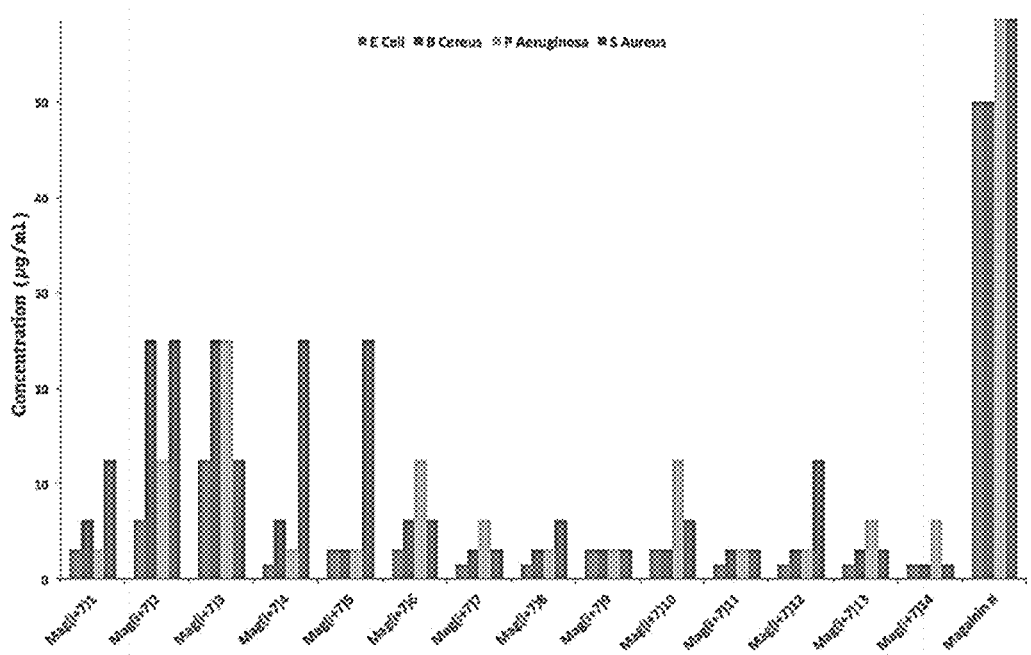
FIG. 13 is a bar graph depicting the MIC of magainin II i+7 stapled peptides against *Escherichia coli*, *Bacillus cereus*, *Pseudomonas aeruginosa*, and *Staphylococcus aureus*. MIC values over 50 μg/mL were not determined.
Figure 14:
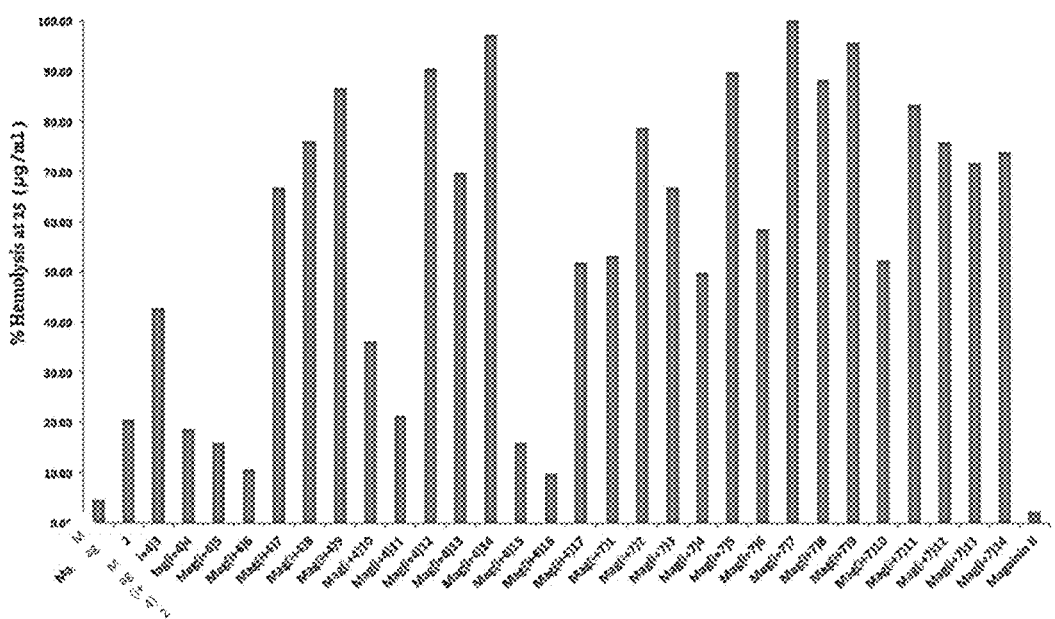
FIG. 14 is a bar graph depicting the hemolytic activity of magainin II i, i+4 and i, i+7 stapled peptides in 1% red blood cell suspension for 1 hour at 37° C. Activity was normalized to total lysis with 1% Triton-X100 solution.

Example 11: Design Principles for Generating Stapled AMPs with Microbial Vs Mammalian Membrane Selectivity A peptide library based on the sequence of magainin II was generated and all possible i, i+4, or i, i+7 staple insertion points were surveyed by sequentially moving the staple across the peptide sequence from its N- to C-terminus (FIG. 11). The antimicrobial activity of this library in four different bacterial pathogens that included Gram-positive and Gram-negative species were tested (FIG. 12, FIG. 13), and counter-screened for mammalian membrane lysis using a red blood cell (RBC) hemolytic activity assay (FIG. 14).

In general, the incorporation of a staple into the magainin II sequence resulted in greater antimicrobial activity compared to the unmodified sequence, with activity varying for differentially stapled species. Although the i+7 stapled derivatives were more active than the i+4 stapled compounds, the i+7 analogs were likewise lytic in the RBC hemolytic activity assay, consistent with the greater hydrophobic content of the i, i+7 staple. In contrast, the i+4 panel demonstrated a striking pattern of differential RBC lysis activity based on the periodicity of the staple insertion site (FIG. 14). Specifically, analysis of the topographic landscape of alpha-helical magainin II revealed that RBC lysis by i, i+4 stapled magainin peptides depended on whether the staple localized within an established hydrophobic patch of the helical surface or extended beyond this region, or even linking previously separated hydrophobic patches to yield a new continuous hydrophobic surface (FIG. 15A, B). For example, in the case of stapled derivative Mag(i+4)1, antimicrobial activity was increased substantially in *E. coli* and *P. aeruginosa* (both Gram-negative pathogens) displaying MICs of 6.2 and 12.5 µg/mL, respectively, compared to greater than or equal to 50 µg/mL for the unmodified peptide (Tables 5, 6, 7, FIG. 15C).

TABLE 6

MIC of magainin II and additional stapled derivatives against Gram-negative and Gram-positive bacterial strains

| | Antimicrobial Activity MIC (µg/ml) | | | | |
|---|---|---|---|---|---|
| Peptide | E. coli | B. cereus | P. aeruginosa | S. aureus | % Hemolysis at 25 µg/ml |
| Magainin II | 50 | >50 | >50 | >50 | 2.2 |
| Mag(i + 4)0 | 3.1 | 12.5 | 50 | >50 | 4.8 |
| Mag(i + 4)1 | 3.1 | 25 | 12.5 | >50 | 4.4 |
| Mag(i + 4)2 | 3.1 | 12.5 | 12.5 | 12.5 | 19.6 |
| Mag(i + 4)3 | 6.2 | 12.5 | 25 | 6.2 | 41.6 |
| Mag(i + 4)4 | 3.1 | 6.2 | 12.5 | 25 | 17.8 |
| Mag(i + 4)5 | 12.5 | 12.5 | 50 | 25 | 13.3 |
| Mag(i + 4)6 | 6.2 | 12.5 | 25 | 25 | 7.8 |
| Mag(i + 4)7 | 3.1 | 6.2 | 6.2 | 6.2 | 62.5 |
| Mag(i + 4)8 | 3.1 | 3.1 | 3.1 | 12.5 | 74.6 |
| Mag(i + 4)9 | 6.2 | 12.5 | >50 | >50 | 66.9 |
| Mag(i + 4)10 | 3.1 | 6.2 | 12.5 | 6.2 | 23.6 |
| Mag(i + 4)11 | 3.1 | 6.2 | 6.2 | 12.5 | 17.5 |
| Mag(i + 4)12 | 3.1 | 3.1 | 3.1 | 6.2 | 76.8 |
| Mag(i + 4)13 | 3.1 | 3.1 | 6.2 | 6.2 | 59.7 |
| Mag(i + 4)14 | 1.6 | 3.1 | 3.1 | 3.1 | 92.1 |
| Mag(i + 4)15 | 1.6 | 6.2 | 6.2 | 12.5 | 11.9 |
| Mag(i + 4)16 | 3.1 | 12.5 | 6.2 | 50 | 7.8 |
| Mag(i + 4)17 | 1.6 | 1.6 | 6.2 | 3.1 | 56.0 |
| Mag(i + 4)18 | 1.6 | 3.1 | 3.1 | 1.6 | 96.5 |
| Mag(i + 4)1, 15(A9K) | 1.6 | 25 | 3.1 | 50 | 2.4 |
| Mag(i + 4)2, 15(A9K) | 1.6 | 3.1 | 3.1 | 3.1 | 15.4 |

The peptides in Table 6 are SEQ ID NOs: 134, 69, and 135-154, numbered consecutively from top to bottom. The sequence of Mag(i+4)18 (SEQ ID NO: 152) is GIGKFLH-SAKKFGKAFVGXIBNX; the sequence of Mag(i+4)1,15 (A9K) (SEQ ID NO: 153) is GXGKFXHSKKKFG-KAXVGEXBNS; the sequence of Mag(i+4)2,15(A9K) (SEQ ID NO: 154) is GIXKFLXSKKKFG-KAXVGEXBNS.

Yet, even when the dose was increased to 25 µg/mL in the RBC hemolytic activity assay, only 5% hemolysis was observed for the stapled peptide, comparing favorably with the 2% hemolysis observed for the unmodified peptide at the same dose (Table 5, FIG. 15C). Thus, the properties of Mag(i+4)1 reflect a suitable therapeutic window for bacterial vs. mammalian membrane selectivity. In contrast, when the staple was moved to a location that imposes hydropho-

TABLE 5

MIC of magainin II and stapled derivatives against Gram-negative and Gram-positive bacterial strains

| | | Antimicrobial Activity MIC (µg/ml) | | | | % Hemolysis |
|---|---|---|---|---|---|---|
| Peptide | Sequence | E.coli | B.cereus | P.aeruginosa | S.aureus | at 25 µg/ml |
| Magainin II | GIGKFLHSAKKFGKAPVGEIBNS | 50 | >50 | >50 | >50 | 2.2 |
| Mag(i + 4)1 | GXGKFXHSAKKFGRAFVGEIBNS | 3.1 | 25 | 12.5 | >50 | 4.4 |
| Mag(i + 4)6 | GIGKFLXSAKXFGKAFVGEIBNS | 6.2 | 12.5 | 25 | 25 | 7.8 |
| Mag(i + 4)8 | GIGKFLHSXKKFXKAFVGEIBNS | 3.1 | 3.1 | 3.1 | 12.5 | 74.6 |
| Mag(i + 4)16 | GIGKFLHSAKKFGKAFXGEIXNS | 3.1 | 12.5 | 6.2 | 50 | 7.8 |

The peptides in Table 5 are SEQ ID NOs: 134, 135, 140, 142, and 150, numbered consecutively from top to bottom.

bicity at a prior site of hydrophilicity, such as in Mag(i+4)8, indiscriminate lytic activity was observed (Tables 5, 6, FIG.

15D). However, when the staple again occupies a previously hydrophobic region, microbial-selective lytic activity is restored (FIG. 15E). The properties of Mag(i+4)6 provide yet another example that highlights the importance of maintaining discontinuity in hydrophobic surface patches to achieve membrane selectivity: although the staple replaces two cationic amino acids in the sequence, the hemolytic activity at 25 μg/mL remains low at 11% (FIG. 15F). Whereas Mag(i+4)6 increases the overall hydrophobic surface area to a similar extent as seen in Mag(i+4)8 hemolysis is not increased in the case of Mag(i+4)6 because hydrophobic patch discontinuity is maintained.

Based on these results, other stapled peptides (e.g., AMP's not based on the sequence of magainin II) with at least two internally cross-linked or stapled amino acids, wherein the at least two amino acids are separated by two (i.e., i, i+3, shown in FIG. 1 and FIG. 2), three (i.e., i, i+4, shown in FIG. 1 and FIG. 2), or six (i.e., i, i+7, shown in FIG. 1 and FIG. 2; also see Table 7, below) amino acids were synthesized and assayed.

TABLE 7

MIC of magainin II and i + 7 stapled derivatives against Gram-negative and Gram-positive bacterial strains

| Peptide | Antimicrobial Activity MIC (μg/ml) | | | | % Hemolysis at 25 μg/ml |
| --- | --- | --- | --- | --- | --- |
| | E. coli | B. cereus | P. aeruginosa | S. aureus | |
| Magainin II | 50 | >50 | >50 | >50 | 2.2 |
| Mag(i + 7)1 | 3.1 | 3.1 | 3.1 | 12.5 | 49.9 |
| Mag(i + 7)2 | 3.1 | 6.2 | 12.5 | 12.5 | 69.3 |
| Mag(i + 7)3 | 6.2 | 12.5 | 25 | 12.5 | 52.5 |
| Mag(i + 7)4 | 1.6 | 6.2 | 3.1 | 25 | 42.6 |
| Mag(i + 7)5 | 3.1 | 3.1 | 3.1 | 6.2 | 87.0 |
| Mag(i + 7)6 | 3.1 | 6.2 | 25 | 6.2 | 47.1 |
| Mag(i + 7)7 | 3.1 | 3.1 | 6.2 | 3.1 | 95.5 |
| Mag(i + 7)8 | 1.6 | 3.1 | 3.1 | 6.2 | 85.4 |
| Mag(i + 7)9 | 3.1 | 3.1 | 3.1 | 3.1 | 94.6 |
| Mag(i + 7)10 | 3.1 | 6.2 | 6.2 | 3.1 | 53.1 |
| Mag(i + 7)11 | 1.6 | 3.1 | 1.6 | 3.1 | 84.8 |
| Mag(i + 7)12 | 1.6 | 3.1 | 3.1 | 12.5 | 80.3 |
| Mag(i + 7)13 | 1.6 | 3.1 | 6.2 | 12.5 | 63.6 |
| Mag(i + 7)14 | 1.6 | 1.6 | 6.2 | 1.6 | 68.1 |

The peptides in Table 7 are SEQ ID NOs: 134 and 155-168, numbered consecutively from top to bottom.

Figures 16A, 16B, 16C:
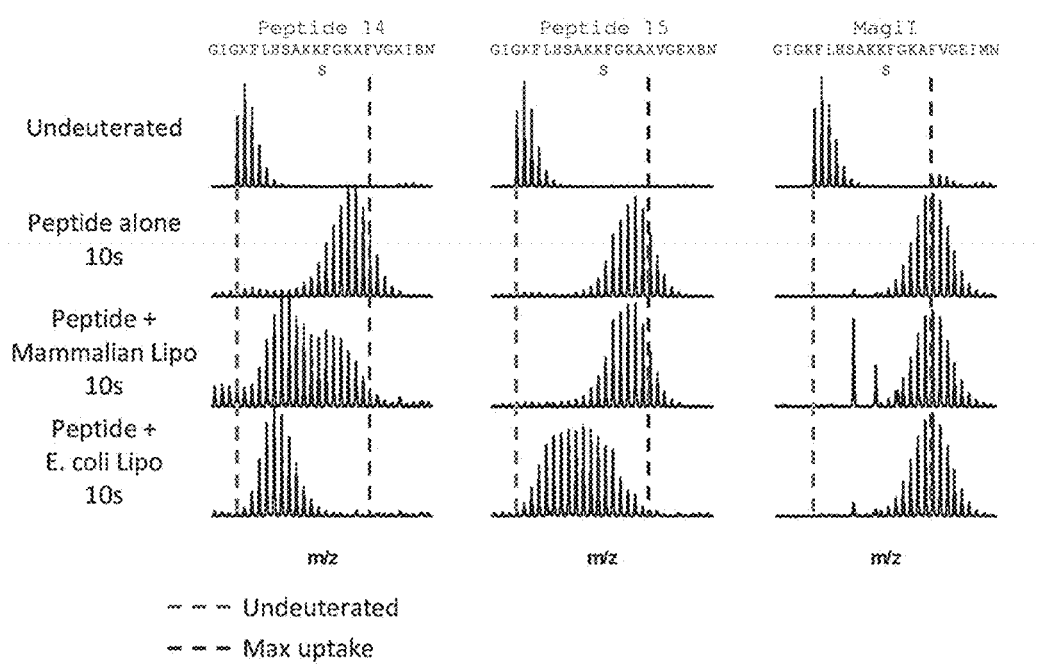
FIG. 16A is a plot depicting the specificity of the interaction of magainin II stapled derivative Peptide 14 (SEQ ID NO: 260) with liposomes simulating bacterial (e.g., *E. coli*) or mammalian cell membranes using hydrogen-deuterium exchange mass spectrometry.
FIG. 16B is a plot depicting the specificity of the interaction of magainin II stapled derivative Peptide 15 (SEQ ID NO: 261) with liposomes simulating bacterial (e.g., *E. coli*) or mammalian cell membranes using hydrogen-deuterium exchange mass spectrometry.
FIG. 16C is a plot depicting the specificity of the interaction of magainin II (SEQ ID NO: 262) with liposomes simulating bacterial (e.g., *E. coli*) or mammalian cell membranes using hydrogen-deuterium exchange mass spectrometry.

Hydrogen-deuterium exchange mass spectrometry experiments assessing the interaction of magainin II, Mag (i+4)14, and Mag(i+4)15 with liposomes simulating mammalian (DOPC:cholesterol (9:1)) or bacterial (DOPC:DOPG (8:2)) cell membranes show that Mag(i+4)14 interacts indiscriminately with mammalian and bacterial membranes (since co-incubation with liposomes simulating those membranes protects the Mag(i+4)14 peptide from deuteration). See FIG. 16. In contrast, Mag(i+4)15 selectively interacts with bacterial membranes, but not mammalian membranes; only co-incubation with liposomes simulating bacterial membranes shields Mag(i+4)15 peptides from deuteration. The parent peptide (magainin II) is deuterated in all conditions, as it interacts poorly with both bacterial and mammalian membranes at the concentration used.

Example 12: The Effect of Charge Distribution on Antimicrobial Peptide Selectivity and Activity The positive charges on Magainin align on the hydrophilic side near the N-terminus, and a glutamic acid residue is conserved near the C-terminus. To determine the effect of moving a positive charge and a negative charge on the activity and selectivity of stapled AMPs (STAMPs), a library of peptides was generated, where a lysine or glutamic acid residue was installed at various positions (FIGS. 17 and 18). Mag(i+4)15 was chosen as a model stapled scaffold due to the large increase in antimicrobial activity and modest increase in hemolytic activity compared to the unstapled peptide.

From the lysine scan library, a general trend of decreased hemolytic activity was observed no matter where the lysine residue was installed (Table 8). This trend suggests that non-selective toxicity, for example, lysis of mammalian membranes in addition to bacterial membranes, is predominantly due to the hydrophobic patch of the surface of the peptide.

Antimicrobial activity was highly dependent on the position of the positive charge placement. Gram-positive activity was more easily disrupted than was Gram-negative activity when a hydrophobic residue was mutated to lysine. In some instances, such as in Mag(i+4)15(A9K), Gram-positive activity was greatly attenuated while Gram-negative activity was unaffected (Table 8).

In comparison to the parent STAMP template, the glutamic acid scan library exhibited an overall lower hemolytic activity, as was observed from the lysine scan library (Table 9). However, the antimicrobial activity was attenuated in the majority of cases, and highlights the role of positive charge in the antimicrobial activity of AMPs. Whenever a lysine residue was mutated, antimicrobial activity was reduced across the bacterial panel. These data are consistent with the observation that any reduction in the positive charge of magainin II notably impairs antimicrobial activity. The sensitivity of Gram-positive pathogens to particular glutamic acid mutations was more pronounced than for Gram-negative bacteria, as observed from the lysine scan library. For example, when a negative charge was added near the C-terminus, such as Mag(i+4)15(G18E) and Mag(i+4)15 (N22E), only a slight reduction in peptide activity was observed (Table 9). This result supports the assertion that a dipole moment within magainin II helps maintain selective lytic activity.

TABLE 8

MIC of magainin II-lysine derivatives against Gram-negative and Gram-positive bacterial strains

| Peptide | Antimicrobial Activity MIC (μg/ml) | | | | % Hemolysis at 25 μg/ml |
| --- | --- | --- | --- | --- | --- |
| | E. coli | B. cereus | P. aeruginosa | S. aureus | |
| Mag(i + 4)15 | 1.6 | 6.2 | 6.2 | 12.5 | 11.9 |
| Mag(i + 4)15(S23K) | 1.6 | 6.2 | 3.1 | 50 | 5.0 |

TABLE 8-continued

MIC of magainin II-lysine derivatives against Gram-negative and Gram-positive bacterial strains

| Peptide | Antimicrobial Activity MIC (µg/ml) | | | | % Hemolysis at 25 µg/ml |
|---|---|---|---|---|---|
| | E. coli | B. cereus | P. aeruginosa | S. aureus | |
| Mag(i + 4)15(N22K) | 1.6 | 3.1 | 3.1 | 12.5 | 12.0 |
| Mag(i + 4)15(B21K) | 1.6 | 25 | 6.2 | >50 | 3.7 |
| Mag(i + 4)15(E19K) | 1.6 | 6.2 | 3.1 | 12.5 | 7.1 |
| Mag(i + 4)15(G18K) | 1.6 | 3.1 | 3.1 | 12.5 | 10.1 |
| Mag(i + 4)15(V17K) | 3.1 | 50 | 12.5 | >50 | 2.2 |
| Mag(i + 4)15(A15K) | 3.1 | 6.2 | 3.1 | 25 | 4.1 |
| Mag(i + 4)15(G13K) | 3.1 | >50 | 12.5 | >50 | 1.8 |
| Mag(i + 4)15(F12K) | 3.1 | >50 | 12.5 | >50 | 2.0 |
| Mag(i + 4)15(A9K) | 3.1 | >50 | 12.5 | >50 | 1.9 |
| Mag(i + 4)15(S8K) | 1.6 | 3.1 | 6.2 | 6.2 | 3.4 |
| Mag(i + 4)15(H7K) | 1.6 | 3.1 | 3.1 | 6.2 | 3.1 |
| Mag(i + 4)15(L6K) | 3.1 | >50 | 12.5 | >50 | 1.9 |
| Mag(i + 4)15(F5K) | 3.1 | >50 | 12.5 | >50 | 1.7 |
| Mag(i + 4)15(G3K) | 1.6 | 6.2 | 3.1 | 12.5 | 3.8 |
| Mag(i + 4)15(I2K) | 1.6 | 12.5 | 3.1 | 25 | 2.3 |
| Mag(i + 4)15(G1K) | 1.6 | 12.5 | 3.1 | 25 | 4.5 |

The peptides in Table 8 are SEQ ID NOs: 149 and 32-48, numbered consecutively from top to bottom.

TABLE 9

MIC of magainin II-glutamic acid derivatives against Gram-negative and Gram-positive bacterial strains

| Peptide | Antimicrobial Activity MIC (µg/ml) | | | | % Hemolysis at 25 µg/ml |
|---|---|---|---|---|---|
| | E. coli | B. cereus | P. aeruginosa | S. aureus | |
| Mag(i + 4)15 | 1.6 | 6.2 | 6.2 | 12.5 | 11.9 |
| Mag(i + 4)15(G1E) | 12.5 | >50 | 50 | >50 | 4.1 |
| Mag(i + 4)15(I2E) | 12.5 | >50 | >50 | >50 | 3.6 |
| Mag(i + 4)15(G3E) | 3.1 | 12.5 | 12.5 | 50 | 3.9 |
| Mag(i + 4)15(K4E) | 12.5 | 50 | >50 | >50 | 2.2 |
| Mag(i + 4)15(F5E) | 50 | >50 | >50 | >50 | 0.5 |
| Mag(i + 4)15(L6E) | 50 | >50 | >50 | >50 | 1.1 |
| Mag(i + 4)15(H7E) | 3.1 | 6.2 | 12.5 | 25 | 2.9 |
| Mag(i + 4)15(S8E) | 3.1 | 12.5 | 12.5 | 50 | 2.9 |
| Mag(i + 4)15(A9E) | 50 | >50 | >50 | >50 | 0.6 |
| Mag(i + 4)15(K10E) | 6.2 | >50 | >50 | >50 | 2.4 |
| Mag(i + 4)15(K11E) | 6.2 | 12.5 | >50 | 50 | 2.9 |
| Mag(i + 4)15(F12E) | 50 | >50 | >50 | >50 | 0.6 |
| Mag(i + 4)15(G13E) | 25 | >50 | >50 | >50 | 2.2 |
| Mag(i + 4)15(K14E) | 12.5 | 50 | >50 | >50 | 3.3 |
| Mag(i + 4)15(A15E) | 3.1 | 25 | 25 | 50 | 3.8 |
| Mag(i + 4)15(V17E) | 50 | >50 | >50 | >50 | 0.5 |
| Mag(i + 4)15(G18E) | 3.1 | 6.2 | 12.5 | 12.5 | 4.8 |
| Mag(i + 4)15(B21E) | 25 | >50 | >50 | >50 | 0.8 |
| Mag(i + 4)15(N22E) | 3.1 | 12.5 | 12.5 | 25 | 3.4 |
| Mag(i + 4)15(S23E) | 3.1 | 12.5 | 12.5 | 25 | 4.9 |

The peptides in Table 9 are SEQ ID NOs: 149 and 49-68, numbered consecutively from top to bottom.

In addition to the positive and negative charge scan study, selective histidine mutations of the AMP compounds were generated. The positive charge of the histidine side chain is "softer" than the lysine side chain due to resonance within the imidazole. In addition, the $pK_a$ of the imidazole side chain is close to 6, such that at physiological conditions, the residue is not protonated as extensively as is the side chain of lysine. Due to the negatively charged environment close to a bacterial membrane, the pH adjacent to the bacterial membrane is likely below 6, and can cause histidine residues to be protonated. In addition, antimicrobial peptides, such as histatins, rely on the charge switching behavior of histidine to modulate peptide activity and selectivity. The effect of installing histidines to regions close to the hydrophilic face of magainin II that would extend the positively charged region in the context of a bacterial membrane and increase the likelihood of membrane penetration was tested (Table 10). In this exemplary peptide library, residues G3, S8, A15, and G18 were mutated. Overall, the mutations slightly reduced hemolytic activity and resulted in modest gains in antimicrobial activity. The most effective mutant of the group was Mag(i+4)15(S8H), where an increase in activity across the panel of bacteria tested was observed with a modest decrease in hemolytic activity. Thus, the results demonstrate the utility of installing histidine residues to selectively increase antimicrobial activity, while preserving selectivity, of AMP drug candidates.

Example 13: The Effect of the Helical Bend on Antimicrobial Activity of AMPs The α-helical nature of AMPs promotes interaction with membranes to induce bacterial lysis. However, some AMP sequences possess a helix disruptor residue, such as glycine or proline, close to the center of the peptides. To determine the role of helical disruptors in AMP sequences, a library of peptides in which the residue G13 was mutated into helix promoting residues like alanine and 2-aminoisobutyric acid (Aib) or helix disruptors, such as proline, hydroxyproline, D-alanine and D-lysine were synthesized (Table 10). The helix promoters resulted in an increase in antimicrobial activity in both Gram-positive and Gram-negative pathogens. Yet, a concurrent increase in hemolytic activity was observed, which is likely due to the hydrophobic nature of alanine and Aib. In contrast, the proline and hydroxyproline mutations resulted in an overall decrease in lytic activity of both bacterial and mammalian membranes. For the d-alanine mutant stapled AMP, an increase in antimicrobial activity was observed with a concurrent decrease in hemolytic activity. In terms of hydrophobicity, the two enantiomeric forms of alanine are identical. However, d-alanine can disrupt a helix. These results suggest that AMP selectivity can be achieved even in compounds that do not possess a high level of helical rigidity.

TABLE 10

MIC of magainin II with helical disruptors against Gram-negative and Gram-positive bacterial strains

| Peptide | Antimicrobial Activity MIC (µg/ml) | | | | % Hemolysis at 25 µg/ml |
| --- | --- | --- | --- | --- | --- |
| | E. coli | B. cereus | P. aeruginosa | S. aureus | |
| Mag(i + 4)15 | 1.6 | 6.2 | 6.2 | 12.5 | 11.9 |
| Mag(i + 4)15(G3H) | 1.6 | 6.2 | 12.5 | 25 | 5.1 |
| Mag(i + 4)15(S8H) | 1.6 | 3.1 | 3.1 | 3.1 | 8.7 |
| Mag(i + 4)15(A15H) | 3.1 | 6.2 | 12.5 | 12.5 | 4.7 |
| Mag(i + 4)15(G18H) | 1.6 | 3.1 | 6.2 | 6.2 | 6.8 |
| Mag(i + 4)15(G13I) | 1.6 | 3.1 | 3.1 | 3.1 | 71.5 |
| Mag(i + 4)15(G13P) | 3.1 | 25 | 25 | >50 | 2.0 |
| Mag(i + 4)15(G13&) | 12.5 | >50 | 50 | >50 | 1.3 |
| Mag(i + 4)15(G13A) | 1.6 | 3.1 | 6.2 | 3.1 | 20.5 |
| Mag(i + 4)15(G13a) | 1.6 | 6.2 | 3.1 | 6.2 | 4.3 |
| Mag(i + 4)15(G13k) | 3.1 | 50 | 25 | >50 | 2.1 |

The peptides in Table 10 are SEQ ID NOs: 149 and 73-82, numbered consecutively from top to bottom.

Example 14: Integrating Insights from the Charge Scan Libraries and Histidine Mutants A series of compounds based on the results of the above staple scanning and mutation scanning libraries were designed. Using the double stapledSTAMP candidates, Mag(i+4)1,15 (A9K) and Mag(i+4)2,15 (A9K), a panel of peptide derivatives was generated in which mutant positions were chosen based on previous data (Table 11). For example, a glutamic acid mutation (N21E) was installed in these double-stapled STAMPs with the goal of increasing selectivity of Mag(i+4)2,15, one of the most potent double stapled AMPs. Other mutations were incorporated to make up for potential losses in antimicrobial activity and/or to increase membrane selectivity. In this panel, Mag(i+4)2,15 (I2K, A9H) exhibited only mildly attenuated antimicrobial activity, but the previously observed 16% hemolytic activity was completely eliminated. Enhancing positive charge by installing additional histidine mutations was shown to maintain or improve antimicrobial activity while ensuring that selectivity was preserved or improved.

TABLE 11

MIC of magainin II derivatives against Gram-negative and Gram-positive bacterial strains

| Peptide | Antimicrobial Activity MIC (µg/ml) | | | | % Hemolysis at 25 µg/ml |
| --- | --- | --- | --- | --- | --- |
| | E. coli | B. cereus | P. aeruginosa | S. aureus | |
| Mag(i + 4)15 | 1.6 | 6.2 | 6.2 | 12.5 | 11.9 |
| Mag(i + 4)2,15(I2K, A9K, G18H) | 3.1 | 12.5 | 3.1 | 25 | 2.2 |

TABLE 11-continued

MIC of magainin II derivatives against Gram-negative and Gram-positive bacterial strains

| Peptide | Antimicrobial Activity MIC (μg/ml) | | | | % Hemolysis |
|---|---|---|---|---|---|
| | E. coli | B. cereus | P. aeruginosa | S. aureus | at 25 μg/ml |
| Mag(i + 4)2,15(I2K, A9H) | 3.1 | 6.2 | 6.2 | 12.5 | 0.6 |
| Mag(i + 4)2,15(I2K, A9H, N21E) | 3.1 | 25 | 12.5 | 50 | 1.8 |
| Mag(i + 4)2,15(I2K, A9H, G18H, N21E) | 3.1 | 6.2 | 6.2 | 25 | 4.0 |
| Mag(i + 4)1,15(S8H, A9K, G18H, N21E) | 3.1 | 50 | 12.5 | >50 | 4.2 |

The peptides in Table 11 are SEQ ID NOs: 149 and 170-174, numbered consecutively from top to bottom.

Example 15: Validation of STAMP Hydrophobicity Patch

Figures 20, 21, 22A, 22B, 22C:
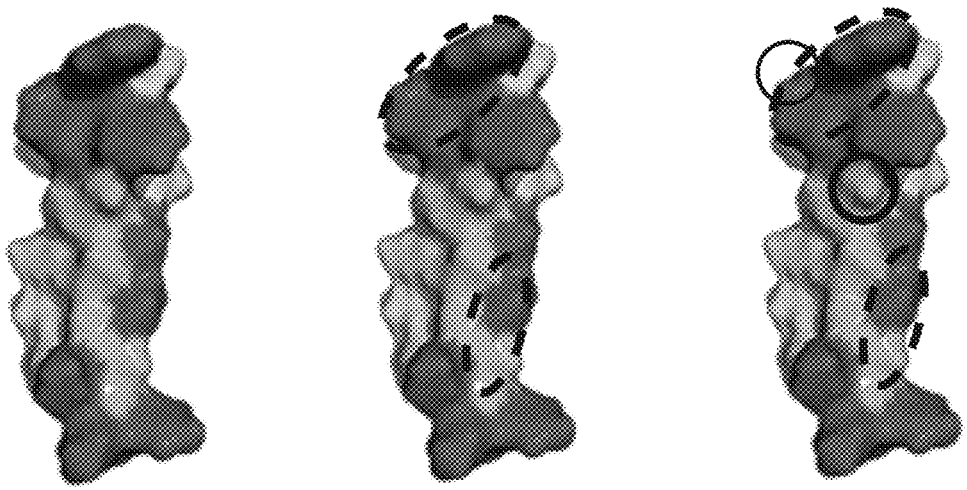
FIG. 20 is a depiction of the amino acid sequences of the members of a second generation of magainin II double staple analogues (SEQ ID NOs: 170-174, respectively, in order of appearance). Amino acid B stands for the non-natural amino acid norleucine.
FIG. 21 is a depiction of sequences of pleurocidin-NH$_2$ and two rationally designed double staple analogues (SEQ ID NOs: 175-177, respectively, in order of appearance).
FIG. 22A is a model of the hydrophobic face of pleurocidin-NH$_2$. Regions colored in dark gray have highly hydrophobic residues (F, V, L, Y, W); regions colored in light gray have relatively low hydrophobicity residues (G A, T); regions colored in very light gray represent charged/hydrophilic residues (H, K, E, N, S); regions marked with dashed ellipses depict the hydrophobic i+4 double staple positions; the region circled depicts a lysine mutation. Surfaces were generated using PDB file 1Z64.
FIG. 22B is a model of the hydrophilic face of Pleu(i+4)1,15. Regions colored in dark gray have highly hydrophobic residues (F, V, L, Y, W); regions colored in light gray have relatively low hydrophobicity residues (G A, T); regions colored in very light gray represent charged/hydrophilic residues (H, K, E, N, S); regions marked with dashed ellipses depict the hydrophobic i+4 double staple positions; the region circled depicts a lysine mutation. Surfaces were generated using PDB file 1Z64.
FIG. 22C is a model of the hydrophobic face of Pleu(i+4)1,15(A9K). Regions colored in dark gray have highly hydrophobic residues (F, V, L, Y, W); regions colored in light gray have relatively low hydrophobicity residues (G A, T); regions colored in very light gray represent charged/hydrophilic residues (H, K, E, N, S); regions marked with dashed ellipses depict the hydrophobic i+4 double staple positions; the region circled depicts a lysine mutation. Surfaces were generated using PDB file 1Z64.

To study the significance of the hydrophobicity patch, antimicrobial peptide pleurocidin, which is found on the skin of winter flounder, was selected. Pleurocidin exhibits antimicrobial activity against both Gram-positive and Gram-negative pathogens with low hemolytic activity. However, the unstructured nature of this peptide is a has prevented in vivo utility. Using the NMR structure of pleurocidin in the presence of negatively charge micelles, the hydrophobic surface areas within the α-helical folded structure was identified (FIG. 22A). A double staple was then inserted within the confines of those hydrophobic regions (FIG. 22B). To create a discontinuous hydrophobic face, thereby reducing the risk of mammalian cell lysis while preserving antimicrobial activity (based on the experiments described above), the A9 residue was mutated to a lysine (FIG. 22C). When tested against Gram-positive and Gram-negative pathogens, the STAMP constructs exhibited improved antimicrobial activities that were one dilution range better than the parent unstapled peptide. This improvement in antimicrobial activity of the double stapled AMP, Pleu(i+4)1,15 (A9K), was achieved while maintaining low hemolytic activity similar to that of Mag(i+4)2,15 (A9K) (Table 12).

TABLE 12

MIC of pleurocidin derivatives against Gram-negative and Gram-positive bacterial strains

| Peptide | Antimicrobial Activity MIC (μg/ml) | | | | % Hemolysis |
|---|---|---|---|---|---|
| | E. coli | B. cereus | P. aeruginosa | S. aureus | at 25 μg/ml |
| Pleurocidin-NH2 | 3.1 | 6.2 | 3.1 | 6.2 | 0.5 |
| Pleu(i + 4)1,15 | 1.6 | 3.1 | 1.6 | 1.6 | 88.2 |
| Pleu(i + 4)1,15(A9K) | 1.6 | 3.1 | 1.6 | 3.1 | 16.3 |

The peptides in Table 12 are SEQ ID Nos: 175-177, numbered consecutively from top to bottom.

Methods Used in Examples

Solid Phase Peptide Synthesis

Fmoc-based solid-phase peptide synthesis was used to synthesize the antimicrobial peptides and their stapled derivatives. To achieve the various staple lengths, α-methyl, α-alkenyl amino acids were used flanking two, three, or six residues. The $R_8$ residue was incorporated at position i and $S_5$ at position i+3, while two $S_5$ residues were used at the i and i+4 locations, and an $R_8$ at position i and $S_5$ at i+7 [29]. Alternative stapling amino acid couples can also be used to generate the corresponding staples (e.g., $R_3/S_5$ or $S_3/R_5$ for i, i+3; $R_8/R_5$ for i, i+4; $S_8/R_5$ for i, i+7). For the stapling reaction, Grubbs first-generation ruthenium catalyst dissolved in dichloroethane was added to the peptides while still on resin. To ensure maximal conversion, three to five rounds of stapling were performed. Once stapled, the peptides were cleaved off the resin using trifluoroacetic acid, then precipitated using a hexane:ether (1:1) mixture, and afterwards they were air dried and purified using LC-MS. We performed amino acid analysis both to precisely determine the amount of peptide purified and to ensure the correct sequence was made Circular Dichroism Spectroscopy:

Compounds were dissolved in an aqueous solution (e.g. 5 mM potassium phosphate solution at pH 7, or distilled $H_2O$, to concentrations of 25-50 μM). Circular dichroism (CD) spectra were obtained on a spectropolarimeter (Aviv) using standard measurement parameters (e.g., temperature, 37° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide was calculated by dividing the mean residue ellipticity by the reported value for a model helical decapeptide (see, e.g., Yang et al., *Meth Enzymol.* 130:208 (1986)).

Antimicrobial Activity Assay:

The following microbroth dilution protocol was adapted to determine the minimum inhibitory concentration (MIC) of each peptide. First, Mueller-Hinton broth (MHB) was passed through an anion exchange column to remove polyanionic species and generate refined MHB. This refined broth was then used in the standard microbroth dilution protocol devised by Hancock and coworkers for 96 well plates (note: No BSA was used in the protocol because initial studies revealed that it could interfere with peptide activity). Briefly, bacterial cells was grown overnight in refined MHB at 37° C. and then diluted and allowed to grow again for several hours. Serial dilutions of peptide stocks in water (10 µl) were prepared using clear round-bottom polypropylene 96-well plates. Then 90 µl of bacteria in refined MHB was added to give a final inoculum of 5×10$^5$ CFU/ml. The plates were then covered with porous tape to reduce evaporation, and incubated for 20-24 hours at 37° C. The MIC is the minimum peptide concentration at which no visible growth was observed.

Hemolytic Activity Assay:

For the determination of hemolytic activity, human blood samples were centrifuged to isolate red blood cells (RBCs), which are then washed and suspended in phosphate-buffered saline to yield a 1% (v/v) suspension. The suspension was then added to serial dilutions of peptide stocks in water in clear round-bottom polypropylene 96-well plates and the plates were incubated for 1 hour at 37° C. After incubation, the plates were centrifuged and the supernatant was isolated to determine the amount of hemoglobin released using a spectrophotometer (570 nm), according to the equation: % Hemolysis=(Treated Absorbance−Untreated Control Absorbance)/(1% Triton-X100 Treated Absorbance−Untreated Control Absorbance). The minimum hemolytic concentration (MHC) is the peptide concentration at which there is less than 1% hemoglobin release.

OTHER ASPECTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patent applications, patents, and other publications cited herein are incorporated by reference in their entireties.

---

What is claimed is:

1. A therapeutic compound comprising a cross-linked amino acid sequence having the formula:

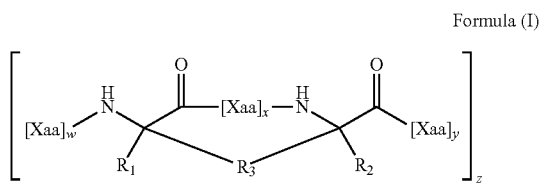

Formula (I)

or a pharmaceutically acceptable salt thereof,
wherein:
each $R_1$ and $R_2$ is independently H, alkyl, alkenyl, alkynyl, arylalkyl, cycloalkylalkyl, heteroarylalkyl, or heterocyclylalkyl, any of which is substituted or unsubstituted;
each $R_3$ is independently alkylene, alkenylene, or alkynylene, any of which is substituted or unsubstituted;
each x is 3 or 6;
each w and y is independently 1, 2, 3, 4, 5, 6, 7, 8, 9, 10, 11, 12, 13, 14, 15, 16, 17, 18, 19, or 20;
z is 1, 2, 3, or 4; and
each Xaa is independently an amino acid,
wherein the cross-linked amino acid sequence has 3, 4, 5, 6, 7, 8 or 9 amino acid substitutions relative to the sequence set forth in SEQ ID NO:3;
wherein the substitutions are:
(a) two or more amino acid substitutions with stapling amino acids that are internally cross-linked; and
(b) one or more of: (i) a substitution with a basic amino acid; (ii) a substitution with a histidine; (iii) a substitution with a D-alanine; (iv) a substitution with an alanine; and (v) a substitution of a methionine with a norleucine;
wherein at least one of the substitutions of (b) is selected from the group consisting of: (i) a substitution with a lysine at position 9 of SEQ ID NO:3; (ii) a substitution with a histidine, and (iii) a substitution with a glutamic acid;
wherein the cross-linked amino acid sequence has an alpha helical conformation; and wherein the compound exhibits an increased antibacterial effect against at least one bacterium relative to an un-cross-linked corresponding sequence set forth in SEQ ID NO:3.

2. The compound of claim 1, wherein $R_3$ is $C_8$ alkylene, $C_8$ alkenylene, or $C_8$ alkynylene; the sum of x, w, and y is at least 10; and z is 1 or 2.

3. The compound of claim 1, wherein $R_3$ spans from one to two turns on an α-helix.

4. The compound of claim 1, wherein the cross-linked amino acid sequence has 3, 4, or 5 amino acid substitutions relative to the sequence set forth in SEQ ID NO:3.

5. The compound of claim 1, wherein the cross-linked amino acid sequence has 3 or 4 amino acid substitutions relative to the sequence set forth in SEQ ID NO:3.

6. The compound of claim 1, wherein the bacterium is *Mycobacterium tuberculosis*.

7. The compound of claim 1, wherein the compound comprises a sequence selected from the group consisting of SEQ ID NOs: 41, 49-68, and 73-76.

8. The compound of claim 1, wherein the $R_3$ is substituted by dihydroxylation and/or aminohydroxylation.

9. The compound of claim 1, wherein z=1.

10. The compound of claim 1, wherein the cross-linked amino acid sequence has 3, 4, 5, 6, 7, 8 or 9 amino acid substitutions relative to the amino acid sequence set forth in SEQ ID NO:3, wherein one or more of the amino acid substitution(s) are at any of positions 1-3, 7-9, 13, 15, 18, 19, or 21-23 of SEQ ID NO: 3 and is/are selected from the group consisting of G1K, I2K, G3K, H7K, S8K, S8A, A9H, A9K, A15K, G13A, G18K, G18A, E19K, N22K, M21K, S23K, G3E, H7E, S8E, G18E, N22E, S23E, G3H, S8H, A15H, G18H, and substitution of M21 with a norleucine (M21B).

11. A pharmaceutical composition comprising the compound of claim 10.

12. A pharmaceutical composition comprising the therapeutic compound of claim 1.

13. The therapeutic compound of claim 1, wherein x is 3.

14. The therapeutic compound of claim 1, wherein the cross-linked amino acid sequence has 3, 4, 5, 6, 7, 8, or 9 amino acid substitutions relative to the amino acid sequence set forth in SEQ ID NO:3, wherein one or more of the amino acid substitution(s) are at any of positions 1-3, 7-9, 13, 15, 18, 19, or 21-23 of SEQ ID NO: 3 and is/are selected from the group consisting of M21K, G3E, H7E, S8E, G18E, N22E, S23E, and substitution of M21 with a norleucine (M21B).

15. The therapeutic compound of claim 1, wherein the stapling amino acid is an α,α-disubstituted amino acid.

16. The therapeutic compound of claim 1, wherein the stapling amino acid is S5 [(S)-2-(4-pentenyl)Alanine] or R5 [(R)-2-(4-pentenyl)Alanine].

17. The therapeutic compound of claim 1, wherein the at least one bacterium is *E. coli*.

18. A method of treating an infection caused by a bacterium, the method comprising administering a therapeutically-effective amount of the therapeutic compound of claim 1 to a subject having, or at risk of having, the infection caused by the bacterium.

19. A method of inhibiting the growth of a bacterium, the method comprising contacting the bacterium with an effective amount of the therapeutic compound of claim 1.

20. The method of claim 19, wherein the contacting occurs in a subject comprising the bacterium, wherein the subject is a human.

21. A therapeutic compound comprising the sequence of GKX$_1$KFLX$_2$SKKKFGKAX$_3$VHEX$_4$X$_5$NS (Mag(i+4)2,15 (I2K, A9K, G18H); SEQ ID NO: 170), GKX$_1$KFLX$_2$SHKKFGKAX$_3$VGEX$_4$X$_5$NS (Mag(i+4)2,15 (I2K, A9H); SEQ ID NO: 171), GKX$_1$KFLX$_2$SHKKFGKAX$_3$VGEX$_4$X$_5$ES (Mag(i+4)2,15 (I2K, A9H, N21E); SEQ ID NO: 172), GKX$_1$KFLX$_2$SHKKFGKAX$_3$VHEX$_4$X$_5$ES (Mag(i+4)2,15 (I2K, A9H, G18H, N21E); SEQ ID NO: 173), GX$_1$GKFX$_2$HSKKKFGKAX$_3$VHEX$_4$X$_5$ES (Mag(i+4)1,15 (S8H, A9K, G18H, N21E); SEQ ID NO: 174), GX$_1$GKFX$_2$HSAKKFGKAX$_3$VGEX$_4$X$_5$NS (Mag(i+4)1,15 (A9K); SEQ ID NO:153), GX$_1$KFLX$_2$SKKKFGKAX$_3$VGEX$_4$X$_5$NS (Mag(i+4)2,15 (A9K), SEQ ID NO:154), or GX$_1$GSFX$_2$KKKAHVGKHX$_3$GKAX$_4$LTHYL (Pleu(i+4)1, 15(A9K); SEQ ID NO:177), wherein each of X$_1$, X$_2$, X$_3$, and X$_4$ are stapling amino acids, wherein the side chains of X$_1$ and X$_2$ are cross-linked and the side chains of X$_3$ and X$_4$ are cross-linked, wherein X$_5$ is norleucine.

22. A pharmaceutical composition comprising the therapeutic compound of claim 21.

23. The therapeutic compound of claim 21, wherein each of X$_1$, X$_2$, X$_3$, and X$_4$ is an α,α-disubstituted amino acid.

24. The therapeutic compound of claim 21, wherein: (i) each of X$_1$, X$_2$, X$_3$, and X$_4$ is S5; (ii) each of X$_1$, X$_2$, X$_3$, and X$_4$ is R5; (iii) each of X$_1$ and X$_2$ is S5 and each of X$_3$ and X$_4$ is R5; or (iv) each of X$_1$ and X$_2$ is R5 and each of X$_3$ and X$_4$ is S5, wherein S5 is (S)-2-(4-pentenyl)Alanine and R5 is (R)-2-(4-pentenyl)Alanine.

25. The therapeutic compound of claim 21, wherein the at least one bacterium is *E. coli*.

26. The therapeutic compound of claim 21, comprising the sequence GX$_1$GKFX$_2$HSAKKFGKAX$_3$VGEX$_4$X$_5$NS (Mag(i+4)1,15(A9K); SEQ ID NO:153).

27. The therapeutic compound of claim 21, comprising the sequence GKX$_1$KFLX$_2$SKKKFGKAX$_3$VHEX$_4$X$_5$NS (Mag(i+4)2,15(I2K, A9K, G18H); SEQ ID NO: 170).

28. The therapeutic compound of claim 21, comprising the sequence GKX$_1$KFLX$_2$SHKKFGKAX$_3$VGEX$_4$X$_5$NS (Mag(i+4)2,15(I2K, A9H); SEQ ID NO: 171).

29. A pharmaceutical composition comprising the therapeutic compound of claim 26.

30. A pharmaceutical composition comprising the therapeutic compound of claim 27.

31. A pharmaceutical composition comprising the therapeutic compound of claim 28.

32. A method of treating an infection caused by a bacterium, the method comprising administering a therapeutically-effective amount of the therapeutic compound of claim 21 to a subject having, or at risk of having, the infection caused by the bacterium.

33. A method of inhibiting the growth of a bacterium, the method comprising contacting the bacterium with an effective amount of the therapeutic composition of claim 26.

34. A method of treating an infection caused by a bacterium, the method comprising administering a therapeutically-effective amount of the therapeutic composition of claim 26 to a human subject having, or at risk of having, the infection caused by the bacterium.

35. The method of claim 34, wherein the bacterium is Gram-positive.

36. The method of claim 34, wherein the bacterium is Gram-negative.

37. A method of inhibiting the growth of a bacterium, the method comprising contacting the bacterium with an effective amount of the therapeutic composition of claim 27.

38. A method of treating an infection caused by a bacterium, the method comprising administering a therapeutically-effective amount of the therapeutic composition of claim 27 to a human subject having, or at risk of having, the infection caused by the bacterium.

39. The method of claim 38, wherein the bacterium is Gram-positive.

40. The method of claim 38, wherein the bacterium is Gram-negative.

41. A method of inhibiting the growth of a bacterium, the method comprising contacting the bacterium with an effective amount of the therapeutic composition of claim 28.

42. A method of treating an infection caused by a bacterium, the method comprising administering a therapeutically-effective amount of the therapeutic composition of claim 28 to a human subject having, or at risk of having, the infection caused by the bacterium.

43. The method of claim 42, wherein the bacterium is Gram-positive.

44. The method of claim 42, wherein the bacterium is Gram-negative.

45. A method of inhibiting the growth of a bacterium, the method comprising contacting the bacterium with an effective amount of the therapeutic compound of claim 21.

46. The method of claim 45, wherein the contacting occurs in a subject comprising the bacterium, wherein the subject is a human.

47. A therapeutic composition comprising an internally cross-linked polypeptide, the internally cross-linked polypeptide comprising:
   the sequence set forth in SEQ ID NO: 3, but having: (i) at least 2 amino acid substitutions, relative to SEQ ID NO: 3, with stapling amino acids, and (ii) 1 to 7 additional amino acid substitutions relative to SEQ ID NO: 1 or SEQ ID NO: 3,
   wherein 2 of the at least 2 amino acid substitutions with stapling amino acids are located at positions separated by 3 amino acids and are cross-linked to each other;
   wherein the 1 to 7 additional amino acid substitutions are one or more of: (i) a substitution with a basic residue; (ii) a substitution with a histidine; and (iii) a substitution with a D-alanine; (iv) a substitution with an alanine; and (v) a substitution of a methionine with a norleucine;
   wherein at least one of the 1 to 7 additional amino acid substitutions is selected from the group consisting of: (i) a substitution with a lysine at position 9 of SEQ ID NO:3; (ii) a substitution with a histidine; and (iii) a substitution with a glutamic acid; and
   wherein the cross-linked polypeptide inhibits the growth of at least one bacterium.

48. The therapeutic composition of claim 47, wherein 2 of the at least 2 amino acid substitutions with stapling amino acids are located at positions 3 and 7 or at positions 16 and 20 of SEQ ID NO:3.

49. The therapeutic composition of claim 47, wherein the internally cross-linked polypeptide comprises the sequence set forth in SEQ ID NO: 3, but having (i) 2 amino acid substitutions, relative to SEQ ID NO: 3, with stapling amino acids, wherein the 2 amino acid substitutions with stapling amino acids are located at positions separated by 3 amino acids.

50. The therapeutic composition of claim 47, wherein the internally cross-linked polypeptide comprises the sequence set forth in SEQ ID NO: 3, but having (i) 4 amino acid substitutions, relative to SEQ ID NO: 3, with stapling amino acids, wherein the 4 amino acid substitutions with stapling amino acids consist of two pairs of two amino acid substitutions with stapling amino acids, wherein the two amino acid substitutions of each of the two pairs are located at positions separated by 3 amino acids.

51. The therapeutic composition of claim 49, wherein the 2 amino acid substitutions with stapling amino acids are located at positions 3 and 7 or at positions 16 and 20 of SEQ ID NO: 3.

52. A pharmaceutical composition comprising the therapeutic composition of claim 47.

53. The therapeutic composition of claim 47, wherein the stapling amino acid is an α,α-disubstituted amino acid.

54. The therapeutic composition of claim 47, wherein the stapling amino acid is S5 [(S)-2-(4-pentenyl)Alanine] or R5 [(R)-2-(4-pentenyl)Alanine].

55. The therapeutic composition of claim 47, wherein the at least one bacterium is *E. coli*.

56. The therapeutic composition of claim 50, wherein the two pairs of two amino acid substitutions with stapling amino acids are located at positions: (i) 3 and 7, and (ii) 16 and 20.

57. A method of treating an infection caused by a bacterium, the method comprising administering a therapeutically-effective amount of the therapeutic composition of claim 47 to a subject having, or at risk of having, the infection caused by the bacterium.

58. The method of claim 57, wherein the subject is an animal.

59. The method of claim 58, wherein the animal is a mammal.

60. The method of claim 57, wherein the subject is a human.

61. The method of claim 57, wherein the subject is a plant.

62. The method of claim 57, wherein the bacterium is Gram-positive.

63. The method of claim 57, wherein the bacterium is Gram-negative.

64. The method of claim 57, wherein the bacterium is *Mycobacterium tuberculosis*.

65. The method of claim 57, wherein the infection is a bacterial vaginal infection.

66. The method of claim 65, wherein the bacterial vaginal infection is bacterial vaginosis.

67. The method of claim 65, wherein the bacterial vaginal infection is an infection with one or more bacterial organisms that increase the likelihood of transmission of a viral infection to the subject.

68. The method of claim 67, wherein the viral infection is a human immunodeficiency virus-1 infection.

69. The method of claim 67, wherein the viral infection is a human immunodeficiency virus-2 infection.

70. The method of claim 57, wherein the administration is topical to the vagina.

71. The method of claim 57, wherein the infection comprises a bacterial biofilm.

72. The method of claim 57, wherein the subject has or is at risk of having cystic fibrosis.

73. The method of claim 72, wherein the administration is to the lung.

74. The method of claim 57, further comprising administering to the subject a therapeutically-effective amount of an antibiotic.

75. A method of inhibiting the growth of a bacterium, the method comprising contacting the bacterium with an effective amount of the therapeutic composition-of claim 47.

76. The method of claim 75, wherein the contacting occurs in a subject comprising the bacterium.

77. The method of claim 75, wherein the contacting occurs in vitro.

78. The method of claim 75, wherein the inhibiting the growth of the bacterium is killing the bacterium.

79. A method of making an internally cross-linked peptide, the method comprising:
  providing a peptide having a sequence set forth in any one of SEQ ID NO: 153, 154 or 170-174 or 177; and
  cross-linking the peptide.

* * * * *

UNITED STATES PATENT AND TRADEMARK OFFICE
CERTIFICATE OF CORRECTION

PATENT NO. : 10,464,975 B2
APPLICATION NO. : 15/201235
DATED : November 5, 2019
INVENTOR(S) : Loren D. Walensky, Rida Mourtada and Gregory H. Bird Page 1 of 1

It is certified that error appears in the above-identified patent and that said Letters Patent is hereby corrected as shown below:

On the Title Page

Item (56), Right Column, "Other Publications", Line 7:
Delete "antimicroibal" and insert -- antimicrobial --, therefor.

Item (56), Right Column, "Other Publications", Line 8:
Delete "teh" and insert -- the --, therefor.

In the Claims

Column 304, Line 45:
In Claim 1, delete "8" and insert -- 8, --, therefor.

Column 305, Line 16:
In Claim 10, delete "8" and insert -- 8, --, therefor.

Column 306, Line 4:
In Claim 21, delete "(A9K)," and insert -- (A9K); --, therefor.

Column 307, Line 26:
In Claim 47, after "relative to" delete "SEQ ID NO: 1 or".

Signed and Sealed this
Twenty-eighth Day of January, 2020

Andrei Iancu
*Director of the United States Patent and Trademark Office*